(12) United States Patent
Rogers et al.

(10) Patent No.: US 11,154,201 B2
(45) Date of Patent: Oct. 26, 2021

(54) IMPLANTABLE MEDICAL DEVICES FOR OPTOGENETICS

(71) Applicants: The Board of Trustees of the University of Illinois, Urbana, IL (US); Washington University in St. Louis, St. Louis, MO (US)

(72) Inventors: John A. Rogers, Wilmette, IL (US); Gunchul Shin, Urbana, IL (US); Anthony R. Banks, Savoy, IL (US); Michael Bruchas, St. Louis, MO (US); Robert Gereau, St. Louis, MO (US)

(73) Assignees: The Board of Trustees of the University of Illinois, Urbana, IL (US); Washington University in St. Louis, St. Louis, MO (US)

( * ) Notice: Subject to any disclaimer, the term of this patent is extended or adjusted under 35 U.S.C. 154(b) by 83 days.

(21) Appl. No.: 16/086,377

(22) PCT Filed: Mar. 31, 2017

(86) PCT No.: PCT/US2017/025493
§ 371 (c)(1),
(2) Date: Sep. 19, 2018

(87) PCT Pub. No.: WO2017/173339
PCT Pub. Date: Oct. 5, 2017

(65) Prior Publication Data
US 2019/0053712 A1   Feb. 21, 2019

Related U.S. Application Data

(60) Provisional application No. 62/316,708, filed on Apr. 1, 2016.

(51) Int. Cl.
*A61B 5/00*   (2006.01)
*A61B 5/07*   (2006.01)
(Continued)

(52) U.S. Cl.
CPC .......... *A61B 5/0084* (2013.01); *A61B 5/0031* (2013.01); *A61B 5/0071* (2013.01);
(Continued)

(58) Field of Classification Search
USPC .......................................................... 607/88
See application file for complete search history.

(56) References Cited

U.S. PATENT DOCUMENTS

| 7,195,733 B2 | 3/2007 | Rogers et al. |
| 7,521,292 B2 | 4/2009 | Rogers et al. |

(Continued)

FOREIGN PATENT DOCUMENTS

| WO | WO 2012/054582 | 4/2012 |
| WO | WO 2014/126927 | 8/2014 |

(Continued)

OTHER PUBLICATIONS

Adamantidis et al. (2007) "Neural substrates of awakening probed with optogenetic control of hypocretin neurons," Nature. 450:420-424.

(Continued)

*Primary Examiner* — Nicole F Lavert
*Assistant Examiner* — Nicole F Johnson
(74) *Attorney, Agent, or Firm* — Leydig, Voit & Mayer, Ltd.

(57) ABSTRACT

Provided are implantable biomedical devices and related methods for interfacing with a target tissue. The devices comprise a substrate, an electronic device supported by the substrate and a freely positionable injectable needle electronically connected to the electronic device by a deformable interconnect, where the injectable needle has one or more optical sources provided on a distal tip end. The injectable needle may further comprise a photodetector.

38 Claims, 45 Drawing Sheets

(51) Int. Cl.
*A61B 17/04* (2006.01)
*A61N 5/06* (2006.01)

(52) U.S. Cl.
CPC ............ *A61B 5/076* (2013.01); *A61B 5/6848* (2013.01); *A61B 5/6868* (2013.01); *A61B 17/04* (2013.01); *A61B 2560/0219* (2013.01); *A61N 5/0601* (2013.01); *A61N 5/0622* (2013.01); *A61N 2005/0659* (2013.01); *A61N 2005/0661* (2013.01); *A61N 2005/0662* (2013.01)

(56) References Cited

U.S. PATENT DOCUMENTS

| | | |
|---|---|---|
| 7,557,367 B2 | 7/2009 | Rogers et al. |
| 7,622,367 B1 | 11/2009 | Nuzzo et al. |
| 7,704,684 B2 | 4/2010 | Rogers et al. |
| 7,705,280 B2 | 4/2010 | Nuzzo et al. |
| 7,799,699 B2 | 9/2010 | Nuzzo et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,367,035 B2 | 2/2013 | Rogers et al. |
| 8,394,706 B2 | 3/2013 | Nuzzo et al. |
| 8,440,546 B2 | 5/2013 | Nuzzo et al. |
| 8,470,701 B2 | 6/2013 | Rogers et al. |
| 8,552,299 B2 | 10/2013 | Rogers et al. |
| 8,562,095 B2 | 10/2013 | Alleyene et al. |
| 8,664,699 B2 | 3/2014 | Nuzzo et al. |
| 8,666,471 B2 | 3/2014 | Rogers et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 8,865,489 B2 | 10/2014 | Rogers et al. |
| 8,895,406 B2 | 11/2014 | Rogers et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,057,994 B2 | 6/2015 | Rogers et al. |
| 9,061,494 B2 | 6/2015 | Rogers et al. |
| 9,105,555 B2 | 8/2015 | Rogers et al. |
| 9,105,782 B2 | 8/2015 | Rogers et al. |
| 9,117,940 B2 | 8/2015 | Rogers et al. |
| 9,515,025 B2 | 12/2016 | Rogers et al. |
| 9,601,671 B2 | 3/2017 | Rogers et al. |
| 9,613,911 B2 | 4/2017 | Rogers et al. |
| 9,691,873 B2 | 6/2017 | Rogers et al. |
| 9,761,444 B2 | 9/2017 | Nuzzo et al. |
| 9,768,086 B2 | 9/2017 | Nuzzo et al. |
| 9,825,229 B2 | 11/2017 | Rogers et al. |
| 9,875,974 B2 | 1/2018 | Rogers et al. |
| 9,986,924 B2 | 6/2018 | Rogers et al. |
| 10,029,451 B2 | 7/2018 | Rogers et al. |
| 10,052,066 B2 | 8/2018 | Rogers et al. |
| 10,064,269 B2 | 8/2018 | Rogers et al. |
| 10,143,086 B2 | 11/2018 | Rogers et al. |
| 10,154,592 B2 | 12/2018 | Rogers et al. |
| 10,192,830 B2 | 1/2019 | Rogers et al. |
| 10,204,864 B2 | 2/2019 | Rogers et al. |
| 10,292,261 B2 | 5/2019 | Rogers et al. |
| 10,292,263 B2 | 5/2019 | Rogers et al. |
| 10,333,069 B2 | 6/2019 | Rogers et al. |
| 10,349,860 B2 | 7/2019 | Rogers et al. |
| 10,355,113 B2 | 7/2019 | Rogers et al. |
| 10,357,201 B2 | 7/2019 | Rogers et al. |
| 10,361,180 B2 | 7/2019 | Rogers et al. |
| 10,374,072 B2 | 8/2019 | Nuzzo et al. |
| 10,396,173 B2 | 8/2019 | Rogers et al. |
| 10,424,572 B2 | 9/2019 | Rogers et al. |
| 10,441,185 B2 | 10/2019 | Rogers et al. |
| 10,497,633 B2 | 12/2019 | Rogers et al. |
| 10,504,882 B2 | 12/2019 | Rogers et al. |
| 10,538,028 B2 | 1/2020 | Rogers et al. |
| 10,546,841 B2 | 1/2020 | Rogers et al. |
| 10,617,300 B2 | 4/2020 | Rogers et al. |
| 2004/0206916 A1 | 10/2004 | Colvin et al. |
| 2008/0055581 A1 | 3/2008 | Rogers et al. |
| 2010/0190229 A1 | 7/2010 | Zhang et al. |
| 2011/0230747 A1 | 9/2011 | Rogers et al. |
| 2011/0295100 A1 | 12/2011 | Hegde et al. |
| 2011/0316120 A1 | 12/2011 | Rogers et al. |
| 2012/0034622 A1 | 2/2012 | Ignatius et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2013/0036928 A1 | 2/2013 | Rogers et al. |
| 2013/0333094 A1 | 12/2013 | Rogers et al. |
| 2014/0191236 A1 | 7/2014 | Nuzzo et al. |
| 2014/0305900 A1 | 10/2014 | Rogers et al. |
| 2014/0361409 A1 | 12/2014 | Rogers et al. |
| 2014/0374872 A1 | 12/2014 | Rogers et al. |
| 2015/0001462 A1 | 1/2015 | Rogers et al. |
| 2015/0132873 A1 | 5/2015 | Rogers et al. |
| 2015/0141767 A1 | 5/2015 | Rogers et al. |
| 2015/0207012 A1 | 7/2015 | Rogers et al. |
| 2015/0290938 A1 | 10/2015 | Rogers et al. |
| 2015/0373831 A1 | 12/2015 | Rogers et al. |
| 2016/0066789 A1* | 3/2016 | Rogers ................. A61N 1/05 604/20 |
| 2017/0020402 A1 | 1/2017 | Rogers et al. |
| 2017/0128015 A1 | 5/2017 | Rogers et al. |
| 2017/0224257 A1 | 8/2017 | Rogers et al. |
| 2017/0231571 A1 | 8/2017 | Rogers et al. |
| 2017/0347891 A1 | 12/2017 | Rogers et al. |
| 2018/0014734 A1 | 1/2018 | Rogers et al. |
| 2018/0064377 A1 | 3/2018 | Rogers et al. |
| 2018/0165566 A1 | 6/2018 | Rogers et al. |
| 2018/0192952 A1 | 7/2018 | Rogers et al. |
| 2018/0274973 A1 | 9/2018 | Rogers et al. |
| 2018/0286820 A1 | 10/2018 | Rogers et al. |
| 2018/0359850 A1 | 12/2018 | Rogers et al. |
| 2019/0053712 A1 | 2/2019 | Rogers et al. |
| 2019/0090801 A1 | 3/2019 | Rogers et al. |
| 2020/0006540 A1 | 1/2020 | Nuzzo et al. |
| 2020/0013720 A1 | 1/2020 | Rogers et al. |

FOREIGN PATENT DOCUMENTS

| | | |
|---|---|---|
| WO | WO 2016/025430 | 2/2016 |
| WO | WO 2016/025438 | 2/2016 |
| WO | WO 2016/025468 | 2/2016 |
| WO | WO 2016/054348 | 4/2016 |
| WO | WO 2017/173339 | 10/2017 |

OTHER PUBLICATIONS

Adamantidis et al. (2011) "Optogenetic interrogation of dopaminergic modulation of the multiple phases of reward-seeking behavior," J. Neurosci. 31:10829-10835.

Airan et al. (2009) "Temporally precise in vivo control of intracellular signalling," Nature. 458:1025-1029.

Aleksandrova (Feb. 2016) "Specifics and Challenges to Flexible Organic Light-Emitting Devices," *Hindawi Publishing Corporation Advances in Material Science and Engineering*: 1-9.

Al-Hardan et al. (2010) "The effect of oxygen ratio on the crystallography and optical emission properties of reactive RF sputtered ZnO films," Physica B. 405:1081-1085.

Al-Hasani et al. (Sep. 2015) "Distinct Subpopulations of Nucleus Accumbens Dynorphin Neurons Drive Aversion and Reward," *Neuron* 87: 1063-1077.

Al-Hasani et al. (Jun. 21, 2013) "Locus Coeruleus Kappa Opioid Receptors modulate Reinstatement of Cocaine Place Preference through a Noradrenergic Mechanism," Neuropsychopharmacology. 38(12):2484-2497.

(56) References Cited

OTHER PUBLICATIONS

Andosca et al. (May 2012) "Experimental and theoretical studies on MEMS piezoelectric vibrational energy harvesters with mass loading," Sensors and Actuators A. 178:76-87.
Angelopoulos et al. (Sep. 17-21, 2012) "Manufacturing aspects of an ultra-thin chip technology," In; The Proceedings of the European Solid-State Device Research Conference (ESSDERC) 2012. Bordeaux, France. Ed.: Yann Deval. pp. 141-144.
Anikeeva et al. (Dec. 4, 2011) "Optetrode: a multichannel readout for optogenetic control in freely moving mice," Nat. Neurosci. 15:163-170.
APC International, Ltd. (2011) Piezoelectric Ceramics: Principles and Applications. APC International. p. 16.
Aravanis et al. (2007) An optical neural interface: in vivo control of rodent motor cortex with integrated fiberoptic and optogenetic technology. J. Neural Eng. 4, S143-S156 (2007).
Baca et al. (2007) "Printable Single-Crystal Silicon Micro/Nanoscale Ribbons, Platelets and Bars Generated from Bulk Wafers," Adv. Funct. Mater. 17:3051-3062.
Barbottin et al. (1989) "Instabilities in Field Effect Transistors," Ch. 15. In; Instabilities in Silicon Devices. vol. 2. Elsevier. Amsterdam, The Netherlands. pp. 553-657.
Baskoutas et al. (2011) "Transition in the Optical Emission Polarization of ZnO Nanorods," J. Phys. Chem. C. 115:15862-15867.
Bernardini et al. (1997) "Spontaneous polarization and piezoelectric constants of III-V nitrides," Physical Review B. 56:R10024.
Bettinger et al. (2010) "Biomaterials-based organic electronic devices," Polym Int. 59:563-567.
Bettinger et al. (2010) "Organic thin-film transistors fabricated on resorbable biomaterial substrates," Adv. Mater. 22:651-655.
Blom et al. (1990) "Thin-film ZnO as micromechanical actuator at low frequencies," Sensors and Actuators 21:226-228.
Boyden et al. (2005) "Millisecond-timescale, genetically targeted optical control of neural activity," *Nat. Neurosci.* 8(9): 1263-1268.
Briscoe (Aug. 30, 2012) "Measured efficiency of a ZnO nanostructured diode piezoelectric energy harvesting device," App. Phys. Lett. 101:093902.
Bruchas et al. (2011) "Selective p38α MAPK Deletion in Serotonergic Neurons Produces Stress Resilience in Models of Depression and Addiction," Neuron. 71:498-511.
Burghartz et al. (2009) "A New Fabrication and Assembly Process for Ultrathin Chips," IEEE Trans. Electron Dev. 56:321-327.
Calipari et al. (publicly available Feb. 2016) "In vivo imaging identifies temporal signature of D1 and D2 medium spiny neurons in cocaine reward," *Proceedings of the National Academy of Sciences* 113(10): 2726-2731.
Camacho et al. (2011) "Structural, optical and electrical properties of ZnO thin films grown by radio frequency (rf) sputtering in oxygen atmosphere," International Journal of the Physical Sciences. 6:6660-6663.
Campbell et al. (1991) "A silicon-based, three-dimensional neural interface: manufacturing processes for an intracortical electrode array," *IEEE Trans. Biomed. Eng.* 38(8): 758-768.
Cao et al. (2013) "An integrated μLED optrode for optogenetic stimulation and electrical recording," IEEE Trans. Biomed. Eng. 60:225-229.
Carcia et al. (2006) "High-performance ZnO thin-film transistors on gate dielectrics grown by atomic layer deposition," Appl. Phys. Lett. 88:123509.
Cardin et al. (2010) "Targeted optogenetic stimulation and recording of neurons in vivo using cell-type-specific expression of Channelrhodopsin-2," Nat. Protoc. 5:247-254.
Carson et al. (Aug. 31, 2012) "Transfer Printing Techniques for Materials Assembly and Micro/Nanodevice Fabrication," Adv. Mater. 24:5284-5318.
Carter et al. (2011) "Tuning arousal with optogenetic modulation of locus coeruleus neurons," Nat. Neuro. 13:1526-1533.
Cavanaugh et al. (Dec. 6, 2012) "Optogenetic inactivation modifies monkey visuomotor behavior," Neuron. 76:901-907.

Chang et al. (2010) "Direct-write piezoelectric polymeric nanogenerator with high energy conversion efficiency," Nano Lett. 10:726-731.
Chen et al. (2005) "Humidity Sensors: A Review of Materials and Mechanisms," Sensor Letters. 3:274-295.
Choi et al. (2003) "Investigation of Gate-Induced Drain Leakage (GIDL) Current in Thin Body Devices: Single-Gate Ultra-Thin Body, Symmetrical Double-Gate, and Asymmetrical Double-Gate MOSFETs," Jpn. J. Appl. Phys. 42:2073-2076.
Choi et al. (2009) "The effects of rapid thermal annealing on the performance of ZnO thin-film transistors," Journal of the Korean Physical Society. 55:1925-1930.
Choi-Yim et al. (1998) "The effect of silicon on the glass forming ability of the Cu 47 Ti 34 Zr 11 Ni 8 bulk metallic glass forming alloy during processing of composites," J. Appl. Phys. 83:7993.
Chung et al. (2011) "Fabrication of Releasable Single-Crystal Silicon—Metal Oxide Field-Effect Devices and Their Deterministic Assembly on Foreign Substrates," Adv. Func. Mater. 21:3029-3036.
Clark et al. (2009) "Chronic microsensors for longitudinal, subsecond dopamine detection in behaving animals," Nat. Methods. 7:126-129.
Cogan (2008) "Neural stimulation and recording electrodes," *Annu. Rev. Biomed. Eng.* 10: 275-309.
Coque et al. (2011) "Specific role of VTA dopamine neuronal firing rates and morphology in the reversal of anxiety-related, but not depression-related behavior in the ClockΔ19 mouse model of mania," Neuropsychopharmacology. 36:1478-1488.
Csutak et al. (2002) "CMOS-compatible high-speed planar silicon photodiodes fabricated on SOI substrates," IEEE Journal of Quantum Electronics. 38:193-196.
Czekalla et al. (2008) "Spatial fluctuations of optical emission from single ZnO/MgZnO nanowire quantum wells," Nanotechnology. 19:115202.
Dagdeviren et al. (Apr. 19, 2013) "Transient, Biocompatible Electronics and Energy Harvesters Based on ZnO," Small. 9(20):3398-3404.
Danckwerts (1950) "Absorption by simultaneous diffusion and chemical reaction," Transactions of the Faraday Society. 46:300-304.
David et al. (Apr. 26, 2012) "Dissolution Kinetics and Solubility of ZnO Nanoparticles Followed by AGNES," J. Phys. Chem. C. 116:11758-11767.
Deisseroth (2011) "Optogenetics," *Nat. Methods* 8(1): 26-29.
Diester et al. (2011) "An optogenetic toolbox designed for primates," Nat. Neurosci. 14:387-397.
Dryden (Aug. 2013) "Shining Light on Cells," Washington University in St. Louis School of Medicine Magazine. Accessible on the Internet at URL: https://outlook.wustl.edu/2013/aug/light-research/.
Du Hoffmann et al. (2011) "An inexpensive drivable cannulated microelectrode array for simultaneous unit recording and drug infusion in the same brain nucleus of behaving rats," J. Neurophysiol. 106:1054-1064.
Ducéré et al. (2005) "A capacitive humidity sensor using cross-linked cellulose acetate butyrate," Sensors and Actuators B: Chemical. 106:331-334.
Elwassif et al. (2006) "Bio-heat transfer model of deep brain stimulation-induced temperature changes," J. Neural Eng. 3:306-315.
Esler et al. (2010) "Instrumentation for low frequency EIT studies of the human head and its validation in phantom experiments," Journal of Physics: Conference Series. 224:012007.
Federal Communications Commission (FCC) (1996) "Guidelines for Evaluating the Environmental Effects of Radiofrequency Radiation," Accessible on the Internet at URL: http://transition.fcc.gov/Bureaus/Engineering_Technology/Orders/1996/fcc96326.txt. [Last Accessed Dec. 9, 2015].
Felix-Oritz et al. (2013) "BLA to vHPC inputs modulate anxiety-related behaviors," Neuron 79: 658-664.
Fenno et al. (2011) "The Development and Application of Optogenetics," Annu. Rev. Neurosci. 34:389-412.
Fink et al. (2002) "Enhancement of device performance in vertical sub-100 nm MOS devices due to local channel doping," Solid State Electron. 46:387-391.

(56) References Cited

OTHER PUBLICATIONS

Fulati et al. (2009) "Miniaturized pH Sensors Based on Zinc Oxide Nanotubes/Nanorods," Sensors. 9:8911-8923.
Gerischer et al. (1992) "Chemical dissolution of zinc oxide crystals in aqueous electrolytes—An analysis of the kinetics," Electrochimica Acta. 37:827-835.
Gerits et al. (Apr. 26, 2013) "Optogenetics in primates: A shining future?" Trends Genet. 29(7):403-411.
Gradinaru et al. (2010) "Molecular and Cellular Approaches for Diversifying and Extending Optogenetics," Cell. 141:154-165.
Grosjean et al. (2006) "Hydrolysis of Mg—salt and MgH2—salt mixtures prepared by ball milling for hydrogen production," Journal of Alloys and Compounds. 416:296-302.
Gullapalli et al. (2010) "Flexible Piezoelectric ZnO—Paper Nanocomposite Strain Sensor," Small. 6:1641-1646.
Gunaydin et al. (2014) "Dopaminergic dynamics contributing to social behavior,"*Cold Spring Harbor Symposia on Quantitative Biology* 79: 221-227.
Gupta et al. (2010) "Development of gas sensors using ZnO nanostructures," J. Chem. Sci. 122:57-62.
Han et al. (2009) "Millisecond-Timescale Optical Control of Neural Dynamics in the Nonhuman Primate Brain," Neuron 62:191-198.
Harrison et al. (2010) "A wireless neural/EMG telemetry system for freely moving insects," In; IEEE Int. Symp. Circuits Syst. ISCAS. Proc. 2010. pp. 2940-2943.
Hoffman et al. (2003) "ZnO-based transparent thin-film transistors," Appl. Phys. Lett. 82:733-735.
Huang et al. (2011) "A flexible pH sensor based on the iridium oxide sensing film," Sensors and Actuators A: Physical. 169:1-11.
Hudson et al. (2008) "The biocompatibility of mesoporous silicates," Biomaterials. 29:4045-4055.
Hwang et al. (2012) "A Physically Transient Form of Silicon Electronics," Science 337:1640-1644.
Ilican et al. (2008) "Preparation and characterization of ZnO thin films deposited by sol-gel spin coating method," Journal of Optoelectronics and Advance Materials. 10:2578-2583.
International Search Report with Written Opinion corresponding to International Patent Application No. PCT/US2014/015825, dated Apr. 29, 2014.
Irimia-Vladu et al. (2010) "Biocompatible and Biodegradable Materials for Organic Field-Effect Transistors," Adv. Funct. Mater. 20:4069-4076.
Ito et al. (2001) "Development and characteristics of a biological tissue-equivalent phantom for microwaves," Electronics and Communications in Japan (Part I: Communications). 84(4):67-77.
Iwai et al. (2011) "A simple head-mountable LED device for chronic stimulation of optogenetic molecules in freely moving mice," Neurosci. Res. 70:124-127.
Jennings et al. (Apr. 11, 2013) "Distinct extended amygdala circuits for divergent motivational states," Nature. 496:224-228.
Jeon et al. (2007) "Low-Voltage Zinc-Oxide Thin-Film Transistors on a Conventional SiO2 Gate Insulator Grown by Radio-Frequency Magnetron Sputtering at Room Temperature," Journal of the Korean Physical Society. 51:1999-2003.
Jeong et al. (Jul. 2015) "Wireless Optofluidic Systems for Programmable In Vivo Pharmacology and Optogenetics," *Cell* 162: 662-674.
Kang et al. (publicly available Jan. 2016). "Bioresorbable silicon electronic sensors for the brain," Nature 530: 71-79.
Kim et al. (2008) "Stretchable and Foldable Silicon Integrated Circuits," Science. 320:507-511.
Kim et al. (2010) "Dissolvable films of silk fibroin for ultrathin, conformal bio-integrated electronics," Nat. Mater. 9:511-517.
Kim et al. (2010) "Waterproof AlInGaP optoelectronics on stretchable substrates with applications in biomedicine and robotics," Nat. Mater. 9:929-937.
Kim et al. (Apr. 10, 2012) "Optogenetic mimicry of the transient activation of dopamine neurons by natural reward is sufficient for operant reinforcement," Plos One. 7:e33612.
Kim et al. (Apr. 12, 2013) "Injectable, Cellular-Scale Optoelectronics with Applications for Wireless Optogenetics," Science. 340(6129):211-216.
Kim et al. (Apr. 2012) "Microscale Inorganic Light-Emitting Diodes on Flexible and Stretchable Substrates," IEEE Photonics J. 4:607-612.
Kim et al. (Aug. 12, 2011) "Epidermal electronics," Science 333:838-843.
Kim et al. (publicly available Nov. 2014) "Epidermal Electronics with Advanced Capabilities in Near-Field Communication," *Small* 11(8): 906-912.
Kim et al. (Jun. 8, 2012) "Material considerations for peripheral nerve interfacing," MRS Bull. 37:573-580.
Kim et al. (publicly available Jun. 2015) "Miniaturized Flexible Electronic Systems with Wireless Power and Near-Field Communication Capabilities," *Advanced Functional Materials* 25: 4761-4767.
Kim et al. (Mar. 20, 2013) "Diverging neural pathways assemble a behavioural state from separable features in anxiety," Nature. 496:219-223.
Kim et al. (Mar. 30, 2012) "High efficiency, microscale GaN LEDs and their thermal properties on unusually substrates," Small. 8:1643-1649.
Kim et al. (May 7, 2013) "Deterministic assembly of releasable single crystal silicon-metal oxide field-effect devices formed from bulk wafers," 102:182104.
Kim et al. (Feb. 2016) "Simultaneous fast measurement of circuit dynamics at multiple sites across the mammalian brain," *Nature Methods* 13(4): 325-328 doi:10.1038/nmeth.3770.
Klapoetke et al. (Oct. 16, 2012) "Independent two-color optogenic excitation of neural populations in mouse cortical slices," In; The 42nd Annual Meeting of the Society for Neuroscience. New Orleans, Louisiana.—Presentation Abstract.
Knuesel et al. (2010) "Self-assembly of microscopic chiplets at a liquid—liquid—solid interface forming a flexible segmented monocrystalline solar cell," Proc. Natl. Acad. Sci. USA. 107:993-998.
Kozai et al. (2009) "Insertion shuttle with carboxyl terminated self-assembled monolayer coatings for implanting flexible polymer neural probes in the brain," J. Neuro. Met. 184:199-205.
Kozai et al. (2012) "Ultrasmall implantable composite microelectrodes with bioactive surfaces for chronic neural interfaces," *Nat. Mater.* 11: 1065-1073.
Kravitz et al. (Nov. 21, 2012) "Optogenetic identification of striatal projection neuron subtypes during in vivo recordings," Brain Res. 1511:21-32.
Krejčiřík et al. (2007) "Non-Hermitian spectral effects in a PT-symmetric waveguide," Journal of Physics A: Mathematical and Theoretical. 41:244013.
Kumar et al. (2006) "Ultrasensitive DNA sequence detection using nanoscale ZnO sensor arrays," Nanotechnology. 17:2875-2881.
Kumar et al. (2011) "ZnO nanoparticle as catalyst for efficient green one-pot synthesis of coumarins through Knoevenagel condensation," J. Chem. Sci. 123:615-621.
Kuo (2004) "Deposition of Dielectric Thin Films for a-Si:H TFT," Ch. 6 In; Thin Film Transistors Materials and Processe. vol. 1. Klewer Academic. Norwell, Massachusetts.
Kurzweil (2009) "Metal Oxides and Ion-Exchanging Surfaces as pH Sensors in Liquids: State-of-the-Art and Outlook," Sensors (Basel). 9:4955-4985.
Lammel et al. (Oct. 14, 2012) "Input-specific control of reward and aversion in the ventral tegmental area," Nature. 491:212-217.
Lee et al. (2005) "Dielectrophoresis and Chemically Mediated Directed Self-Assembly of Micrometer-Scale Three-Terminal Metal Oxide Semiconductor Field-Effect Transistors," Adv. Mater. 17:2671-2677.
Lee et al. (Mar. 2015) "Noninvasive in vivo imaging reveals differences between tectorial membrane and basilar membrane traveling waves in the mouse cochlea," *Proceedings of the National Academy of Sciences of the United States of American PNAS* 12(10): 3128-3133.

(56) References Cited

OTHER PUBLICATIONS

Legnani et al. (2008) "Bacterial cellulose membrane as flexible substrate for organic light emitting devices," Thin Solid Films. 517:1016-1020.
Lewis (Mar. 2016) "Only the lonely," *Nature Reviews Neuroscience* 17: 1 pp. doi:10.1038/nrn.2016.26.
Li et al. (2008) "Cellular Level Biocompatibility and Biosafety of ZnO Nanowires," J. Phys. Chem. C. 112:20114-20117.
Li et al. (Jan. 21, 2013) "An Analytical Model of Reactive Diffusion for Transient Electronics," Advanced Functional Materials. 23:3106-3114.
Mack et al. (2006) "Mechanically Flexible Thin-Film Transistors that use Ultrathin Ribbons of Silicon Derived from Bulk Wafers," Appl. Phys. Lett. 88:213101.
Mannsfeld et al. (2010) "Highly sensitive flexible pressure sensors with micro-structured rubber as the dielectric layer," Nat. Mater. 9:859-864.
Martinez-Boubeta et al. (2010) "Self-assembled multifunctional Fe/MgO nanospheres for magnetic resonance imaging and hyperthermia," Nanomedicine: Nanotechnology, Biology, and Medicine. 6:362-370.
Masuda et al. (2003) "Transparent thin film transistors using ZnO as an active channel layer and their electrical properties," J. Appl. Phys. 93:1624.
Matthews et al. (Feb. 2016) "Dorsal raphe dopamine neurons represent the experience of social isolation," *Cell* 164(4): 617-631.
Mattis et al. (2011) "Principles for applying optogenetic tools derived from direct comparative analysis of microbial opsins," Nat. Methods 18:159-172.
Mattsson et al. (2007) "Development of an infrared thermopile detector with a thin self-supporting SU-8 membrane," IEEE SENSORS 2007 Conference. pp. 836-839.
McCall et al. (2013) "Fabrication and application of flexible, multimodal light-emitting devices for wireless optogenetics," *Nat. Protoc.* 8(12): 2413-2428.
McGranahan et al. (Jul. 27, 2011) "α4β2 nicotinic acetylcholine receptors on dopaminergic neurons mediate nicotine reward and anxiety relief," J. Neurosci. 31:10891-10902.
Meitl et al. (2006) "Transfer printing by kinetic control of adhesion to an elastomeric stamp," Nat. Mater. 5:33-38.
Miyamoto et al. (2004) "High-electron-mobility ZnO epilayers grown by plasma-assisted molecular beam epitaxy," Journal of Crystal Growth. 265:34-40.
Modafe et al. (2005) "Embedded benzocyclobutene in silicon: An integrated fabrication process for electrical and thermal isolation in MEMS," Microelectron. Eng. 82:154-167.
Momose et al. (2002) "Ultrathin gate oxide CMOS on (111) surface-oriented Si substrate," IEEE Trans. Electron. Dev. 49:1597-1605.
Mondal et al. (2008) "Preparation of Al-Doped ZnO (AZO) Thin Film by SILAR," Journal of Physical Sciences. 12:221-229.
Montgomery et al. (Aug. 2015) "Wirelessly powered, fully internal optogenetics for brain, spinal and peripheral circuits in mice," *Nat. Methods* 12(10): 969-974.
Moore et al. (1959) "II. Diffusion of zinc and oxygen in zinc oxide," Discussions of the Faraday Society. 28:86-93.
Moravej et al. (2011) "Biodegradable Metals for Cardiovascular Stent Application: Interests and New Opportunities," Int. J. Mol. Sci. 12:4250-4270.
Moscarello et al. (2014) "Diverse effects of conditioned threat stimuli on behavior," *Cold Spring Harbor Symposia on Quantitative Biology* 79: 11-19.
Mudunkotuwa et al. (Nov. 28, 2011) "Dissolution of ZnO Nanoparticles at Circumneutral pH: A Study of Size Effects in the Presence and Absence of Citric Acid," Langmuir. 28:396-403.
Ondo-Ndong et al. (2003) "Electrical properties of zinc oxide sputtered thin films," Microelectronics Journal. 34:1087-1092.
Ordonez et al. (Jun. 8, 2012) "Thin films and microelectrode arrays for neuroprosthetics," MRS Bull. 37:590-598.
Osakada et al. (2011) "New Rabies Virus Variants for Monitoring and Manipulating Activity and Gene Expression in Defined Neural Circuits," Neuron. 71:617-631.
Osakada et al. (Jul. 25, 2013) "Design and generation of recombinant rabies virus vectors," Nat. Protoc. 8:1583-1601.
Pang et al. (Jul. 29, 2012) "A flexible and highly sensitive strain-gauge sensor using reversible interlocking of nanofibres," Nat. Mater. 11:795-801.
Panilaitis et al. (2003) "Macrophage responses to silk," Biomaterials. 24:3079-3085.
Park et al. (2008) "Theoretical and Experimental Studies of Bending of Inorganic Electronic Materials on Plastic Substrates," Adv. Funct. Mater. 18:2673-2684.
Park et al. (2009) "Printed Assemblies of Inorganic Light-Emitting Diodes for Deformable and Semitransparent Displays," Science. 325:977-981.
Park et al. (Nov. 2015) "Soft, stretchable, fully implantable miniaturized optoelectronic systems for wireless optogenetics," *Nat. Biotechnol.* 33(12): 1280-1286.
Park et al. (Jul. 2015) "Ultraminiaturized photovoltaic and radio frequency powered optoelectronic systems for wireless optogenetics," *J. Neural Eng.* 12, 056002, 9 pp.
Park et al. (Dec. 13, 2016) "Stretchable multichannel antennas in soft wireless optoelectronic implants for optogenetics" PNAS 113(50): E8169-E8177.
Pierret (1996) "Non Ideal MOS," Ch. 18 In; Semiconductor Device Fundamentals. Addison-Wesley. Natick, Massachusetts. pp. 645-690.
Qing et al. (2010) "Nanowire transistor arrays for mapping neural circuit in acute brain slices," Proc. Natl. Acad. Sci. USA. 107:1882-1887.
Reed et al. (Dec. 9, 2011) "Solubility of nano-zinc oxide in environmentally and biologically important matrices," Environ. Toxicol. Chem. 31:93-99.
Richter et al. (2008) "Review on Hydrogel-based pH Sensors and Microsensors," Sensors. 8:561-581.
Rogers et al. (2011) "Synthesis, assembly and applications of semiconductor nanomembranes," Nature. 477:45-53.
Ruiz et al. (Jun. 12, 2013) "Optogenetics through windows on the brain in the nonhuman primate," J. Neurophysiol. 110(6):1455-1467.
Saad et al. (2008) "Characterization of various zinc oxide catalysts and their activity in the dehydration-dehyrogenation of isobutanol," J. Serb. Chem. Soc. 73:997-1009.
Sato et al. (1999) "Anisotropic etching rates of single-crystal silicon for TMAH water solution as a function of crystallographic orientation," Sens. Actuators A. 73:131-137.
Search Report and Written Opinion, dated Aug. 25, 2017, corresponding to International Application No. PCT/US/2017/025493 (filed Mar. 31, 2017), related to the present application, 16 pp.
Sekitani et al. (2009) "Organic nonvolatile memory transistors for flexible sensor arrays," Science. 326:1516-1519.
Sekitani et al. (Mar. 2012) "Stretchable organic integrated circuits for large-area electronic skin surface," MRS Bull. 37:236-245.
Shahrjerdi et al. (Dec. 18, 2012) "Extremely Flexible Nanoscale Ultrathin Body Silicon Integrated Circuits on Plastic," Nano Lett. 13:315-320.
Shen et al. (2007) "Submicron particles of SBA-15 modified with MgO as carriers for controlled drug delivery," Chem. Pharm. Bull. 55:985-991.
Shimizu et al. (Jun. 2012) "Zinc Oxide Paste as Sunscreen in the Postoperative Period," Dermatologic Surgery. 38:965-966.
Silverman et al. (2010) "Behavioural phenotyping assays for mouse models of autism," *Nature Reviews Neuroscience* 11: 490-502.
Siuda et al. (Jan. 2016) "Chemogenetic and Optogenetic Activation of Gαs Signaling in the Basolateral Amygdala Induces Acute and Social Anxiety-Like States," *Neuropsychopharmacology* 41: 2011-2023 DOI: 10.1038/npp.2015.371.
Siuda et al. (Sep. 2015) "Optodynamic Simulation of b-Adrenergic Receptor Signaling," *Nature Communications* 6:8480 | DOI: 10.1038/ncomms9480.
Solano et al. (2007) "Thermal and mechanical analysis of an SU8 polymeric actuator using infrared thermography," Proceedings of

(56) References Cited

OTHER PUBLICATIONS the Institution of Mechanical Engineers, Part C: Journal of Mechanical Engineering Science. 222(1):73-86.
Song et al. (2003) "Understanding Magnesium Corrosion—A Framework for Improved Alloy Performance," Advanced Engineering Materials. 5:837-858.
Song et al. (2009) "Mechanics of noncoplanar mesh design for stretchable electronic circuits," Journal of Applied Physics. 105:123516.
Sparta et al. (Dec. 8, 2011) "Construction of implantable optical fibers for long-term optogenetic manipulation of neural circuits," Nat. Protoc. 7:12-23.
Sparta et al. (May 16, 2013) Optogenetic strategies to investigate neural circuitry engaged by stress. Behav. Brain Res. 255:19-25.
Staiger et al. (2006) "Magnesium and its alloys as orthopedic biomaterials: a review," Biomaterials. 27:1728-1734.
Stamatakis et al. (Jun. 24, 2012) "Activation of lateral habenula inputs to the ventral midbrain promotes behavioral avoidance," Nat. Neuro. 12:1105-1107.
Stark et al. (Apr. 11, 2012) "Diode probes for spatiotemporal optical control of multiple neurons in freely moving animals," J. Neurophysiol. 108:349-363.
Stathis et al. (2006) "The negative bias temperature instability in MOS devices: A review," Microelec. Rel. 46:270-286.
Stauth et al. (2006) "Self-assembled single-crystal silicon circuits on plastic," Proc. Natl. Acad. Sci. USA. 19:13922-13927.
Stuber et al. (2011) "Excitatory transmission from the amygdala to nucleus accumbens facilitates reward seeking," Nature. 475:377-380.
Su et al. (Dec. 1, 2011) "Postbuckling analysis and its application to stretchable electronics," Journal of the Mechanics and Physics of Solids. 60:487-508.
Szarowski et al. (2003) "Brain responses to micro-machined silicon devices," Brain Res. 983:23-35.
Szuts et al. (2011) "A wireless multi-channel neural amplifier for freely moving animals," Nat. Neurosci. 14:263-269.
Takagi et al. (1994) "On the universality of inversion layer mobility in Si MOSFET's: Part II—effects of surface orientation," IEEE Trans. Electron Dev. 41:2363-2368.
Takei et al. (2010) "Nanowire active-matrix circuitry for low-voltage macroscale artificial skin," Nat. Mater. 9:821-826.
Takeuchi et al. (2004) "3D flexible multichannel neural probe array," J. Micromech. Microeng. 14:104-107.
Tan et al. (2012) "GABA neurons of the VTA drive conditioned place aversion," Neuron. 73:1173-1183.
Tao et al. (Jan. 20, 2012) "Silk-Based Conformal, Adhesive, Edible Food Sensors," Adv. Mater. 24:1067-1072.
Tian et al. (2010) "Three-diemensional, flexible, nanoscale field effect transistors as localized bioprobes," Science. 329:830-834.
Tian et al. (Aug. 26, 2012) "Macroprous nanowire nanoelectronic scaffolds for synthetic tissues," Nat. Mater. 11:986-994.
Trewyn et al. (2008) "Biocompatible mesoporous silica nanoparticles with different morphologies for animal cell membrane penetration," Chemical Engineering Journal. 137:23-29.
Tsai et al. (2009) "Phasic firing in dopaminergic neurons is sufficient for behavioral conditioning," Science. 324:1080-1084.
Tye et al. (2011) "Amygdala circuitry mediating reversible and bidirectional control of anxiety," Nature. 471:358-362.
Tye et al. (Mar. 20, 2012) "Optogenetic investigation of neural circuits underlying brain disease in animal models," Nat. Rev. Neurosci. 13:251-266.
Valtiner et al. (2008) "Stabilization and Acidic Dissolution Mechanism of Single-Crystalline ZnO(0001) Surfaces in Electrolytes Studied by In-Situ AFM Imaging and Ex-Situ LEED," Langmuir. 24:5350-5358.
Viventi et al. (2010) "A conformal, bio-Interfaced class of silicon electronics for mapping cardiac electrophysiology," Sci. Transl. Med. 2:24ra22.
Wales et al. (2003) "Stationary points and dynamics in high-dimensional systems," J. Chem. Phys. 119:12409-12416.

Wang et al. (1999) "Electromechanical coupling and output efficiency of piezoelectric bending actuators," IEEE Transactions on Ultrasonics, Ferroelectrics and Frequency Control. 46:638-646.
Wegner et al. (2006) "In situ formation and hydrolysis of Zn nanoparticles for H2 production by the 2-step ZnO/Zn water-splitting thermochemical cycle," International Journal of Hydrogen Energy. 31:55-61.
Wentz et al. (2011) "A wirelessly powered and controlled device for optical neural control of freely-behaving animals," J. Neural Eng. 8:046021.
Witten et al. (2011) "Recombinase-driver rat lines: tools, techniques, and optogenetic application to dopamine-mediated reinforcement," Neuron. 72:721-733.
Wong et al. (2000) "InxGa1—xN light emitting diodes on Si substrates fabricated by Pd—In metal bonding and laser lift-off," Appl. Phys. Lett. 77:2822-2824.
Yizhar et al. (2011) "Optogenetics in neural systems," Neuron. 71:9-34.
Zhai et al. (Oct. 23, 2012) "High-Performance Flexible Thin-Film Transistors Exfoliated from Bulk Wafer," Nano Lett. 12:5609-5615.
Zhang et al. (2010) "Optogenetic interrogation of neural circuits: technology for probing mammalian brain structures," Nat. Protoc. 5:439-456.
Zhang et al. (2010) "Fabrication and comparative study of top-gate and bottom-gate ZnO—TFTs with various insulator layers," J. Mater. Sci.: Mater. Electron. 21:671-675.
Zhang et al. (Oct. 19, 2012) "Serine 363 is required for NOPR desensitization, internalization, and arrestin signaling," J. Biol. Chem. 287(50):42019-42030.
Zhao et al. (2004) "Piezoelectric Characterization of Individual Zinc Oxide Nanobelt Probed by Piezoresponse Force Microscope," Nano Lett. 4:587-590.
Zhao et al. (2009) "Wireless Activation of Neurons in Brain Slices Using Nanostructured Semiconductor Photoelectrodes," Angew. Chem. Int. Ed. 48:2407-2410.
Zheng et al. (2009) "In Vitro and In Vivo Biocompatibility Studies of ZnO Nanoparticles," International Journal of Modern Physics B. 23:1566-1571.
Zhou et al. (2006) "Dissolving Behavior and Stability of ZnO Wires in Biofluids: A Study on Biodegradability and Biocompatibility of ZnO Nanostructures," Adv. Mater. 18:2432-2435.
Zhou et al. (Feb. 18, 2013) "Fast flexible electronics with strained silicon nanomembranes," Scientific Reports. 3:1291.
Zhu et al. (2010) "Flexible High-Output Nanogenerator Based on Lateral ZnO Nanowire Array," Nano Lett. 10:3151-3155.
Zorzos et al. (2010) "Multiwaveguide implantable probe for light delivery to sets of distributed brain targets," Opt. Lett. 35:4133-4135.
Zorzos et al. (Dec. 1, 2012) "Three-dimensional multiwaveguide probe array for light delivery to distributed brain circuits," Opt. Lett. 37:4841-4843.
U.S. Appl. No. 11/001,689, filed Dec. 1, 2004.
U.S. Appl. No. 11/115,954, filed Apr. 27, 2005.
U.S. Appl. No. 11/145,574, filed Jun. 2, 2005.
U.S. Appl. No. 11/145,542, filed Jun. 2, 2005.
U.S. Appl. No. 11/421,654, filed Jun. 1, 2006.
U.S. Appl. No. 11/423,287, filed Jun. 9, 2006.
U.S. Appl. No. 11/423,192, filed Jun. 9, 2006.
U.S. Appl. No. 11/465,317, filed Aug. 17, 2006.
U.S. Appl. No. 11/675,659, filed Feb. 16, 2007.
U.S. Appl. No. 11/782,799, filed Jul. 25, 2007.
U.S. Appl. No. 11/851,182, filed Sep. 6, 2007.
U.S. Appl. No. 11/858,788, filed Sep. 20, 2007.
U.S. Appl. No. 11/981,380, filed Oct. 31, 2007.
U.S. Appl. No. 12/372,605, filed Feb. 17, 2009.
U.S. Appl. No. 12/398,811, filed Mar. 5, 2009.
U.S. Appl. No. 12/405,475, filed Mar. 17, 2009.
U.S. Appl. No. 12/418,071, filed Apr. 3, 2009.
U.S. Appl. No. 12/522,582, filed Jul. 9, 2009.
U.S. Appl. No. 12/564,566, filed Sep. 22, 2009.
U.S. Appl. No. 12/669,287, filed Jan. 15, 2010.
U.S. Appl. No. 12/778,588, filed May 12, 2010.
U.S. Appl. No. 12/844,492, filed Jul. 27, 2010.

(56) References Cited

OTHER PUBLICATIONS

U.S. Appl. No. 12/892,001, filed Sep. 28, 2010.
U.S. Appl. No. 12/916,934, filed Nov. 1, 2010.
U.S. Appl. No. 12/947,120, filed Nov. 16, 2010.
U.S. Appl. No. 12/996,924, filed Dec. 8, 2010.
U.S. Appl. No. 12/968,637, filed Dec. 15, 2010.
U.S. Appl. No. 13/046,191, filed Mar. 11, 2011.
U.S. Appl. No. 13/071,027, filed Mar. 24, 2011.
U.S. Appl. No. 13/095,502, filed Apr. 27, 2011.
U.S. Appl. No. 13/100,774, filed May 4, 2011.
U.S. Appl. No. 13/113,504, filed May 23, 2011.
U.S. Appl. No. 13/120,486, filed Aug. 4, 2011.
U.S. Appl. No. 13/228,041, filed Sep. 8, 2011.
U.S. Appl. No. 13/270,954, filed Oct. 11, 2011.
U.S. Appl. No. 13/349,336, filed Jan. 12, 2012.
U.S. Appl. No. 13/441,618, filed Apr. 6, 2012.
U.S. Appl. No. 13/441,598, filed Apr. 6, 2012.
U.S. Appl. No. 13/472,165, filed May 15, 2012.
U.S. Appl. No. 13/486,726, filed Jun. 1, 2012.
U.S. Appl. No. 13/492,636, filed Jun. 8, 2012.
U.S. Appl. No. 13/549,291, filed Jul. 13, 2012.
U.S. Appl. No. 13/596,343, filed Aug. 28, 2012.
U.S. Appl. No. 13/624,096, filed Sep. 21, 2012.
U.S. Appl. No. 13/801,868, filed Mar. 13, 2013.
U.S. Appl. No. 13/835,284, filed Mar. 15, 2013.
U.S. Appl. No. 13/853,770, filed Mar. 29, 2013.
U.S. Appl. No. 13/974,963, filed Aug. 23, 2013.
U.S. Appl. No. 14/033,765, filed Sep. 23, 2013.
U.S. Appl. No. 14/140,299, filed Dec. 24, 2013.
U.S. Appl. No. 14/155,010, filed Jan. 14, 2014.
U.S. Appl. No. 14/173,525, filed Feb. 5, 2014.
U.S. Appl. No. 14/209,481, filed Mar. 13, 2014.
U.S. Appl. No. 14/220,910, filed Mar. 20, 2014.
U.S. Appl. No. 14/220,923, filed Mar. 20, 2014.
U.S. Appl. No. 14/246,962, filed Apr. 7, 2014.
U.S. Appl. No. 14/250,671, filed Apr. 11, 2014.
U.S. Appl. No. 14/251,259, filed Apr. 11, 2014.
U.S. Appl. No. 14/479,100, filed Sep. 5, 2014.
U.S. Appl. No. 14/504,736, filed Oct. 2, 2014.
U.S. Appl. No. 14/521,319, filed Oct. 22, 2014.
U.S. Appl. No. 14/532,687, filed Nov. 4, 2014.
U.S. Appl. No. 14/599,290, filed Jan. 16, 2015.
U.S. Appl. No. 14/686,304, filed Apr. 14, 2015.
U.S. Appl. No. 14/706,733, filed May 7, 2015.
U.S. Appl. No. 14/766,926, filed Aug. 10, 2015.
U.S. Appl. No. 14/766,301, filed Aug. 6, 2015.
U.S. Appl. No. 14/766,333, filed Aug. 6, 2015.
U.S. Appl. No. 14/772,312, filed Sep. 2, 2015.
U.S. Appl. No. 14/772,354, filed Sep. 2, 2015.
U.S. Appl. No. 14/789,645, filed Jul. 1, 2015.
U.S. Appl. No. 14/800,363, filed Jul. 15, 2015 .
U.S. Appl. No. 14/818,109, filed Aug. 4, 2015.
U.S. Appl. No. 14/944,039, filed Nov. 17, 2015.
U.S. Appl. No. 15/084,091, filed Mar. 29, 2016.
U.S. Appl. No. 15/084,112, filed Mar. 29, 2016.
U.S. Appl. No. 15/084,211, filed Mar. 29, 2016.
U.S. Appl. No. 15/146,629, filed May 4, 2016.
U.S. Appl. No. 15/339,338, filed Oct. 31, 2016.
U.S. Appl. No. 15/349,525, filed Nov. 11, 2016.
U.S. Appl. No. 15/351,234, filed Nov. 14, 2016.
U.S. Appl. No. 15/354,951, filed Nov. 17, 2016.
U.S. Appl. No. 15/374,926, filed Dec. 9, 2016.
U.S. Appl. No. 15/375,514, filed Dec. 12, 2016.
U.S. Appl. No. 15/402,684, filed Jan. 10, 2017.
U.S. Appl. No. 15/402,718, filed Jan. 10, 2017.
U.S. Appl. No. 15/470,780, filed Mar. 27, 2017.
U.S. Appl. No. 15/402,723, filed Jan. 10, 2017.
U.S. Appl. No. 15/477,865, filed Apr. 3, 2017.
U.S. Appl. No. 15/501,364, filed Feb. 2, 2017.
U.S. Appl. No. 15/501,373, filed Feb. 2, 2017.
U.S. Appl. No. 15/501,379, filed Feb. 2, 2017.
U.S. Appl. No. 15/515,494, filed Mar. 29, 2017.
U.S. Appl. No. 15/578,602, filed Nov. 30, 2017.
U.S. Appl. No. 15/578,617, filed Nov. 30, 2017.
U.S. Appl. No. 15/625,087, filed Jun. 16, 2017.
U.S. Appl. No. 15/632,004, filed Jun. 23, 2017.
U.S. Appl. No. 15/640,206, filed Jun. 30, 2017.
U.S. Appl. No. 15/738,043, filed Dec. 19, 2017.
U.S. Appl. No. 15/741,081, filed Dec. 29, 2017.
U.S. Appl. No. 15/861,257, filed Jan. 3, 2018.
U.S. Appl. No. 15/865,033, filed Jan. 8, 2018.
U.S. Appl. No. 15/942,242, filed Mar. 30, 2018.
U.S. Appl. No. 16/162,613, filed Oct. 17, 2018.
U.S. Appl. No. 16/194,007 filed Nov. 16, 2018.
U.S. Appl. No. 16/272,488, filed Feb. 11, 2019.
U.S. Appl. No. 16/448,988, filed Jun. 21, 2019.
U.S. Appl. No. 16/510,583, filed Jul. 12, 2019.
U.S. Appl. No. 16/552,215, filed Aug. 27, 2019.
U.S. Appl. No. 16/667,215, filed Oct. 29, 2019.

\* cited by examiner

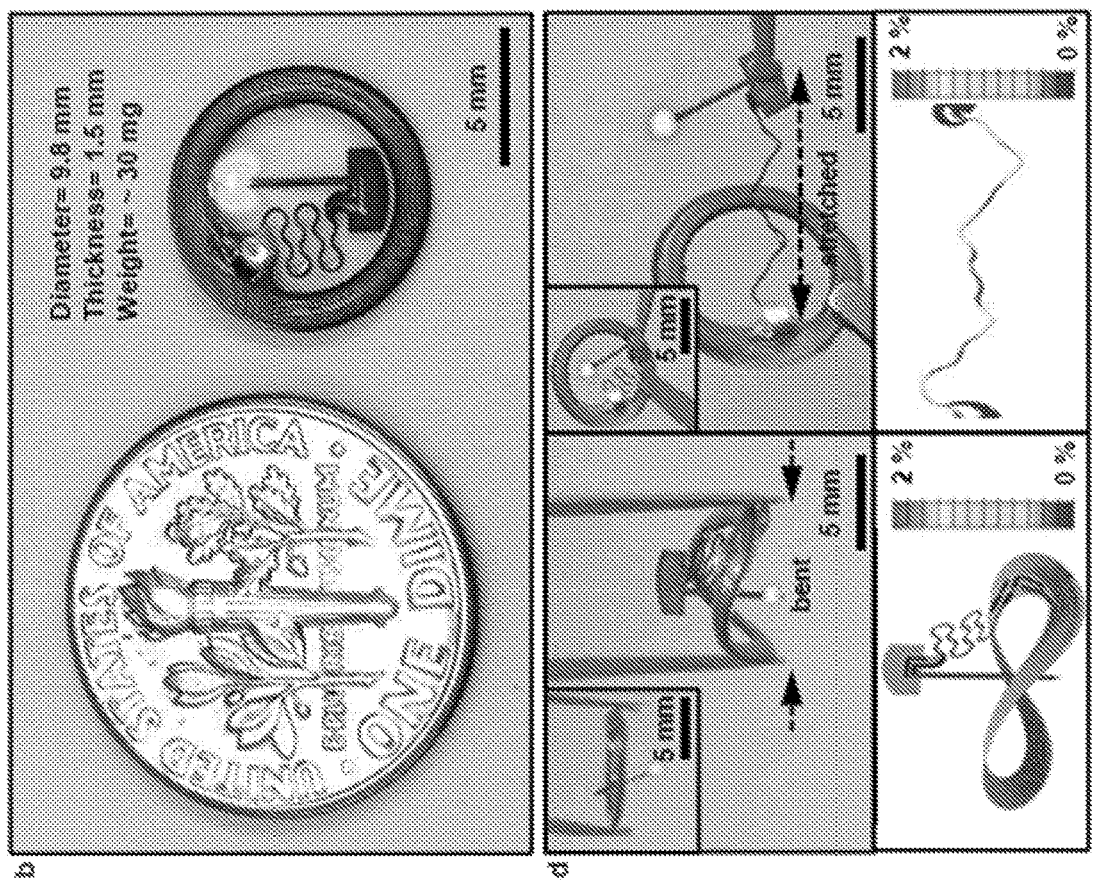
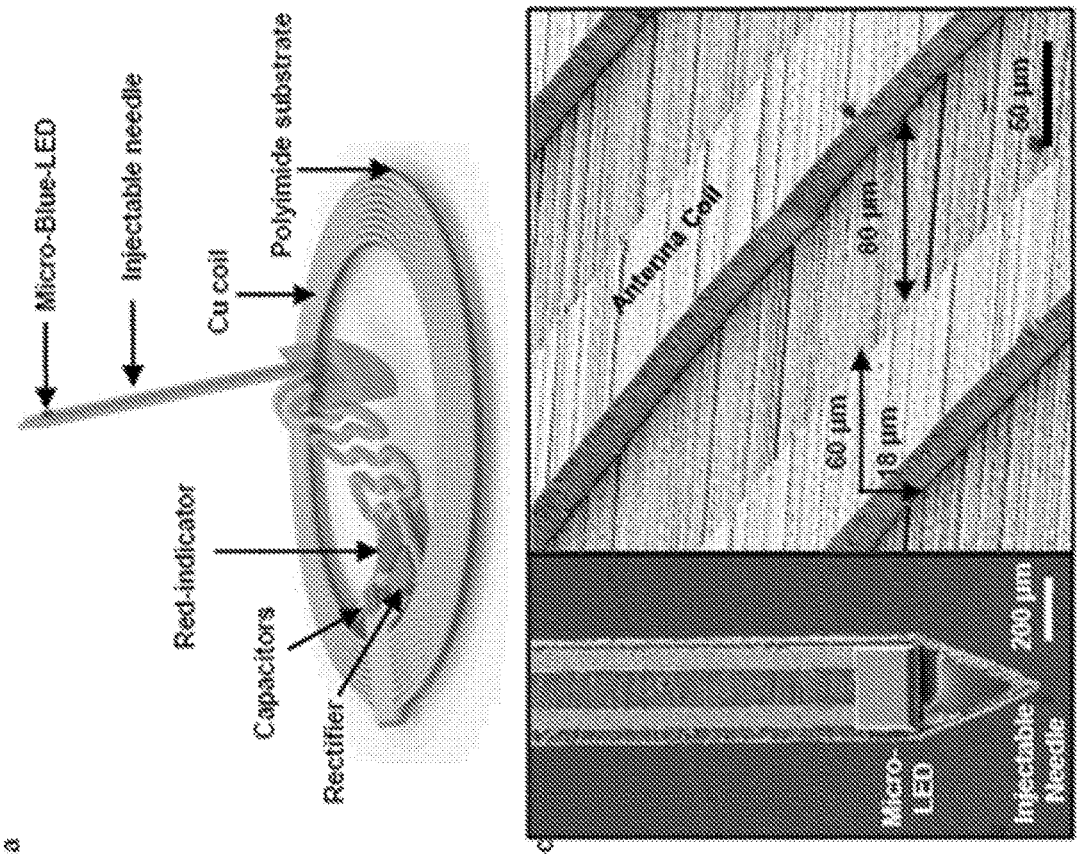
FIG. 1

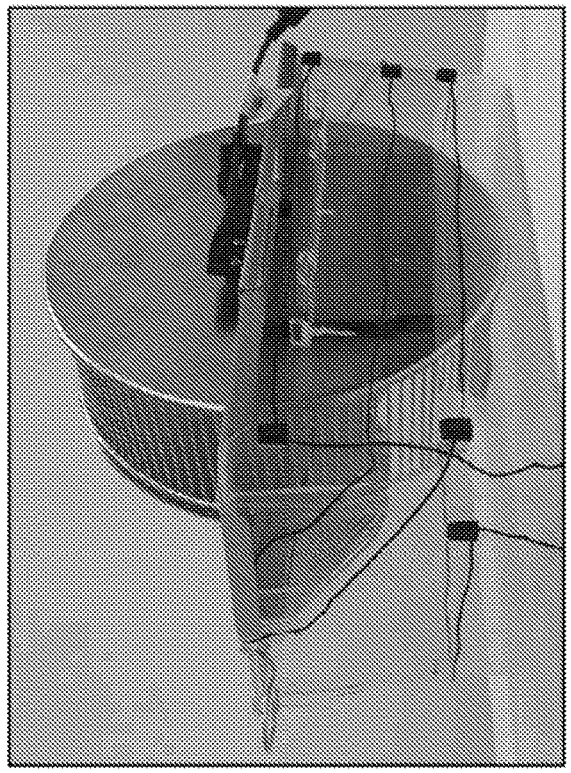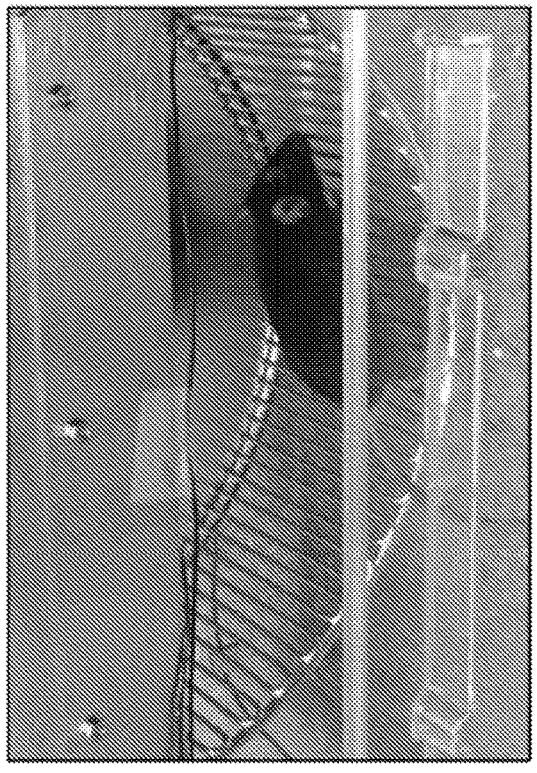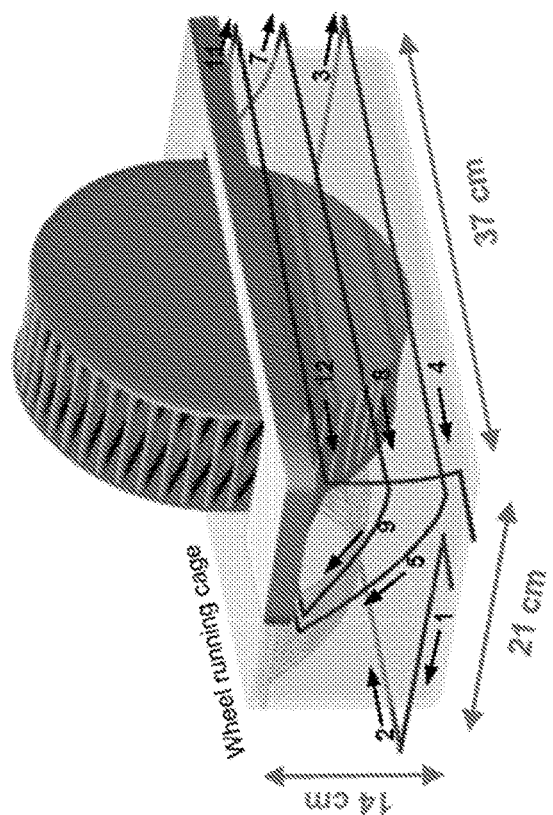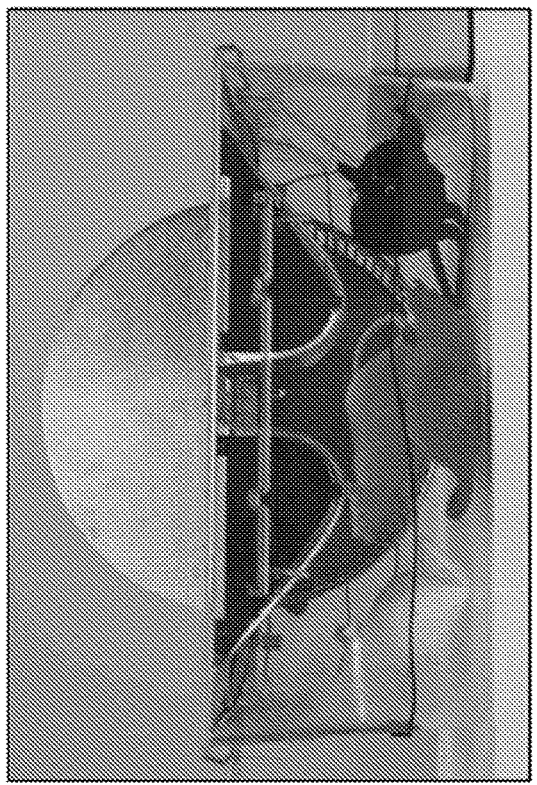
FIG. 16

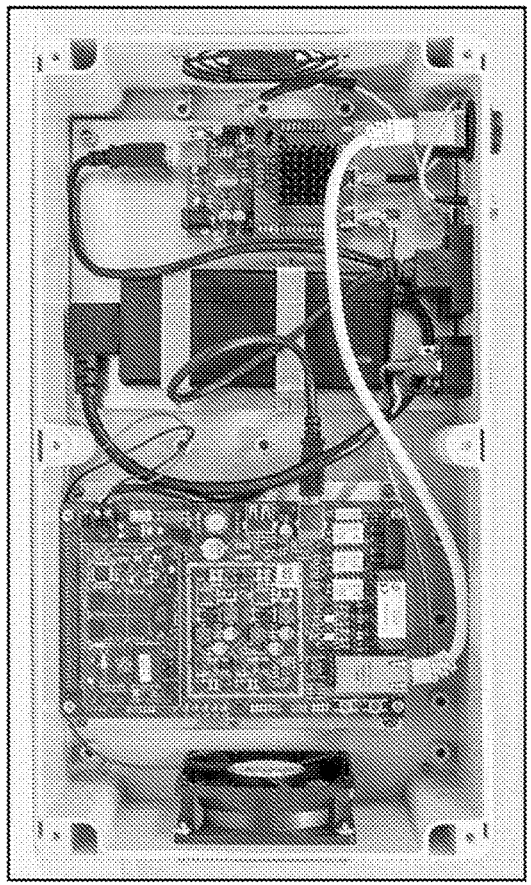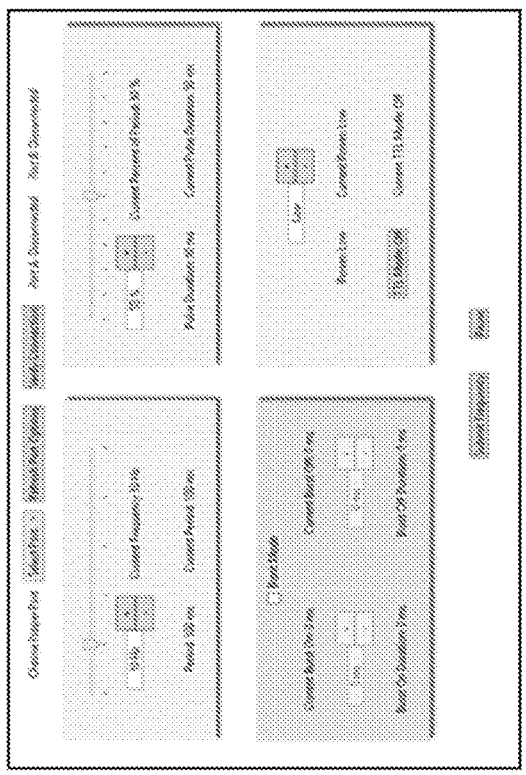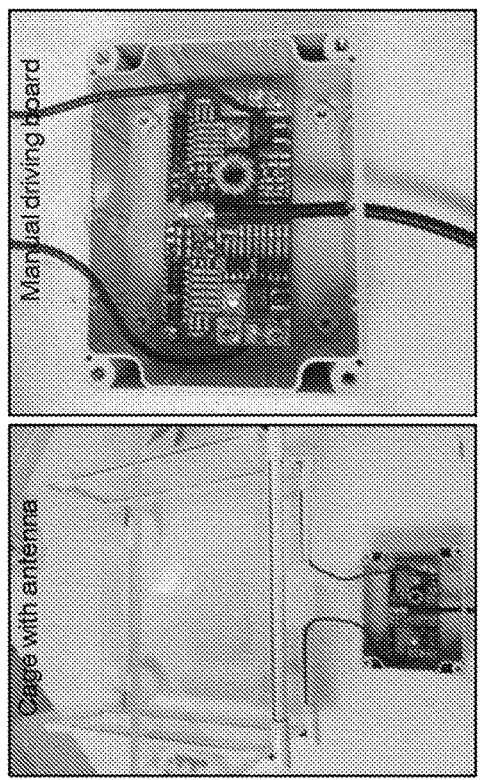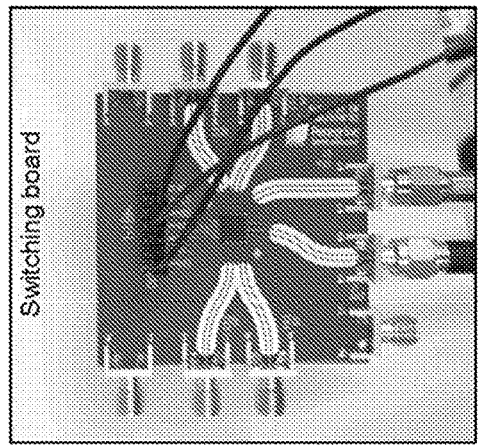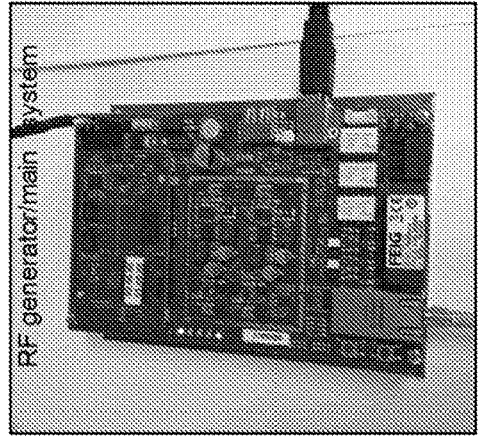
FIG. 17

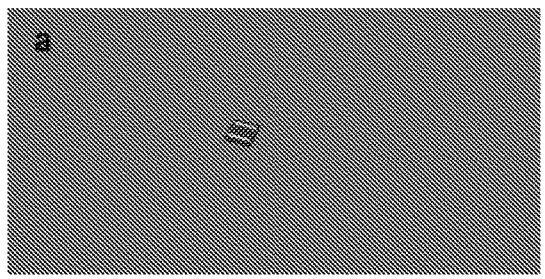
Transfer print a μ-IPD on a PI substrate
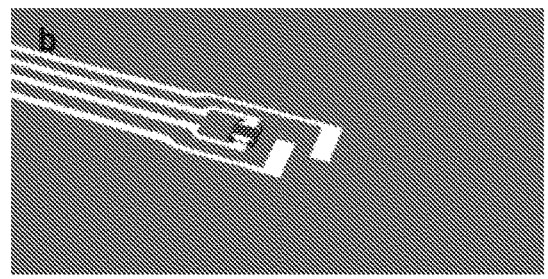
Deposition of metal interconnects
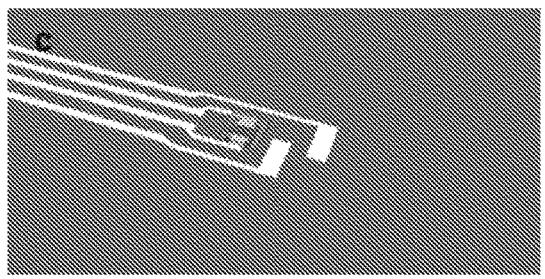
Pattern 7 μm thick SU-8 layer with absorber on top of the μ-IPD
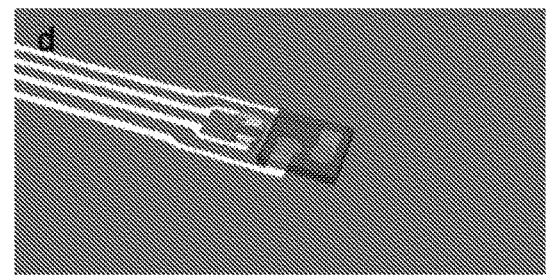
Transfer print and solder a μ-ILED next to the μ-IPD on top of interconnects
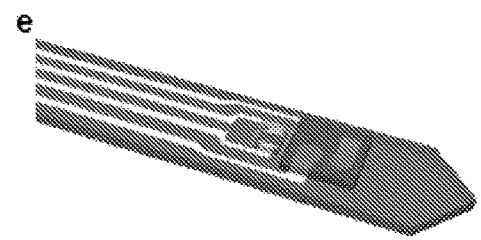
Laser cut the PI substrate with a needle pattern
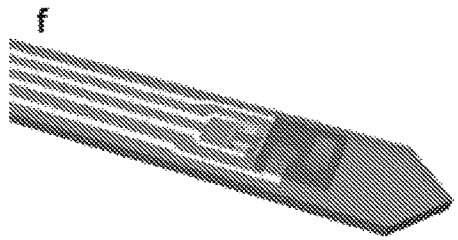
Encapsulate the probe with 3 μm thick PDMS
FIG. 38

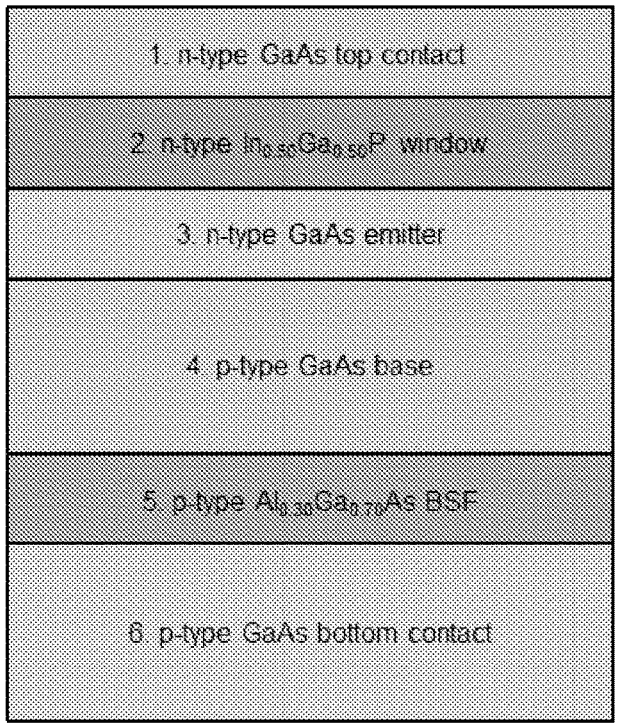

1. n-type GaAs top contact layer
   0.1 mm, Te-doped, $1\times10^{19}$ cm$^{-3}$
   0.1 mm, Si-doped, $2\times10^{18}$ cm$^{-3}$
2. n-type $In_{0.50}Ga_{0.50}P$ window layer
   0.025 mm, Si-doped, $2\times10^{18}$ cm$^{-3}$
3. n-type GaAs emitter layer
   0.1 mm, Si-doped, $2\times10^{18}$ cm$^{-3}$
4. p-type GaAs base layer
   2.5 mm, Zn-doped, $1\times10^{17}$ cm$^{-3}$
5. p-type $Al_{0.30}Ga_{0.70}As$ BSF layer
   0.1 mm, Zn-doped, $5\times10^{18}$ cm$^{-3}$
6. p-type GaAs bottom contact layer
   2 mm, Zn-doped, $3\text{-}5\times10^{19}$ cm$^{-3}$

FIG. 39

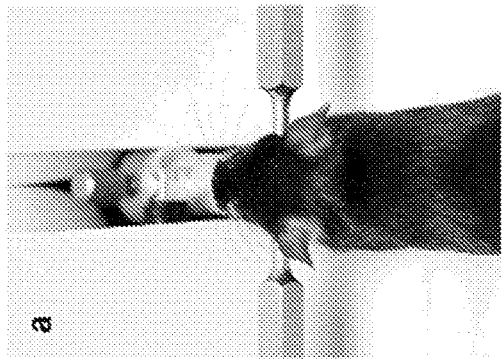
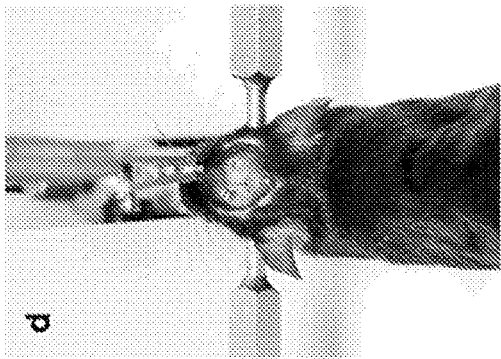
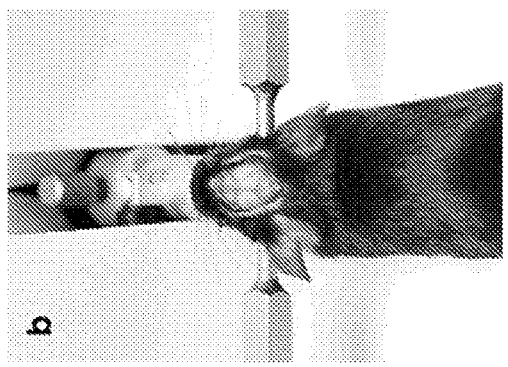
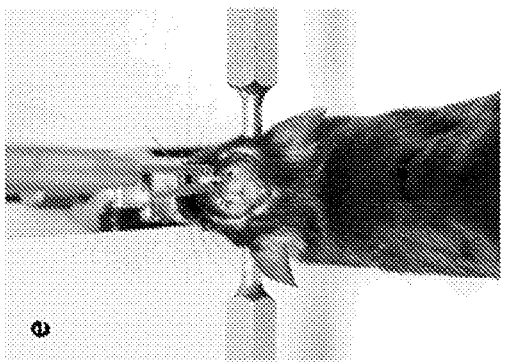
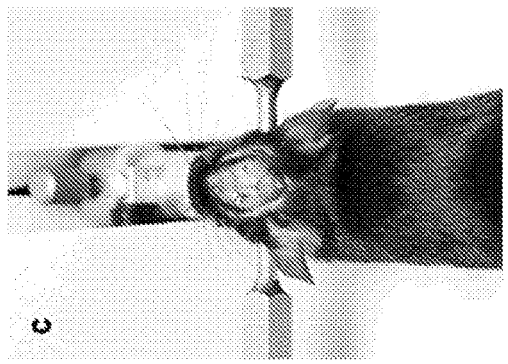
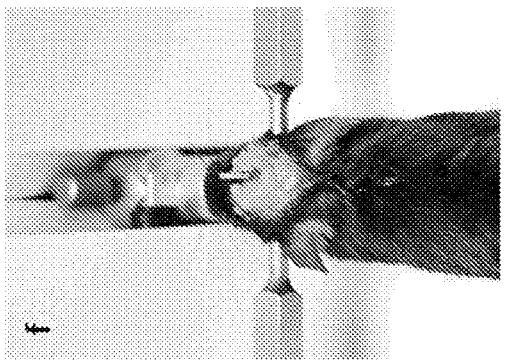
FIG. 55

IMPLANTABLE MEDICAL DEVICES FOR OPTOGENETICS

CROSS-REFERENCE TO RELATED APPLICATIONS

This application is a U.S. National Stage Application under 35 U.S.C. § of International Application No. PCT/US2017/025493, filed Mar. 31, 2017, which claims the benefit of and priority to U.S. provisional patent app. No. 62/316,708, filed Apr. 1, 2016, which is incorporated by reference herein in its entirety, except to the extent inconsistent herewith.

STATEMENT REGARDING FEDERALLY SPONSORED RESEARCH OR DEVELOPMENT

This invention was made with government support under TR01 NS081707 and EUREKA DA037152 awarded by the National Institutes of Health. The government has certain rights in the invention.

BACKGROUND OF INVENTION

Provided herein are devices for implantation into biological tissues and related methods. The devices and methods utilize electronic devices arranged in ultrathin functional layers, along with stacking of those functional layers in a special geometric configuration to achieve device implantation that is minimally invasive while providing the ability to interface with tissues on a cellular-scale resolution. Minimal disturbance of the tissue makes the devices particularly suitable for long-term implantation in biologically sensitive regions, including the brain.

Many conventional devices are designed for interfacing with a surface, such as biological tissue that is skin or an internal organ surface like the surface of the heart or the surface of the brain. An entirely different set of challenges arises when the application is for insertion into tissue. To accommodate a device within a tissue interior, surgery is generally required. Although improvements have been realized in the miniaturization of surgical instruments and devices, as well as arthroscopic techniques, there remains substantial tissue damage during the implantation procedure and, if necessary, device removal. Tissue damage associated with the relatively large size of conventional devices, including cannula and fiber optics, results in inflammation and risk of adverse events associated with an immune response. Provided herein are ultra-thin and mechanically compliant devices for implanting into and interfacing with biological tissue.

SUMMARY OF THE INVENTION

Provided herein are electronic devices specially configured for implantation, injection or surface mount into or onto various soft tissues, such as biological soft tissues in living animals. Ultrathin and mechanically compliant electronic device components, for example, permit access to the interior of living tissues without unduly impacting biologic function. Because the physical devices provided herein are minimally invasive, they can be used even for long-term implantation to interface with tissue that is not normally physically accessible. For example, devices provided herein may be injected into a tissue with an attendant impact that is no more than that caused by a micro-needle. Furthermore, the electronic devices can be sized to a cellular and subcellular scale, thereby providing precise monitoring and control of biologic function on a cell-by-cell basis. This provides unique and technologically sophisticated applications that are not achieved with conventional systems that are confined to tissue surfaces.

The devices and systems provided herein are further advantageous in that they are readily applied to target tissue, such as by a process analogous to needle insertion for delivery of materials to a patient's tissue. One difference is that instead of a chemical injection, certain embodiments of the systems described herein provide device injection. Such device injection avoids disadvantages in the art associated with tissue trauma when devices are implanted. For example, tissue trauma is associated with a robust immune response along with heightened risk of adverse events ranging from device rejection requiring device removal, to thrombi, lesions and the like that can affect the tissue. This is avoided herein by providing implantation that is functionally equivalent to, and no more traumatic than, micro-needle insertion. In some embodiments, for example, the thickness of the implanted device may ensure a minimum implantation footprint. Furthermore, the devices are amenable to providing multi-functionality, without unduly increasing device thickness or altering the device lateral dimension. Accordingly, any of the devices and methods provided herein is compatible with long-term implantation applications.

In an aspect, the present invention is an implantable biomedical device for interfacing with a target tissue, the device comprising a substrate; an electronic device supported by the substrate; and a freely positionable injectable needle electronically connected to the electronic device by a deformable interconnect; the injectable needle having one or more optical sources provided along a length of the injectable needle and/or near a distal tip end of the injectable needle; wherein each optical source is individually characterized by an emitting area less than or equal to $1\times10^5$ µm$^2$.

In an embodiment, the electronic device, the injectable needle and the deformable interconnect each comprise a thin film structure.

In an embodiment, the freely positionable injectable needle is moveable out of the plane of the electronic device. For example, in an embodiment, the freely positionable injectable needle is moveable in three dimensions or the freely positionable injectable needle is moveable within a substantially conical volume around a point defined by the intersection of the deformable interconnect and the electronic device, the length of the interconnect, and the length of the probe or needle.

In an embodiment, the implantable device is a millimeter-scale device. In an embodiment, the implantable device has a mass equal to or less than 1000 mg, or equal to or less than 500 mg, or equal to or less than 100 mg, or equal to or less than 30 mg. In an embodiment, the implantable device, the electronic device or both have open architectures.

In an embodiment, the electronic device comprises one or more of a coil, a rectifier, a capacitor and an optical indicator. For example, the coil may have an outer diameter less than or equal to 10 mm, 9.8 mm, 8 mm or 5 mm. In an embodiment, the electronic device has a thickness less than or equal to 5 mm, or less than or equal to 2 mm, or less than or equal to 1.5 mm. In an embodiment, the electronic device has a thickness selected from the range of 0.1 mm to 5 mm, 0.3 mm to 3 mm, 0.4 mm to 2 mm or 0.5 mm to 1.5 mm. In an embodiment, the electronic device is flexible with a radius of curvature greater than or equal to 10 mm, or greater than or equal to 7 mm, or greater than or equal to 4 mm or greater than or equal to 3 mm.

In an embodiment, the electronic device comprises one or more optical indicators each independently having an emitting area less than or equal to $1\times10^5$ μm², or less than or equal to $1\times10^4$ μm², or less than or equal to $1\times10^3$ μm². For example, the electronic device may comprise one or more optical indicators each independently having an emitting area selected from the range of $1\times10^3$ μm² to $1\times10^5$ μm² or area selected from the range of $1\times10^4$ μm² to $1\times10^5$ μm². In an embodiment, the optical indicator provides a radiant output characterized by a surface power density of 0.1 mW·mm⁻² to 500 mW·mm⁻², or 0.1 mW·mm⁻² to 150 mW·mm⁻², or 0.1 mW·mm⁻² to 50 mW·mm⁻². In an embodiment, the optical indicator provides a radiant output providing a change in the temperature of said target tissue equal to or less than 5° C., or equal to or less than 3° C., or equal to or less than 1° C. In an embodiment, the optical indicator emits electromagnetic radiation having a wavelength between 300 nm and 850 nm, or between 330 nm and 750 nm or between 390 nm and 650 nm.

In an embodiment, the injectable needle has a thickness less than or equal to 500 μm, or less than or equal to 300 μm, or less than or equal to 200 μm. In an embodiment, the injectable needle has a width less than or equal to 500 μm, or less than or equal to 350 μm. In an embodiment, the injectable needle has a length selected from a range of 0.1 mm to 10 mm, or 0.2 mm to 5 mm. In an embodiment, the injectable needle or a portion thereof is individually addressed to a cell or group of cells of said target tissue. In an embodiment, the injectable needle has a net bending stiffness greater than or equal to $1\times10^8$ GPa·μm⁴.

In an embodiment, the distal tip end of the injectable needle is tapered for insertion into the target tissue. In an embodiment, the distal end taper is to a pointed end having a lateral dimension selected from a range that is greater than or equal to 10 nm and less than or equal to 100 μm, or greater than or equal to 10 nm and less than or equal to 10 μm, or greater than or equal to 10 nm and less than or equal to 1 μm. In an embodiment, the distal end taper traverses a longitudinal distance that is less than 0.5 mm from the pointed end. In an embodiment, the distal end taper has a tissue-incident angle that is greater than or equal to 10° and less than or equal to 90° or greater than or equal to 30° and less than or equal to 70°.

In an embodiment, the electronic device comprises a coil, and the injectable needle and the deformable interconnect are disposed within an inner diameter of the coil.

In an embodiment, an implantable biomedical device further comprises a tab at an intersection of the injectable needle and the deformable interconnect for facilitating movement of the injectable needle in three dimensions.

In an embodiment, the deformable interconnect is flexible, stretchable or bendable. In an embodiment, the deformable interconnect has a serpentine, coiled or bent geometry. In an embodiment, the deformable interconnect is stretchable up to 100% or 200% or 300% without mechanical failure.

In an embodiment, the injectable needle comprises one or more optical sources each independently having an emitting area selected from the range of $1\times10^3$ μm² to $1\times10^5$ μm². In an embodiment, an optical source emits electromagnetic radiation having a wavelength between 300 nm and 800 nm, or between 330 nm and 750 nm, or between 390 nm and 650 nm. In an embodiment, an optical source is pulsed with a frequency selected from a range of 0.1 Hz to 1000 Hz or 1 Hz to 100 Hz and a duty cycle selected from a range of 0% to 100% or 0% to 50%. In an embodiment, an optical source provides a radiant output characterized by a surface power density of 0.1 mW·mm⁻² to 500 mW·mm⁻², or 0.1 mW·mm⁻² to 150 mW·mm⁻², or 0.1 mW·mm⁻² to 50 mW·mm⁻². In an embodiment, an optical source provides a radiant output providing a change in the temperature of said target tissue equal to or less than 2° C. or equal to or less than 1° C.

In an embodiment, the injectable needle comprises at least one photodetector, such as an inorganic photodetector. In an embodiment, the photodetector has a sensing area less than or equal to 1 mm², or less than or equal to 0.5 mm², or less than or equal to 0.1 mm². In an embodiment, the photodetector has a sensing area selected from the range of 5 μm² to 1 mm², or 10 μm² to 0.5 mm², or 20 μm² to 200 μm². In an embodiment, the photodetector is located within 1000 μm, or within 500 μm, or within 50 μm of at least one of the optical sources. In an embodiment, the photodetector comprises or is in optical communication with a narrow-band filter. For example, the photodetector may have a bandwidth, e.g., approximately 100 nm wide, that is centered at a wavelength between 300 nm and 1000 nm.

In an embodiment, the substrate comprises a material selected from the group consisting of polyimide and polyethylene terephthalate, and the substrate has a thickness selected from a range of 10 μm to 1000 μm, or 20 μm to 200 μm, or 25 μm to 100 μm.

In an embodiment, an implantable biomedical device further comprises an encapsulating material at least partially encapsulating the implantable device. In an embodiment, the encapsulating material is selected from the group consisting of poly(dimethylsiloxane), parylene-C, parylene-N, inorganic coatings and combinations of these. For example, an inorganic coating may be deposited by atomic layer deposition, physical vapor deposition, chemical vapor deposition or other methods.

In an embodiment, the device is implanted into a target tissue that is soft tissue of a living animal. In an embodiment, the target tissue is selected from the group consisting of brain, heart, kidney, liver, pancreas, bladder, lung, eye, blood vessel, nerve, muscle, spinal cord and skin.

In an aspect, a system comprises a plurality of implantable biomedical devices for interfacing with a target tissue, each of the implantable biomedical devices comprising: a substrate; an electronic device supported by the substrate; and a freely positionable injectable needle electronically connected to the electronic device by a deformable interconnect; wherein the injectable needle having one or more optical sources provided along a length of the injectable needle and/or near a distal tip end of the injectable needle; wherein each optical source is individually characterized by an emitting area less than or equal to $1\times10^5$ μm²; an antenna inductively coupled to a coil of each electronic device; and a photodiode for measuring optical output from an optical indicator of each electronic device.

In an aspect, a method of implanting the implantable biomedical device comprises the steps of positioning an implantable device adjacent to a soft tissue surface of a target tissue; inserting a freely positionable injectable needle into the soft tissue; and contacting the implantable device with the target tissue surface or an adjacent bone surface. In an embodiment, the contacting step comprises conformally contacting an encapsulating layer that at least partially encapsulates the electronic device with the target tissue surface or the bone surface. In an embodiment, the method of implanting further comprises a step of removing the substrate from the electronic device after contacting the implantable device with the target tissue surface or the bone surface.

In an aspect, a method of treating a biological tissue comprising at least one transformed cell comprises the steps of: implanting at least a portion of an implantable biomedical device into the biological tissue, thereby providing the implantable biomedical device in optical communication with the at least one transformed cell of the biological tissue; wherein the implantable biomedical device comprises: a substrate; an electronic device supported by the substrate; and a freely positionable injectable needle electronically connected to the electronic device by a deformable interconnect; wherein the injectable needle having one or more optical sources provided along a length of the injectable needle and/or near a distal tip end of the injectable needle; wherein each optical source is individually characterized by an emitting area less than or equal to $1 \times 10^5$ $\mu m^2$; and exposing the at least one transformed cell to an optical stimulus from the optical source; thereby treating the biological tissue. In an embodiment, the method further comprises a step of optically activating a therapeutic agent in contact with the biological tissue; thereby treating the biological tissue.

In an embodiment, exposing the at least one transformed cell to the optical stimulus from the implantable biomedical device increases or decreases expression of one or more light-responsive proteins. In an embodiment, the implantable device or one or more components thereof individually addresses one or more transformed cells of the biological tissue. In an embodiment, the at least one transformed cell of the biological tissue expresses photoactivatable proteins, receptors or channels. In an embodiment, the exposing step is carried out in vivo. In an embodiment, the transformed cell is a mammalian neuron or glial cell or a smooth muscle cell.

In an embodiment, the optical stimulus comprises exposure of the at least one transformed cell to one or more pulses of electromagnetic radiation. In an embodiment, each of the one or more pulses of electromagnetic radiation has an optical power density selected from the range of 0.1 mW·mm$^{-2}$ to 50 mW·mm$^{-2}$. In an embodiment, each of the one or more pulses of electromagnetic radiation has a wavelength selected from the range of 390 nm and 650 nm. In an embodiment, the one or more pulses of electromagnetic radiation are provided at a frequency selected from the range of 1 Hz and 100 Hz.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

Methods and systems of the instant invention are summarized in the embodiments below:

1. An implantable biomedical device for interfacing with a target tissue, said device comprising: a substrate; an electronic device supported by said substrate; and a freely positionable injectable needle electronically connected to said electronic device by a deformable interconnect; an optical source connected to said injectable needle; wherein said optical source has an emitting area less than or equal to $1 \times 10^6$ $\mu m^2$.

2. The device of claim 1, wherein said electronic device, said injectable needle and said deformable interconnect each comprise a thin film structure.

3. The device of any one of claims 1-2, wherein said freely positionable injectable needle is moveable out of a plane formed by the electronic device.

4. The device of any one of claims 1-3, wherein said freely positionable injectable needle is moveable in three dimensions.

5. The device of any one of claims 1-4, wherein said freely positionable injectable needle is moveable within a substantially conical volume around a point defined by the intersection of the deformable interconnect and the electronic device.

6. The device of any one of claims 1-5, wherein said implantable device is a millimeter-scale device.

7. The device of any one of claims 1-6, wherein said implantable device has a mass equal to or less than 1000 mg.

8. The device of any one of claims 1-7, wherein said implantable device has an open architecture.

9. The device of any one of claims 1-8, wherein said electronic device has an open architecture.

10. The device of any one of claims 1-9, wherein said electronic device comprises one or more of a coil, a rectifier, a capacitor and an optical indicator.

11. The device of claim 10, wherein said coil has an outer diameter less than or equal to 9.8 mm.

12. The device of any one of claims 1-11, wherein said electronic device has a thickness less than or equal to 5 mm.

13. The device of any one of claims 1-12, wherein said electronic device is flexible with a radius of curvature greater than or equal to 10 mm.

14. The device of any one of claims 1-13, wherein said electronic device comprises one or more optical indicators each independently having an emitting area less than or equal to $1 \times 10^6$ $\mu m^2$.

15. The device of any one of claims 1-13, wherein said electronic device comprises one or more optical indicators each independently having an emitting area selected from the range of $1 \times 10^3$ $\mu m^2$ to $1 \times 10^5$ $\mu m^2$.

16. The device of any one of claims 14-15, wherein said optical indicator provides a radiant output characterized by a surface power density of 0.1 mW·mm$^{-2}$ to 500 mW·mm$^{-2}$.

17. The device of any one of claims 14-16, wherein said optical indicator provides a radiant output during use selected to provide a change in temperature of said target tissue equal to or less than 5° C.

18. The device of any one of claims 14-17, wherein said optical indicator emits electromagnetic radiation having a wavelength between 300 nm and 850 nm.

19. The device of any one of claims 1-18, wherein said injectable needle has one or more of a thickness less than or equal to 500 $\mu m$, a width less than or equal to 500 $\mu m$, or a cross-sectional area less than or equal to 0.25 mm$^2$.

20. The device of any one of claims 1-19, wherein said injectable needle has a length selected from a range of 0.1 mm to 10 mm.

21. The device of any one of claims 1-20, wherein said injectable needle or a portion thereof is configured to individually address a cell or group of cells of said target tissue.

22. The device of claim 22, wherein at least one cell is a transformed cell and said optical source in use changes expression of one or more light-responsive proteins in said transformed cell.

23. The device of any one of claims 1-22, wherein said injectable needle has a net bending stiffness greater than or equal to $1 \times 10^8$ GPa·$\mu m^4$.

24. The device of any one of claims 1-23, wherein said injectable needle has a distal tip end that is tapered for insertion into said target tissue.

25. The device of claim 24, wherein said distal tip end taper is to a pointed end having a lateral dimension selected from a range that is greater than or equal to 10 nm and less than or equal to 100 μm.

26. The device of claim 24, wherein said distal end taper traverses a longitudinal distance that is less than 0.5 mm from the pointed end.

27. The device of claim 24, wherein said distal end taper has a tissue-incident angle during use that is greater than or equal to 10° and less than or equal to 90°.

28. The device of any one of claims 1-27, wherein said electronic device comprises a coil having an inner diameter, and said injectable needle and said deformable interconnect are disposed within said coil inner diameter.

29. The device of any one of claims 1-28, further comprising a tab at an intersection of said injectable needle and said deformable interconnect to facilitate controlled movement of said injectable needle in three dimensions.

30. The device of any one of claims 1-29, wherein said deformable interconnect is flexible, stretchable, bendable, or any combination thereof.

31. The device of any one of claims 1-30, wherein said deformable interconnect has a serpentine, coiled and/or bent geometry.

32. The device of any one of claims 1-31, wherein said deformable interconnect is configured to accommodate a strain of up to 100% without mechanical failure.

33. The device of any one of claims 1-32, wherein said optical source has an emitting area selected from the range of $1 \times 10^3$ μm$^2$ to $1 \times 10^5$ μm$^2$.

34. The device of claim 33, wherein said optical source emits electromagnetic radiation having a wavelength between 300 nm and 800 nm.

35. The device of any one of claims 33-34, wherein said optical source is pulsed with a frequency selected from a range of 0.1 Hz to 1000 Hz and a duty cycle selected from a range of 0% to 100%.

36. The device of any one of claims 33-35, wherein said optical source provides a radiant output characterized by a surface power density of 0.1 mW·mm$^{-2}$ to 500 mW·mm$^2$.

37. The device of any one of claims 33-36, wherein said optical source provides a radiant output during use selected to provide a change in temperature of said target tissue equal to or less than 2° C.

38. The device of any one of claims 1-37, wherein said injectable needle comprises at least one photodetector.

39. The device of claim 38, wherein said photodetector has a sensing area less than or equal to 1 mm$^2$.

40. The device of claim 38, wherein said photodetector has a sensing area selected from the range of 5 μm$^2$ to 1 mm$^2$.

41. The device of claim 38, wherein said photodetector is located within 1000 μm of at least one of said optical sources.

42. The device of claim 38, wherein said photodetector is an inorganic photodetector.

43. The device of claim 38, wherein said photodetector has a 100 nm-wide bandwidth centered between 300 nm and 1000 nm.

44. The device of any one of claims 1-43, wherein said substrate comprises a material selected from the group consisting of polyimide and polyethylene terephthalate, and wherein said substrate has a thickness selected from a range of 10 μm to 1000 μm.

45. The device of any one of claims 1-44, further comprising an encapsulating material at least partially encapsulating said implantable device.

46. The device of claim 45, wherein said encapsulating material is selected from the group consisting of poly (dimethylsiloxane), parylene-C, parylene-N, inorganic coatings and combinations of these.

47. The device of any one of claims 1-46, wherein said target tissue is soft tissue of a living animal.

48. The device of claim 47, wherein said target tissue is selected from the group consisting of brain, heart, kidney, liver, pancreas, bladder, lung, eye, blood vessel, nerve, muscle, spinal cord and skin.

49. The device of any of claims 1-48, further comprising a plurality of optical sources provided along a length of said injectable needle.

50. The device of any of claims 1-49, wherein said injectable needle has a distal tip end and said optical source is positioned adjacent to said distal tip end.

51. The device of claim 50, wherein said optical source is positioned within 1 mm from said distal tip end.

52. A system comprising: a plurality of implantable biomedical devices for interfacing with a target tissue, each of said implantable biomedical devices comprising: a substrate; an electronic device supported by said substrate; a freely positionable injectable needle electronically connected to said electronic device by a deformable interconnect; an optical source connected to said injectable needle; wherein said optical source has an emitting area less than or equal to $1 \times 10^6$ μm$^2$; an antenna inductively coupled to a coil of each electronic device; and a photodiode for measuring light emitted or scattered from said target tissue.

53. A method of implanting the implantable biomedical device of any of claims 1-51, the method comprising the steps of: positioning said implantable device adjacent to a soft tissue surface of said target tissue; inserting said freely positionable injectable needle into said soft tissue; and contacting said implantable device with said target tissue surface or an adjacent bone surface.

54. The method of claim 53, wherein said contacting step comprises conformally contacting an encapsulating layer that at least partially encapsulates said electronic device with said target tissue surface or said bone surface.

55. The method of claim 53, further comprising a step of removing said substrate from said electronic device after contacting said implantable device with said target tissue surface or said bone surface.

56. An implantable optical system for optically interfacing with a target tissue, said device comprising: a substrate; an electronic device supported by said substrate; said electronic device comprising a wireless system providing for wireless power and data communication; and an injectable optical probe electronically connected to the electronic device; wherein the optical probe comprises one or more optical sources and one or more optical detectors optically collocated along a length and/or near a distal end; wherein each optical source is individually characterized by lateral dimensions equal to or less than 1000 μm and wherein each optical detector is individually characterized by lateral dimensions equal to or less than 1000 μm; wherein said wireless system at least partially powers said one or more optical sources and one or more optical detectors.

57. The implantable optical system of claim 56, wherein said injectable optical probe is electronically connected to the electronic device by a stretchable electrical interconnect.

58. The implantable optical system of one any of claims 56-57, wherein said injectable optical probe is electronically connected to the electronic device by a flexible electrical interconnect.

59. The implantable optical system of any one of claims 56-58, wherein said injectable optical probe is a freely positionable structure.

60. The implantable optical system any one of claims 56-59, wherein said injectable optical probe is a filamentary structure.

61. The implantable optical system of claim 60, wherein said filamentary structure is a needle.

62. The implantable optical system of claim 61, wherein said filamentary structure is characterized by an average thickness less than or equal to 1000 µm.

63. The implantable optical system of any one of claims 56-62, wherein said one or more optical sources and one or more optical detectors are provided in a stacked configuration on said optical probe.

64. The implantable optical system of any one of claims 56-63, wherein each optical source is individually characterized by an emitting area less than or equal to $1\times10^5$ µm$^2$.

65. The implantable optical system of any one of claims 56-64, wherein each optical source is individually characterized by emitted electromagnetic radiation having wavelengths selected over the range of 300 nm to 1400 nm.

66. The implantable optical system of any one of claims 56-65, wherein each optical source is individually characterized by a radiant output characterized by a surface power density of 0.1 mW mm$^{-2}$ to 10 mW mm$^{-2}$.

67. The implantable optical system of any one of claims 56-66, wherein at least a portion of said optical sources is configured to excite fluorescence or scattered light from said tissue.

68. The implantable optical system of any one of claims 56-67, wherein each optical detector is individually characterized by an active detection area less than or equal to $1\times10^5$ µm$^2$.

69. The implantable optical system of any one of claims 56-68, further comprising one or more optical dispersion elements positioned to optically disperse electromagnetic radiation scattered by or emitted from said tissue prior to detection by said one or more optical detectors.

70. The implantable optical system of any one of claims 56-69, further comprising one or more optical filters positioned to optically filter electromagnetic radiation scattered by or emitted from said tissue prior to detection by said one or more optical detectors.

71. The implantable optical system of any one of claims 56-70, wherein said wireless element provides for wireless control of said optical system.

72. The implantable optical system of any one of claims 56-71, wherein said wireless element provides for wireless data transfer into and out of said optical system.

73. The implantable optical system of any one of claims 56-72, wherein said wireless element comprises one or more magnetic loop antenna.

74. The implantable optical system of any one of claims 56-73, wherein said wireless element comprises a NFC chip device.

75. The implantable optical system any one of claims 56-74, wherein said wireless element comprises one or more magnetic loop antenna and a NFC chip device; wherein said magnetic loop antenna are provided in a geometry surrounding said NFC chip device and configured to a least partially power said NFC chip device.

76. The implantable optical system of any one of claims 56-75, further comprising an external reader for power transfer and data collection.

77. The implantable optical system of any one of claims 56-76, wherein at least a portion of said electronic device, injectable optical probe or both is encapsulated in a barrier layer.

78. The implantable optical system of any one of claims 56-77 comprising an injectable photometer.

79. The implantable optical system of any one of claims 56-78 comprising an injectable fluorescence imaging system.

80. A method of using an implantable optical system for optically interfacing with a target tissue, said method comprising: providing an implantable optical system comprising: a substrate; an electronic device supported by said substrate; said electronic device comprising a wireless system providing for wireless power and data communication; and an injectable optical probe electronically connected to the electronic device via a deformable interconnect; wherein the injectable optical probe comprises one or more optical sources and one or more optical detectors optically collocated along a length and/or near a distal end; wherein each optical source is individually characterized by lateral dimensions equal to or less than 1000 µm and wherein each optical detector is individually characterized by lateral dimensions equal to or less than 1000 µm; wherein said wireless system at least partially powers said one or more optical sources and one or more optical detectors; inserting said injectable optical probe into said target tissue; and sensing and/or actuating said target tissue with said one or more optical sources and/or said one or more optical detectors.

81. A method of using an implantable biomedical device for interfacing with a target tissue, the method comprising: providing said implantable biomedical device comprising; a substrate; an electronic device supported by said substrate; and a freely positionable injectable needle electronically connected to the electronic device by a deformable interconnect; said injectable needle having one or more optical sources provided along a length of said injectable needle and/or near a distal tip end of said injectable needle; wherein each optical source is individually characterized by an emitting area less than or equal to $1\times10^6$ µm$^2$; inserting said freely positionable injectable needle into said target tissue; and actuating said target tissue with said one or more optical sources.

82. An implantable biomedical device for interfacing with a target tissue, said device comprising: a substrate; an electronic device supported by said substrate; and a freely positionable probe electronically connected to the electronic device by a deformable interconnect; said probe having one or more optical sources provided along a length of said probe and/or near a distal tip end of said probe; wherein each optical source is individually characterized by an emitting area less than or equal to $1\times10^6$ µm$^2$.

83. The implantable biomedical device of claim 82, configured for use with said target tissue selected from the group consisting of spinal cord, peripheral nerves, heart, and a blood vessel.

84. The implantable biomedical device of claim 82, wherein said freely positionable probe is configured for controlled positioning of said one or more optical sources in or adjacent to said target tissue during use.

85. The implantable biomedical device of claim 84, wherein said target tissue is deep brain tissue and said probe comprises an injectable needle.

86. The implantable biomedical device of any of claim 49, wherein the plurality of optical sources corresponds to at least two different colors and the electronic device provides independent control of each optical source color.

87. The implantable biomedical device of any of claims 1-51 and 86, further comprising a second freely positionable injectable needle electronically connected to said electronic device by a second deformable interconnect.

88. The implantable biomedical device of claim 87 having independent control of each injectable needle, wherein said implantable biomedical device is configured for use as a bilateral implant.

89. The implantable biomedical device of claim 88, configured for use in brain tissue.

90. A multiplexed implantable biomedical device comprising two or more of the implantable biomedical devices of any of claims 1-51, 86-89.

91. The multiplexed implantable biomedical device of claim 90, configured for use in a plurality of animals or a single animal.

100. The multiplexed implantable biomedical device of claim 91, comprising three or more channels, wherein each channel corresponds to an individual implantable biomedical device, an individual optical source color, or both.

BRIEF DESCRIPTION OF THE DRAWINGS

FIG. 1. Designs and operational features of a thin, flexible, millimeter scale wireless device for programmed delivery of light into biological tissues for experiments in optogenetics. A) Schematic illustration of the overall construction, highlighting a freely positionable needle with a μ-ILED at the tip end, connected to a receiver coil with matching capacitors, a rectifier and a separate μ-ILED indicator. B) Picture of a completed device (diameter ~9.8 mm) next to a US dime (diameter 17.91 mm) for size comparison. C) Scanning electron microscope images of an injectable needle with LED and 8 turns coil trace with the dimension of 60 μm width, 18 μm thickness and 80 μm spacing, colorized to highlight the different components (blue: μ-ILED; yellow: polyimide; orange: copper) Images and corresponding finite element modeling results of the device before and after bending (left) the body of the device and stretching (right) the serpentine connection to the injectable needle, respectively.

FIG. 16. A-B) Loop design on the metal running wheels. Wireless operation of LED devices attached on C) dummy mice and implanted on D) real mouse.

FIG. 17. Customized near field wireless system and software UI.

FIG. 38 summarizes process steps for fabricating a photometer probe. (a) Transfer print a μ-IPD onto a 75 μm thick PI substrate. (b) Pattern metal interconnects. (c) Pattern 7 μm thick absorber layer on top of the μ-IPD. (d) Transfer print and solder a μ-ILED on the PI substrate. (e) Define the needle structure by laser cutting. (f) Encapsulate the injectable needle with PDMS.

FIG. 39 illustrates a representative GaAs photodetector stack design.

FIG. 55 Surgery process. (a) The anesthetized mouse is head-fixed on the stereotax. (b) Fur is razed and skin is cut and opened with scalpel. (c) A hole is opened with a drill bit for probe implant, and a screw is driven into the other side of skull as support. (d) Device is delivered by a holder upon the hole. (e) Slowly low down the probe until get BLA region set by the coordinates. (f) Superglue is used to attach the device, skull and the supportive screw. Then dental cement is applied to build up a cup for further securing and protection.

DETAILED DESCRIPTION OF THE INVENTION

Figure 2:
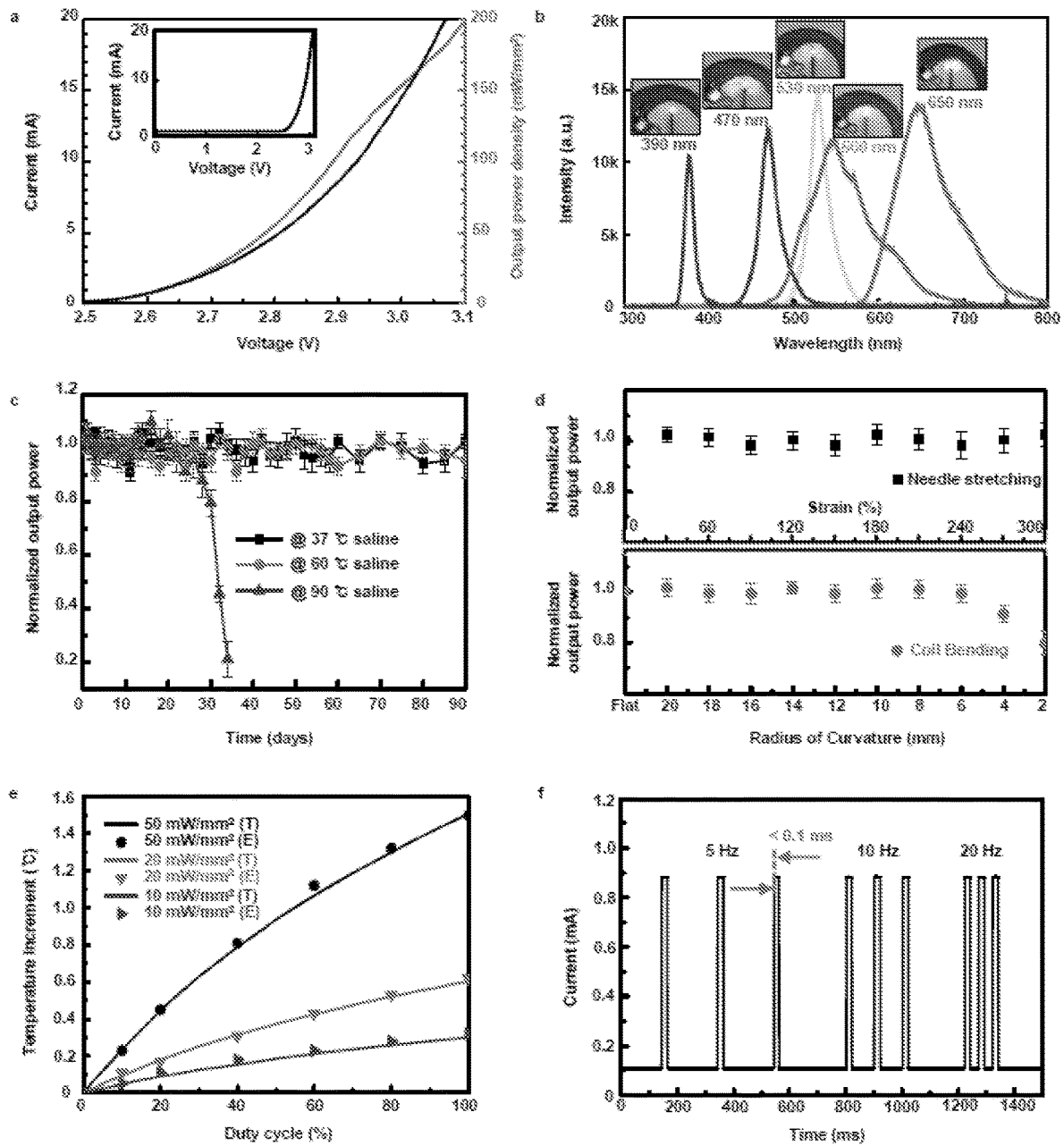
FIG. 2. Electrical, optical, mechanical, and thermal properties. A) Current-Voltage-Light output characteristics. B) Emission spectra associated with operation of devices built with different μ-ILEDs. C) Normalized optical power density as a function of time after immersion of devices in warm saline solutions with temperatures of 37, 60 and 90° C. D) Normalized optical power density as a function of extension of the serpentine interconnect to the injectable needle (top) and of the bending radius of the body of the device (bottom). E) Change in temperature adjacent to an operating μ-ILED (T: Theoretical, for the case of brain tissue; E: Experimental, for the case of a hydrogel) as a function of duty cycle of operation at different peak output power densities (10, 20 and 50 mW·mm$^{-2}$). F) Current output from a photodiode placed adjacent to a μ-ILED operating at different pulse frequencies (5, 10 and 20 Hz), for a fixed duration of 20 ms. The rise and fall times are ~0.1 ms.

In general, the terms and phrases used herein have their art-recognized meaning, which can be found by reference to standard texts, journal references and contexts known to those skilled in the art. The following definitions are provided to clarify their specific use in the context of the invention.

"Implantable" refers to a device that is inserted into tissue, such as for interfacing with an interior portion of tissue that is not surface-accessible. "Interfacing" refers to measuring and/or controlling one or more parameters associated with the target tissue. For example, a physical parameter such as temperature or electrical potential may be measured and/or controlled. Similarly, a biological parameter, such as concentration of a biologic material, cell surface receptor blocking/activation, membrane porosity, may be measured and/or controlled. Accordingly, interfacing is used broadly to refer to passive measurement of a tissue or cell property, active control of a tissue or cell property, or both.

"Target tissue" refers to a tissue in which the device is implanted and, more specifically, a specific portion of tissue for which interfacing is desired. Target tissue is used broadly to refer to an interior region of tissue that is beneath a tissue surface and so is not visually or physically accessible without opening up the tissue. Target tissue may refer to a plurality of cells defined over an interfacing surface area. Alternatively, target tissue may be a single cell, and even components thereof. For example, parameters associated with individual cells may be accessed by configuring the device components and functional devices to correspond to the size of individual cells and also for device positioning so that the functional electronic device is adjacent to an individual cell. Relevant components include cell portions, such as nuclei, mitochondria, and cell surface receptors.

Arrays of functional electronic devices, including by stacked functional layers or by arrays within an individual layer, facilitate multiple interfacing with different physical parameters, and/or along a plurality of positions within the target tissue, such as a plurality of cells. For example, individual neurons or networks of neurons may be monitored at distinct locations, along with actuators for selectively turning on or blocking neurons at other locations.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbounded components or portions of a component, in contrast, are capable of substantial movement relative to the substrate. In an embodiment, the invention provides devices wherein one or more inorganic semiconductor components, one or more metallic conductor components and/or one or more dielectric components are directly or indirectly bonded to the substrate, for example, via a bonding layer or an adhesive layer. The direct bonding to the substrate may also include components that are embedded, either partially or completely, in the substrate.

"Freely positionable" refers to a property of an object that is capable of permanent or temporary spatial displacement, especially spatial displacement relative to a coincident or proximate object, such as a coincident or proximate object to which the freely positionable object is physically connected. A freely positionable object is capable of being at least partially displaced, repositioned, moved or relocated from a starting position to one or more alternate positions. In an embodiment, a freely positionable object may pivot, rotate or bend. In an embodiment, the freely positionable object is moveable completely or partially out of the plane of its starting position. For example, a freely positionable object may be moveable in three dimensions, such as three dimensions defined by a substantially conical volume around a substantially fixed point. Aspects of the invention relate to freely positionable objects such as injectable needles or probes that may be fabricated in the plane of an implantable device, but which may be spatially displaced to allow for insertion into a target tissue.

"Optically collocated" refers to a configuration of at least one optical source and at least one optical detector positioned relative to each other such that upon optical excitation of an environment by the optical source(s), such as on or within a target tissue, the optical detector(s) is capable of receiving at least a portion of scattered or emitted electromagnetic radiation from the target tissue, thereby providing useful information or characterization of the target tissue.

"Stacked configuration" refers to an arrangement of various layers and substrates having coincident surface areas, with adjacent layers or substrates positioned on top of each other. In this manner, multiple functionality can be achieved by stacking multiple functional layers on top of each other, without adversely affecting the device form factor or packaged shape. For example, use of ultra-thin functional layers ensures a stacked device remains extremely thin. This is advantageous for insertion into tissue as well as minimizing tissue disturbance area after insertion. Importantly, the ultra-thin layout ensures that the interfacing with the target tissue is precisely confined to an interfacing area that can be extremely small, such as corresponding to the cellular scale, even for multiple functional layers.

As used herein, "lateral dimensions" refer to dimensions perpendicular to the thickness dimension, and optionally dimensions parallel to a surface of the substrate. Lateral dimensions include, for example, length and width dimensions. In embodiments, the term "thickness" refers to a dimension of a component perpendicular to a supporting substrate.

"Functional layer" refers to a layer that imparts some functionality to the device. For example, the functional layer may contain semiconductor components, metallic components, dielectric components, optical components, piezoelectric components, etc. that form an electronic device. A "functional electronic device" refers to an electronic device, such as a sensor or actuator that interfaces with tissue in which the device is implanted. The functional layer may comprise multiple layers, such as multiple semiconductor layers, metallic layers or dielectric layers separated by support layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of a neutral mechanical plane within a multi-layer device to thereby increase the bendability or deformability of the device.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $LaO_7CaO_3MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors.

Other components include, but are not limited to, thin film transistors (TFTs), transistors, diodes, electrodes, integrated circuits, circuit elements, control elements, photovoltaic elements (e.g. solar cell), sensors, light emitting elements, actuators, piezoelectric elements, receivers, transmitters, microprocessors, transducers, islands, bridges and combinations thereof. Components may be connected to one or more contact pads as known in the art, such as by metal evaporation, wire bonding, and application of solids or conductive pastes, for example. Electronic devices of the invention may comprise one or more components, optionally provided in an interconnected configuration.

"Taper" refers to a shape of one end of a device, including layers thereof, that decreases from a maximum lateral dimension. In an aspect the taper is to a distal-most (relative to the tissue surface) end of a substrate having a minimal lateral dimension. In an aspect, the minimal lateral dimension at the distal-most end is a point tip. Such a taper is an advantageous feature to facilitate tissue insertion while minimizing damage during insertion and removal in a similar manner to application of a needle into a tissue for injection of drugs, vaccines or fluids into a patient. For aspects where the tip end has a visible end that is flat, the tissue-incident angle is measured from an imaginary vertex point where the lines formed by the substrate edges intersect. In general, the smaller the angle the lower the trauma to tissue during insertion, with a balance against the length of the distal end taper, with smaller angles requiring longer taper lengths.

"Neutral mechanical plane" (NMP) refers to an imaginary plane existing in the lateral, b, and longitudinal, l, directions of a device. The NMP is less susceptible to bending stress than other planes of the device that lie at more extreme positions along the vertical, h, axis of the device and/or within more bendable layers of the device. Thus, the position of the NMP is determined by both the thickness of the device and the materials forming the layer(s) of the device. In an embodiment, a device of the invention includes one or more inorganic semiconductor components, one or more metallic conductor components or one or more inorganic semiconductor components and one or more metallic conductor components provided coincident with, or proximate to, the neutral mechanical plane of the device.

"Coincident" refers to the relative position of two or more objects, planes or surfaces, for example a surface such as a neutral mechanical plane that is positioned within or is adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element when the device is conformed to a tissue surface.

"Electronic device" generally refers to a device incorporating a plurality of components, and includes large area electronics, printed wire boards, integrated circuits, component arrays, biological and/or chemical sensors, physical sensors (e.g., temperature, strain, etc.), nanoelectromechanical systems, microelectromechanical systems, photovoltaic devices, communication systems, medical devices, optical devices and electro-optic devices. An electronic device may sense a property of the target tissue and/or may control a property of the target tissue.

"Sensing" and "sensor" refers to a functional electronic device or device component useful for detecting the presence, absence, amount, magnitude or intensity of a physical, biological state, and/or chemical property. Useful electronic device components for sensing include, but are not limited to electrode elements, chemical or biological sensor elements, pH sensors, temperature sensors, strain sensors, mechanical sensors, position sensors, optical sensors and capacitive sensors. Useful functional electronic devices include various device components operably arranged to provide electrodes for detecting adjacent electric potential, sensors for detecting a biological condition (e.g., disease state, cell type, cell condition) or a chemical, pH, temperature, pressure, position, electromagnetic radiation (including over desired wavelengths such as associated with a fluorescent dye injected into tissue), electric potential.

"Actuating" and "actuator" refers to a functional electronic device or device component useful for interacting with, stimulating, controlling, or otherwise affecting an external structure, material or fluid, for example a target tissue that is biological tissue. Useful actuating elements include, but are not limited to, electrode elements, electromagnetic radiation emitting elements, light emitting diodes, lasers and heating elements. Functional electronic devices include actuators that are electrodes for providing a voltage or current to a tissue and sources of electromagnetic radiation for providing electromagnetic radiation to a tissue, such as LEDs. Actuators also include ablation sources for ablating tissue, thermal sources for heating tissue, displacement sources for displacing or otherwise moving a tissue, fluid reservoirs, such as reservoirs of biologics or chemicals for releasing biologics or chemicals to affect biological function, such as a biological response including cell death, cell proliferation, or cell therapy by application of biologics or chemicals.

"Removable adhesive layer" and "releasable adhesive layer" are used interchangeably to refer to a material that is physically and/or chemically removed under pre-selected or predetermined conditions such as conditions of time, pressure, temperature, chemical or biological composition, and/or electromagnetic radiation. In an embodiment, for example, a releasable adhesive layer is removed via a processes selected from the group consisting of decomposition, disintegration, dissolution, hydrolysis, resorption, bioresporption, photodecomposition, and depolymerization, optionally at a preselected time or at a preselected rate or in response to a preselected set of conditions or change in conditions. In an embodiment, for example, a selectively removable material is removed by undergoing a phase change, such as melting or sublimation, resulting in loss or relocation of the material, optionally at a preselected time or at a preselected rate or in response to a preselected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, electronic conditions. When the releasable adhesive layer of a transient electronic device is exposed to the condition(s) that initiate removal of the material, the releasable adhesive layer may be substantially completely removed, completely removed or incompletely removed at a "pre-selected time" or at a "pre-selected rate". A selectively removable material that is "substantially completely" removed is 95% removed, or 98% removed, or 99% removed, or 99.9% removed, or 99.99% removed, but not completely (i.e., 100%) removed.

"Bioresorbable" refers to a material that is susceptible to being chemically broken down into lower molecular weight chemical moieties by reagents that are naturally present in a biological environment. In an in-vivo application, the chemical moieties may be assimilated into human or animal tissue. A bioresorbable material that is "substantially completely" resorbed is highly resorbed (e.g., 95% resorbed, or 98% resorbed, or 99% resorbed, or 99.9% resorbed, or 99.99% resorbed), but not completely (i.e., 100%) resorbed. In some embodiments, the invention provides bioresorbable devices, devices or selected portions of the device that are bioresorbable, such as adhesive layers, substrates, encapsulating layers, or barrier layers.

"Biocompatible" refers to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a biocompatible material is implanted into a human or animal. Alternatively, immune response may be determined histologically, wherein localized immune response is assessed by visually assessing markers, including immune cells or markers that are involved in the immune response pathway, in and adjacent to the implanted device. In an aspect, a biocompatible device does not observably change immune response as determined histologically. In some embodiments, the invention provides biocompatible devices configured for long-term implantation, such as on the order of weeks to months, without invoking an adverse immune response. The implantation does contemplate some immune response as may occur for any minimally invasive procedures, such as needle insertion into tissue, so long as the immune response is locally confined, transient and does not lead to large-scale inflammation and attendant deleterious effects.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal. In some embodiments, the invention provides bioinert devices.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component). In this manner, a delivery substrate may be described as indirectly supporting a device component through intermediate components corresponding to an adhesive layer and a substrate.

"Island" refers to a relatively rigid component of an electronic device comprising a plurality of semiconductor components. "Bridge" refers to structures interconnecting two or more islands or one island to another component. Specific bridge structures include semiconductor and metallic interconnects. In an embodiment, a device of the invention comprises one or more semiconductor-containing island structures, such as transistors, electrical circuits or integrated circuits, electrically connected via one or more bridge structures comprising electrical interconnects. The bridge structures may be wavy (connected to wavy substrate), serpentine (in plane curvature) and/or in a pop-up (out of plane curvature) configuration.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure is surrounded by one or more structures. "Completely encapsulated" refers to the orientation of one structure such that it is completely surrounded by one or more other structures. The invention includes devices having partially or completely encapsulated inorganic semiconductor components, metallic conductor components and/or dielectric components, for example, via incorporation a polymer encapsulant, such as biopolymer, silk, a silk composite, or an elastomer encapsulant.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes devices having one or more barrier layers, for example, one or more barrier layers positioned at the interface of the device with an external environment.

"Nanostructured material" and "microstructured material" refer to materials having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 µm. Nanostructured and microstructured materials include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides devices comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has ratio of thickness to a lateral dimension (e.g., length or width) selected from the range of 0.1 to 0.0001.

"Dielectric" refers to a non-conducting or insulating material. In an embodiment, an inorganic dielectric comprises a dielectric material substantially free of carbon. Specific examples of inorganic dielectric materials include, but are not limited to, silicon nitride and silicon dioxide. Dielectric materials further include silk, silk composites, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \qquad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \qquad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa. In an aspect, the functional layer has a low modulus and the delivery substrate has a higher Young's modulus, such as 10 times, 100 times, or 1000 times larger than the functional layer Young's modulus.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Figure 4:
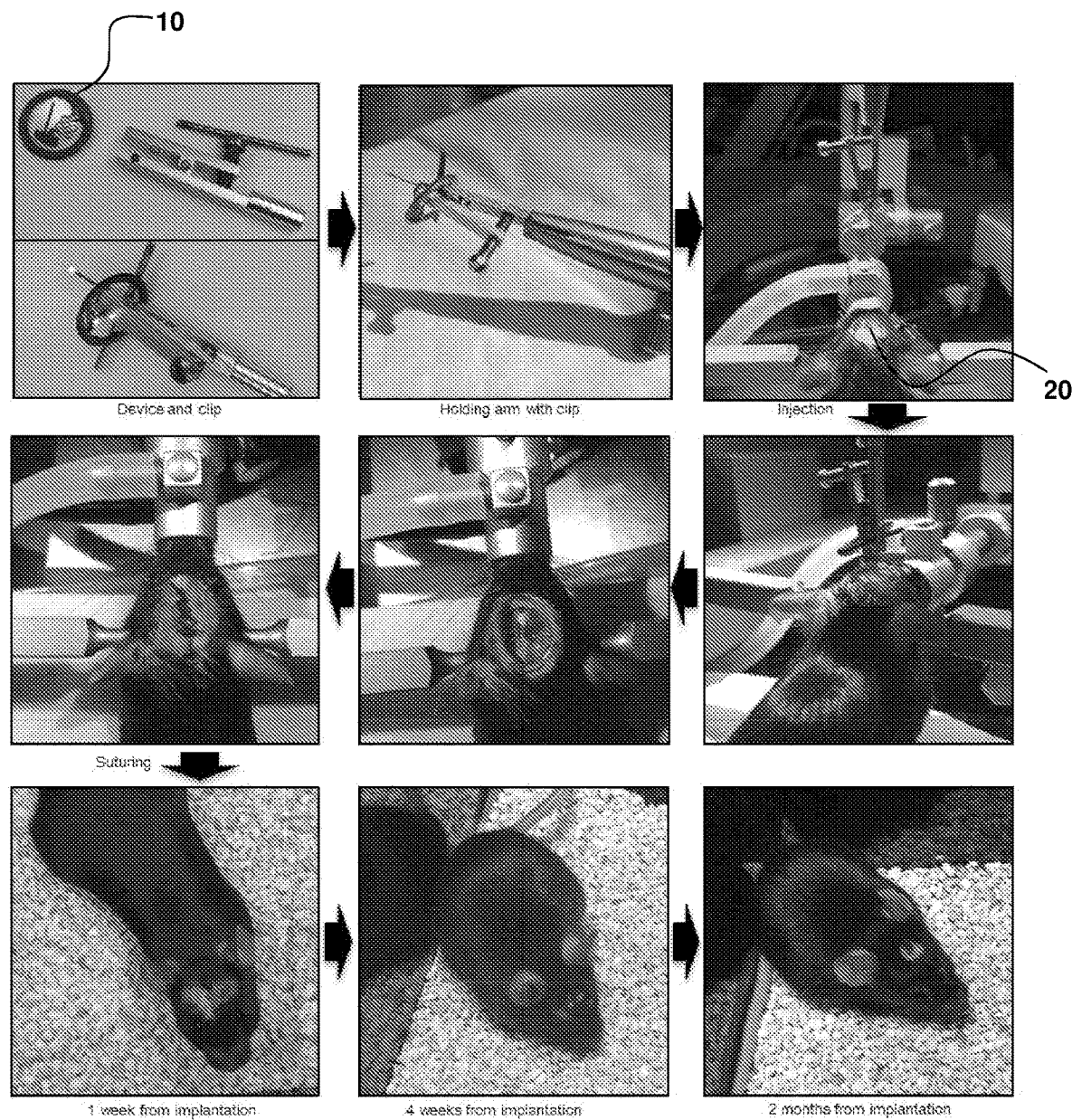
FIG. 4. Illustration of surgical procedures for implanting the device for operation in the deep brain. Images of the surgical steps for holding and positioning the body of the device, injecting the needle into the deep brain, suturing the skin and allowing the animal to recover.
Figure 28:
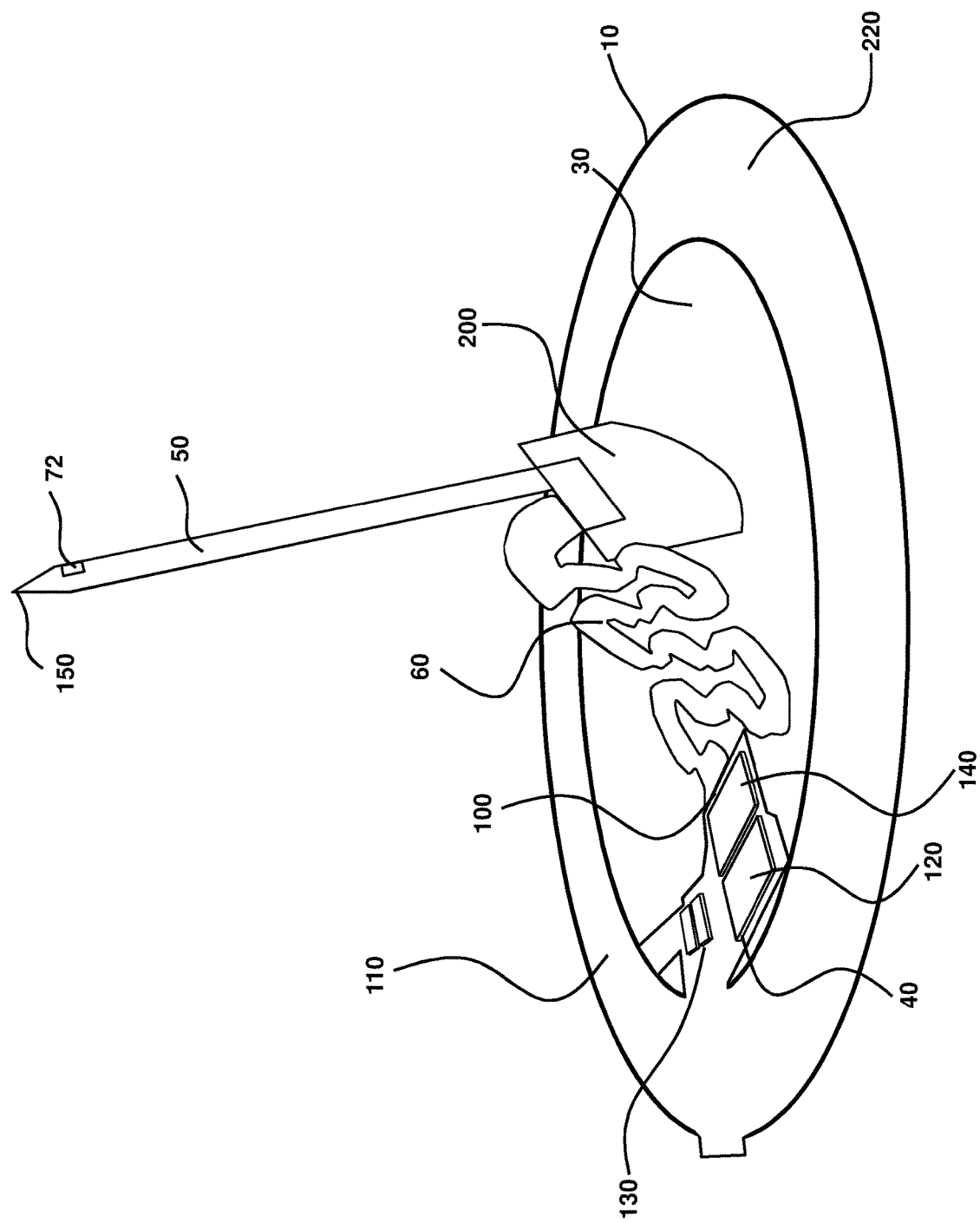
FIG. 28 is a perspective view of an implantable medical device.
Figure 29:
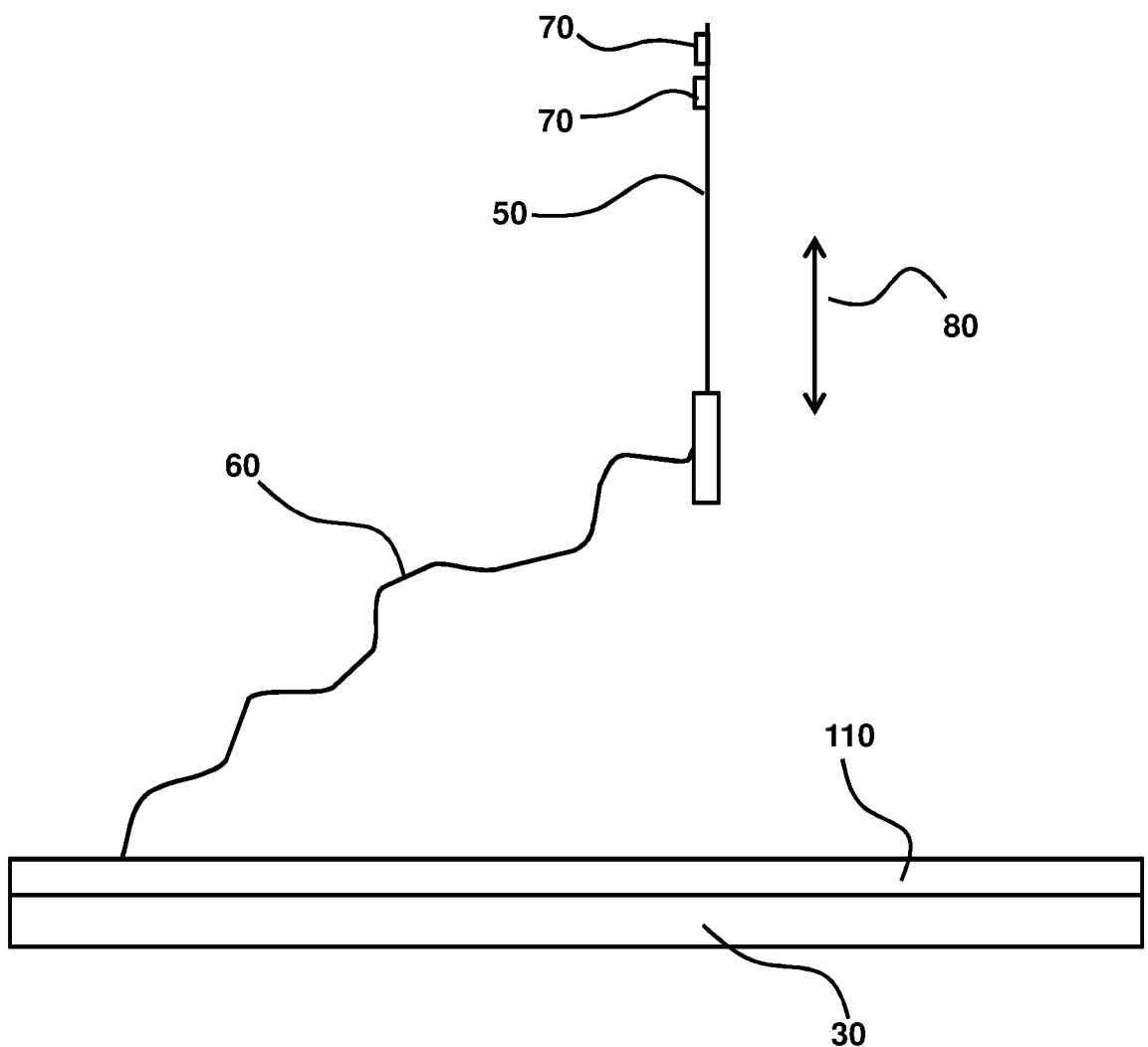
FIG. 29 is a side-view of FIG. 28.
Figure 30:
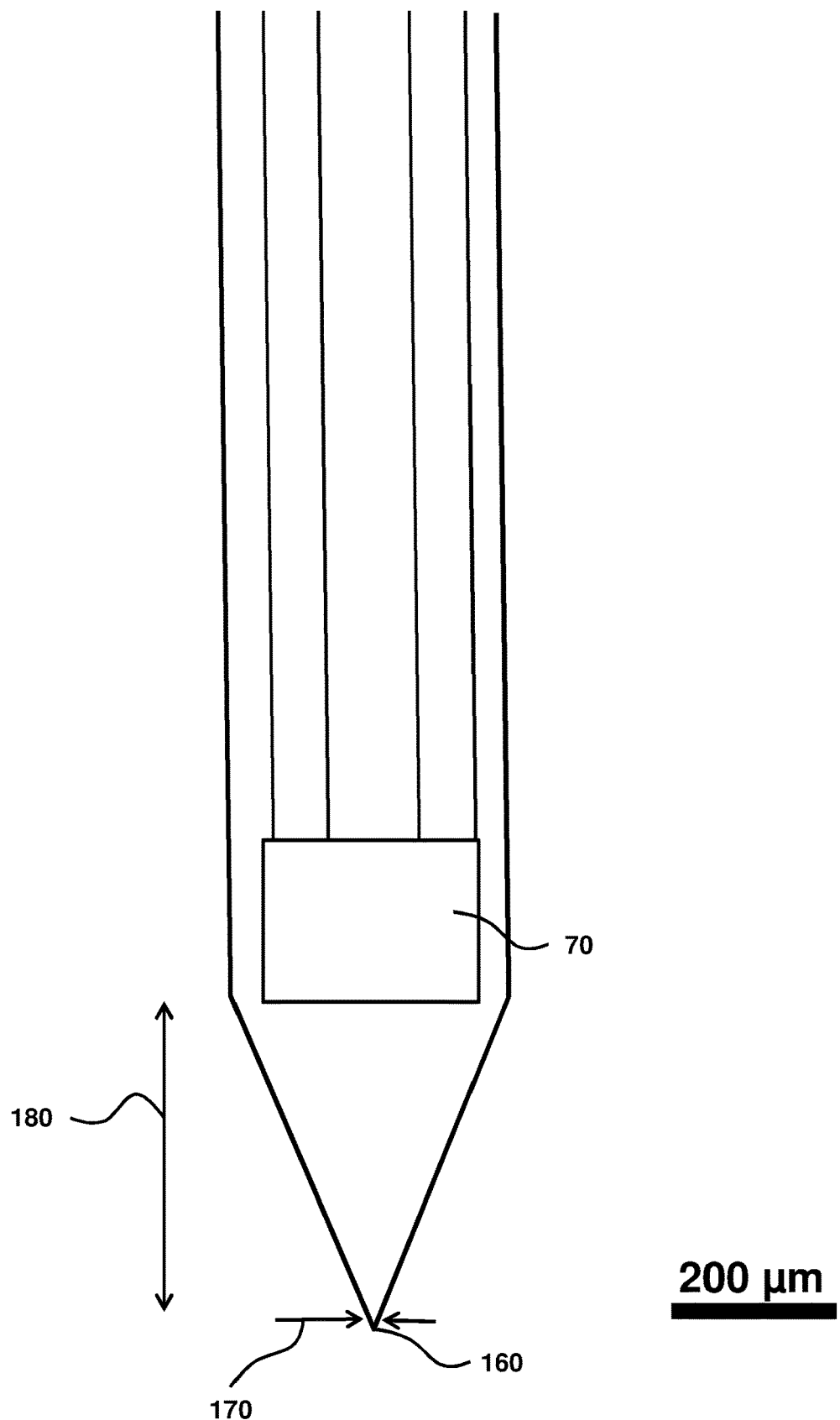
FIG. 30 is a close-up view of the distal end of the injectable needle.

FIGS. 28-31 schematically illustrate an exemplary embodiment of an implantable biomedical device 10. Target tissue may include, for example, deep brain tissue 20 (FIG. 4). A substrate 30 supports electronic device 40. The electronic device 40 is electronically connected to a probe or freely positionable injectable needle 50 by a deformable interconnect 60. For example, interconnect 60 may be in filamentary or serpentine configuration so that movement of needle 50 relative to electronic device is accommodated by gross deformation and/or movement of interconnect 60. For example, movement in a direction out of the plane defined by the electronic device, as indicated by double-sided arrow 80, can be accommodated by deformation of interconnect 60, including to relatively deep tissue insertion depths, including between 100 µm and 10 cm, 100 µm and 5 cm, or 100 µm and 5 mm, while ensuring robust electronic connection is maintained. The probe or needle 50 supports optical source 70, including if desired multiple optical sources (FIG. 29). Each optical source may be characterized by an emitting area, such as an emitting area 72 that is less than $10^6$ µm$^2$, less than $5\times10^5$ µm$^2$, less than $10^5$ µm$^2$, or between about $5\times10^4$ µm$^2$ and $10^6$ µm$^2$.

The positionable probe or needle may be defined relative to a point 100 defined by the notional intersection between the deformable interconnect 60 and the electronic device 40. Accordingly, point 100, length of interconnect 60, and angle between interconnect and electronic device defines a substantially conical volume in which the probe or needle is readily positionable without any adverse impact on biomedical device operating characteristics.

Figure 31:
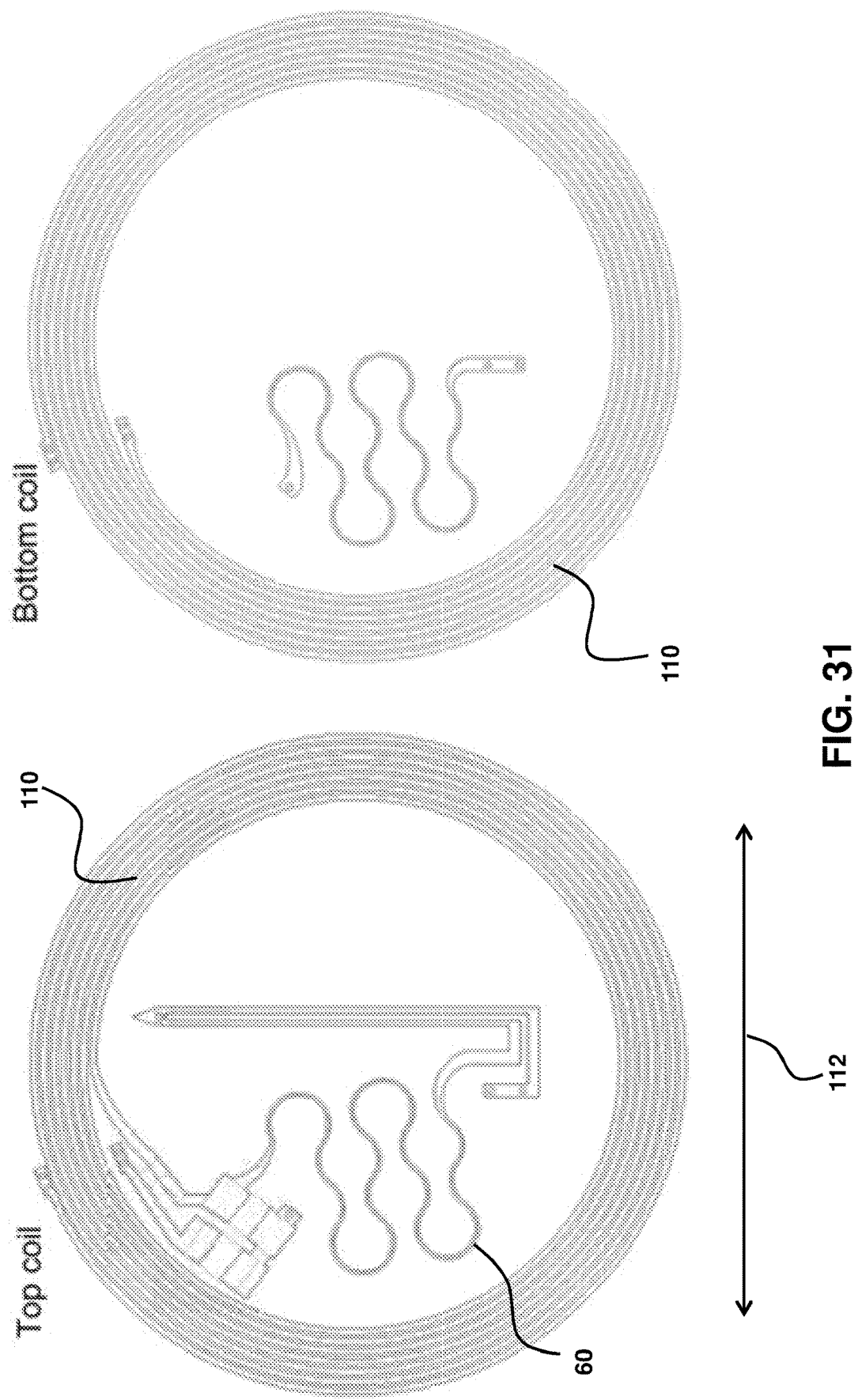
FIG. 31 is a top-view of the top coil and associated circuitry (left panel) and of the bottom coil (right panel).

The electronic device 40 may further comprise a coil 110, a rectifier 120, a capacitor 130 and an optical indicator 140, in electronic connection to provide desired functionality to electronic device. Probe or needle 50 may have a distal tip end 150, such as a pointed end 160 (FIG. 30) defined by a lateral dimension 170 and a taper traversing a longitudinal distance 180. Coil 110 may be described as having an inner diameter 112 so that the deformable interconnect 60 is disposed within a region 114 defined by inner diameter 112 (FIG. 31). Tab 200 (FIG. 28) may connect the needle and interconnect to facilitate controlled movement of the needle in any one, two, or three-dimensions.

Figure 19:
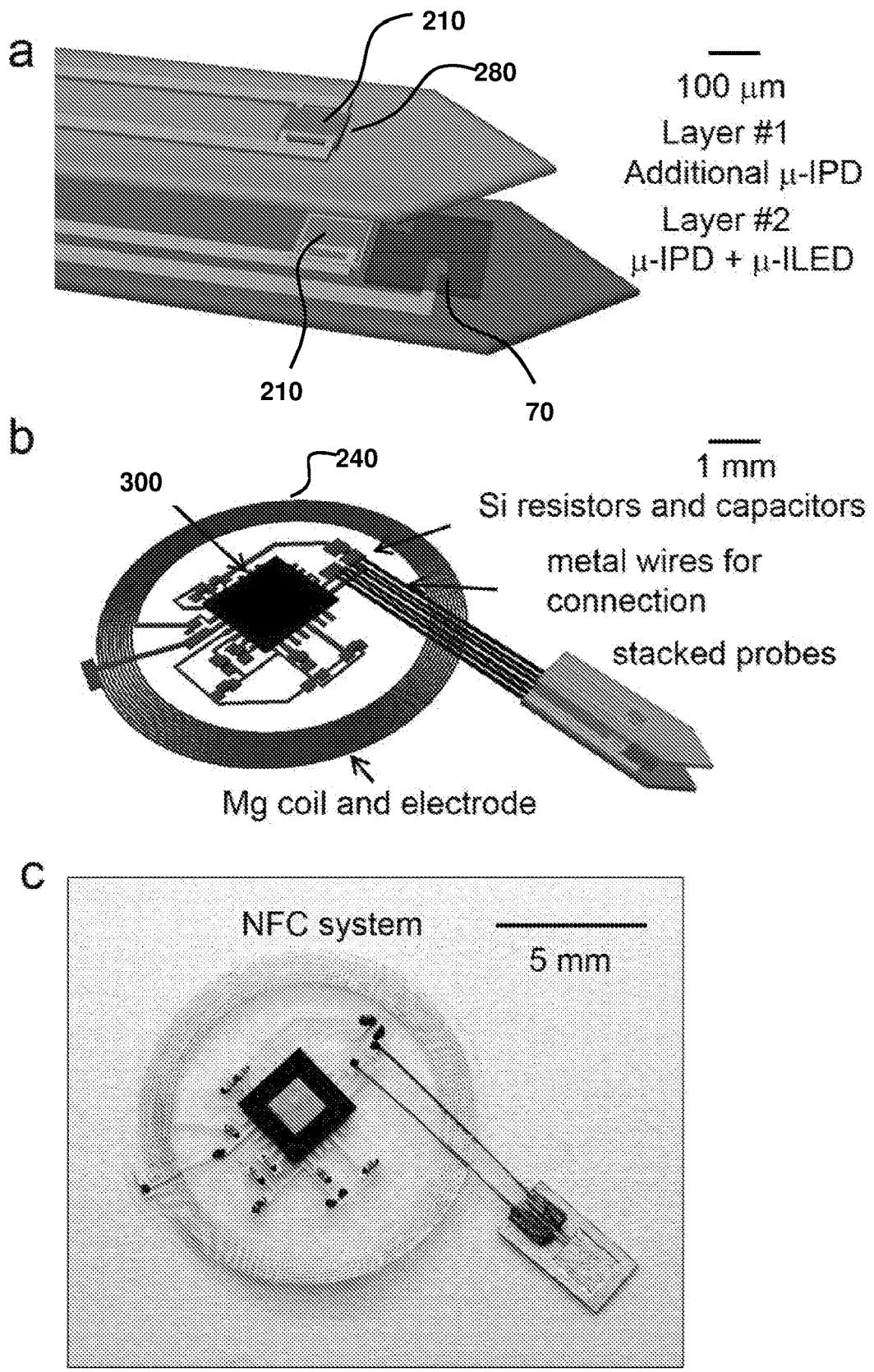
FIG. 19. Schematic illustrations and pictures of injectable photometers and wireless hardware. a, Demonstration of multilayer injectable photometry probe. An optional layer #1 can support an additional μ-IPD for calibration of power variations. Layer #2 supports a μ-IPD and a μ-ILED. b, Schematic illustration of an implantable wireless system for power delivery and data communication. c, Image of an NFC system developed for ICP monitoring[7]

As desired, the probe or needle may have additional functionality by incorporating additional components. For example, an optical detector, such as a photodetector or a photodiode 210 may be provided so that an optical property may be measured. FIG. 19 illustrates two photodetectors 210 and an optical source 70, provided in a multi-layer configuration.

An encapsulating layer or barrier layer 220 may cover a portion or all the device, including covering the coil (FIG. 28).

Figure 12:
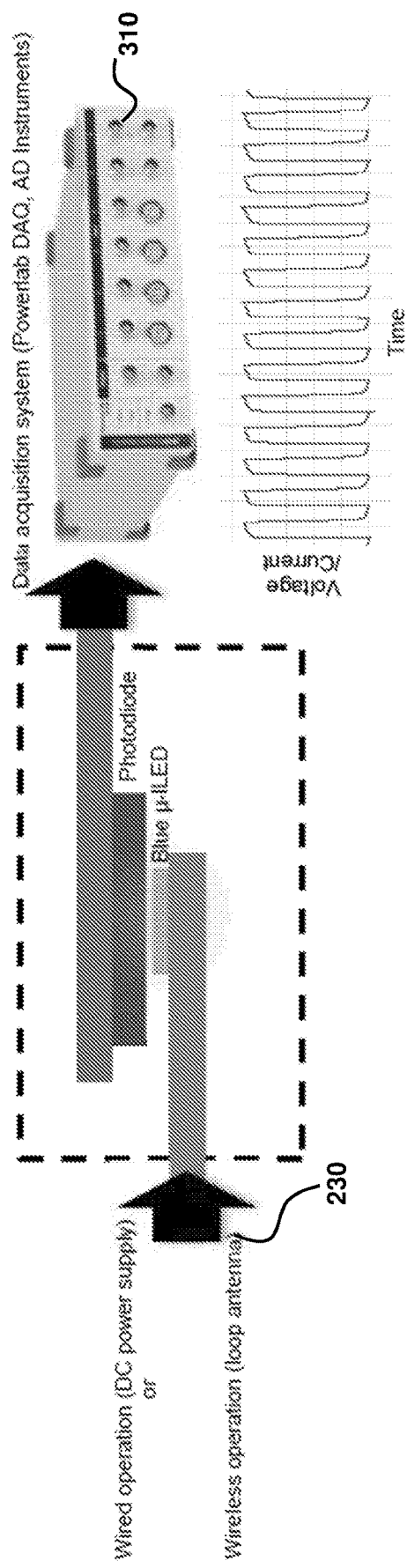
FIG. 12. Schematic illustration of output power density measurement.

Other components may include antenna 230 and external reader 310 (FIG. 12). The device may be a wireless system 240 to provide wireless control and data acquisition. An NFC chip 300 and a magnetic loop antenna 290 may facilitate wireless powering, control and data transmission (FIG. 19). Other components may include optical components such as optical filters 280 or optical dispersion elements (not shown). External reader 310 may be used for power transfer and data collection (FIG. 12).

Example 1: A Low Cost, Fully Implantable Optoelectronics Technology with Near-Field Wireless Operation for Broad Application in Optogenetics Abstract Optogenetics, which enables light-induced, area-confined stimulation or inhibition of genetically targeted neurons, is now an essential tool for modern research in neuroscience. Implantable optoelectronic technologies offer the most powerful and versatile capabilities in optogenetics experiments, but their specialized designs are not easily adapted to the type of mass manufacturing approaches that are needed for distribution to the broader community. Furthermore, the associated radio frequency schemes for power delivery and control depend sensitively on details associated with the sizes, shapes and positions of metallic components and/or water features in and around the experimental environment. In this example, we present a fully implantable device platform compatible with near field communication hardware, similar to that used for RFID tags and, with growing ubiquity, for consumer electronics (e.g. smart phones, tablets, etc). The result is a manufacturable, low cost technology for optogenetics that can be deployed easily and quickly, in nearly any environment, by researchers with little or no expertise, or interest, in RF electronics. The thin, flexible implantable components can be used as disposable items, inserted using straightforward surgical procedures, with robust, chronic stability in operation. Detailed studies of the electronics and mechanics designs, surgical insertion methods, system level configurations, issues in biocompatibility and demonstrations of use in animal model research highlight the capabilities and essential features of the technology.

Introduction

Understanding and controlling the function of the brain represents a grand challenge in modern scientific research. Historically, techniques in electrical stimulation using penetrating or surface mounted electrodes served as the most common means for activating/de-activating neurons to determine their roles in cognitive function.[1-3] Confounding thermal effects, lack of cell type specificity, inability to target small numbers of neurons inside electrically conductive bio-tissues and adverse long-term effects on tissue health are some of the many disadvantages associated with such approaches.[4] Optogenetics avoids these complications through the use of light and photosensitive ion channels in genetically modified neurons to stimulate or inhibit activity in a highly targeted and controlled fashion.[5-7] This methodology is now widely viewed as essential for progress in neuroscience research, with enabling capabilities for sophisticated studies of function in the central and peripheral nervous systems.[8,9] Recent developments in materials science and electrical engineering allow this form of optical control to be achieved through the use of soft, flexible optoelectronic implants that deliver light directly to regions of interest using ultraminiaturized light emitting diodes (LEDs), powered and controlled wirelessly. Such devices enable a range of experiments on untethered, freely behaving animals, in isolation or in social groups, in simple or elaborate environments, in a manner that bypasses the constraints associated with traditional optical fiber interfaces and external connections to separately located light sources, power supplies and control electronics.[9-13] Even the most advanced wireless systems, however, have drawbacks, including the reliance on (1) specialized device architectures and unusual combinations of materials that are not easily adapted to low cost manufacturing and (2) wireless operation in radio frequency bands that are susceptible to signal reflection, interference and absorption by metallic objects, water features and other obstructions within or adjacent to the area of interest. As a result, such technologies require expertise in radio frequency electronics for optimized configuration and reliable operation, the overall costs of the hardware are high, and the implantable devices are not broadly available. Options in solar and battery power eliminate some of these disadvantages, but they limit experimental options and add significant weight and bulk, respectively; neither addresses the issues of cost and availability.[9-14] Solutions to these difficulties can be found in recently reported, small-scale, flexible optoelectronic devices designed for wireless operation on the fingernails by inductive coupling at frequencies (13.56 MHz) [16,17] aligned with near field communication (NFC) hardware found in commoditized consumer and industrial electronic devices. The work reported here demonstrates that related NFC schemes and miniaturized, flexible wireless receivers can serve as the robust basis for a technology for optogenetics. Unlike previously reported wireless systems designed for the UHF (ultrahigh frequency, 300-3000 MHz) bands, these inductively coupled antennas operate in the HF (high frequency, 3-30 MHz) band. The result enables full wireless coverage across nearly all cage types and environments, with little sensitivity to the presence of objects or physical obstructions, including those made of metals or with significant water content. Reliable operation underwater and/or through metallic cages/plates is even possible. This level of robustness in function greatly reduces requirements in RF optimization and tuning. In addition to commoditized NFC transmission and control hardware, the implantable components can be manufactured using established processes adapted from the flexible printed circuit industry. Here, we demonstrate these features in a device platform that includes ultrathin injectable needles that support sub-mm scale LEDs (which we refer to here as microscale inorganic LEDs, or μ-ILEDs) for implantation at targeted regions of the brain. An electrically connected sub-system integrates a flexible magnetic loop antenna, rectifier and indicator LED that mounts sub-dermally on top of the skull, to offer chronic stability (many months) in operation without any observable adverse effects on the animals. Detailed studies of these devices and affiliated external hardware, including demonstrations of their use in live animal model studies of behavior, illustrate all of the key features of the technology.

Figure 7:
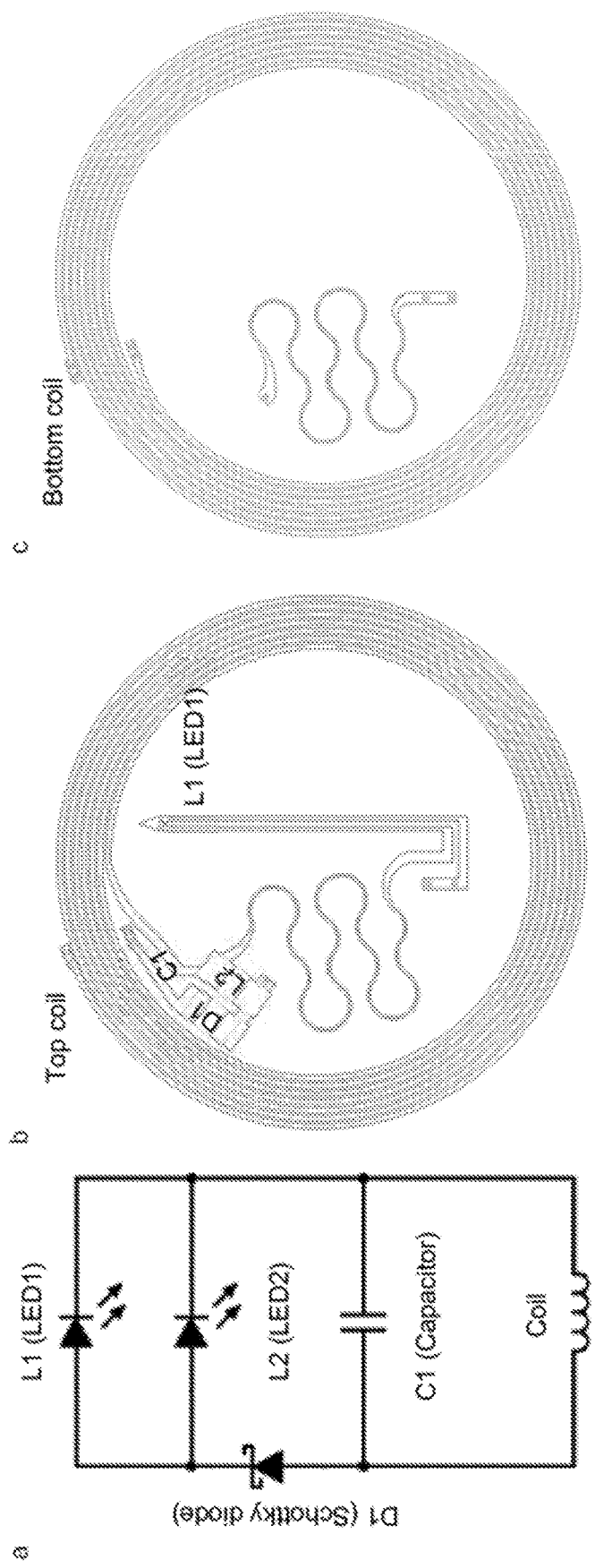
FIG. 7. A) Circuit diagram, B) coil/device design and C) information of chip components.

FIG. 1 presents schematic illustrations, images and data that summarize the design features and operational characteristics of a thin, flexible, millimeter scale, implantable device for localized delivery of light to targeted regions of tissue, including living tissue such as the brain, with capabilities in wireless power transfer and control for optogentics studies. The device incorporates various functional (copper metallization) and barrier layers (parylene and poly(dimethylsiloxane)) and active components (surface mounted chips and unpackaged light emitting diodes) fabricated on a substrate of polyimide (75 μm thickness) in an overall planar geometry to facilitate processing by conventional manufacturing techniques. An open mesh architecture allows out-of-plane motion of an injectable needle during manipulation and implantation (see, e.g., FIG. 1, panel d top-right), and also out of plane deformation of the substrate during use (see, e.g., FIG. 1, panel d top-left). This needle incorporates a μ-ILED (270 μm×220 μm×50 μm) at the tip end. The electrical interface consists of a pair of metal lines that pass along a serpentine interconnect trace to allow vertical and horizontal freedom of motion relative to a connected circular coil (9.8 mm diameter, copper traces: 8 turns, 60 μm width, 18 μm thickness and 80 μm spacing) with surface mounted chips for power transfer and control via magnetic coupling to a separate radio frequency (RF) transmission loop antenna operating at 13.56 MHz [17]. Here, a capacitor (23 pF) provides for impedance matching. A Schottky diode rectifies the received RF signals to yield a current source for operating the μ-ILEDs. The system includes two separate μ-ILEDs: one, with emission in the blue (470 nm), resides adjacent to the targeted tissue to serve as the source for optogenetic simulation or inhibition; the other, with emission in the red (650 nm), lies just under the skin next to the coil to provide an externally visible signal of system activation, at a wavelength that is invisible to the mice.[19] We refer collectively to this red μ-ILED, the coil and associated components as the body of the device. Additional information about circuit design and exemplary chip components appears in FIG. 7. FIG. 1 panel b shows a picture of a complete system next to a US dime (17.91 mm diameter). After encapsulation of the entire system with a bilayer of parylene (5 μm) and poly(dimethylsiloxane) (PDMS; 0.5~500 μm), the maximum thickness is 1.5 mm (at location of the chips for the rectifier), similar to that of the dime (1.35 mm); the minimum thickness is 0.5 mm at the position of the coil and associated interconnect wiring. The needle has a total thickness of <0.2 mm and a width of ~0.35 mm. These miniaturized dimensions, the lightweight construction (~30 mg) and the mechanical flexibility represent attractive characteristics as a versatile platform for wireless delivery of light not only into targeted regions of the brain but also to other organs and tissues, for various purposes. An enlarged image of the μ-ILED component on the tip of the needle (350 μm width) appears in FIG. 1 panel c (left) and FIG. 30. The bottom contact pads of both μ-ILEDs bond to corresponding copper features via a solder paste (SMD290SNL250T5, Chipquik). The colorized SEM image of FIG. 1 panel (right) shows a representative trace of the coil, designed to resonate at 13.56 MHz with a Q factor of ~22 and an inductance of ~1.8 pH. The coil and serpentine interconnect exhibit excellent mechanical flexibility and stretchability, respectively, as shown in the images and modeling results of FIG. 1 panel d. The results indicate stable operation under bending to a radius of curvature of <4 mm and/or stretching of the serpentine trace by up to 300%.

Three dimensional modeling of the mechanics reveals that the maximum strains (<2%) in the copper remain below the fracture threshold (5%) even under these extreme cases of deformation.

Figure 8:
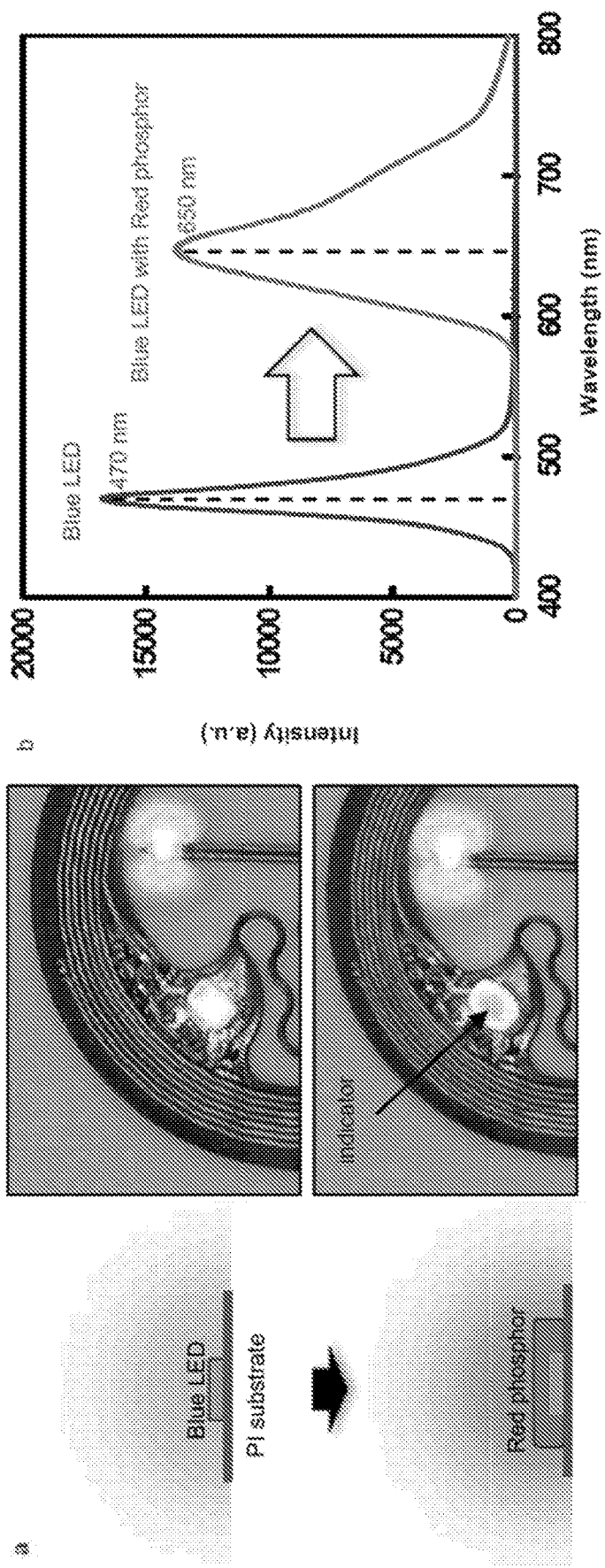
FIG. 8. A) Schematics and photoimages of phosphor coating, B) Emission spectra of blue LED and red indicator.
Figure 9:
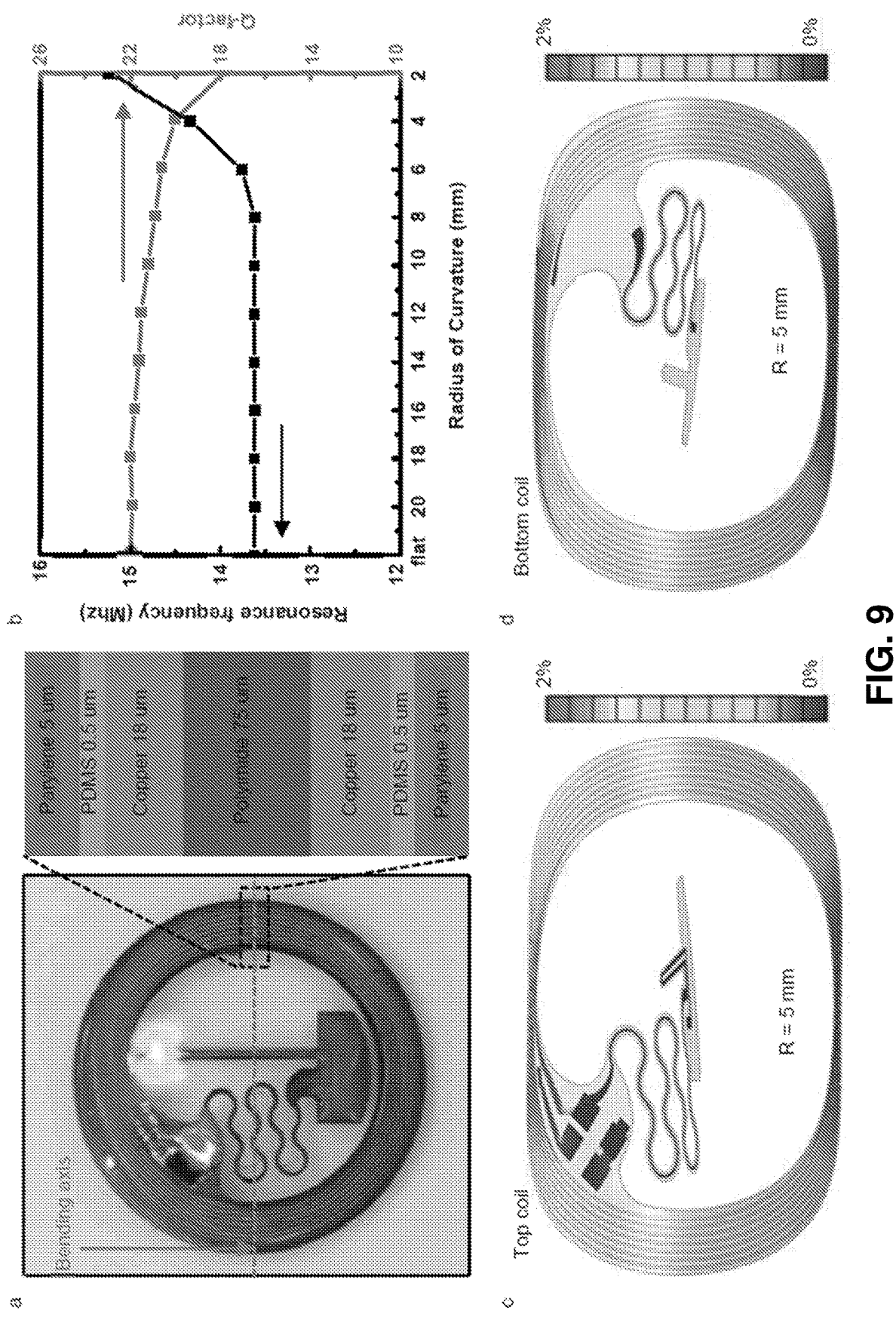
FIG. 9. A) Cross-sectional view of optogenetic implant, B) Resonance frequency and Q-factor versus bending radius, C-D) Strain distribution of bent top and bottom coils, respectively.

FIG. 2 summarizes the essential electrical, optical, mechanical, and thermal properties. The current-voltage response and the optical output power highlight the key operational characteristics. An external loop antenna interface to an RF generator (Feig system; 12 W output power) can wirelessly supply sufficient power for device operation at distances of up to 30 cm. The output power density estimated from the measured current-voltage curve is on the right y-axis of FIG. 2a. Most optogenetic experiments demand power densities of 1-50 mW/mm$^2$ [5-12], well within the range accessible with these devices, over distances that span the dimensions of most cage environments of interest for optogenetics experiments on small animals. Optical emission in the ultraviolet (UV), blue, green, yellow and red covers many of the most popular opsins, including ChR, HR, Arch and others. [5,6] This entire wavelength range can be addressed in devices that incorporate appropriate µ-ILEDs, as shown in images and emission spectra in FIG. 2b. Fabrication of UV devices (390 nm; 100 µm×100 µm×6 µm) exploits previously reported lithographic processes [11]. The blue (470 nm; 220 µm×270 µm×50 µm) and green (540 nm; 220 µm×270 µm×50 µm) devices use commercial blue and green µ-ILEDs, respectively. The yellow (580 nm; 220 µm×270 µm×50 µm) and red (650 nm; 220 µm×270 µm×50 µm) devices use yellow and red phosphors (FIG. 8) coated onto blue µ-ILEDs, respectively. See supplementary note 1 for detailed information. The encapsulation bilayer of parylene (5 µm)/PDMS (0.5~500 µm) extends across all surfaces. Immersion in saline solutions at different temperatures (37, 60 and 90° C.) reveals that these layers provide barrier properties that enable good operational stability. Except for the case of 90° C., the devices survive for at least 90 days without noticeable degradation of optical power (FIG. 2c). Based on Arrhenius scaling, the encapsulated devices are projected to survive up to a year at 37° C. in saline solution. [20] In vivo measurements yield qualitatively consistent results. More than 80% (24/30) of successfully implanted devices survive more than 4 months inside the brain and under the skin. Additionally, the optical power is invariant to stretching of the needle up to 300% and bending of the coil to a radius of curvature as small as 6 mm, as shown in FIG. 2d. Detailed modeling results and mechanical characteristics appear in FIG. 9. This level of flexibility allows the device to be placed conformally over the curved surface of the skull after injecting the needle into the brain.

Figure 10:
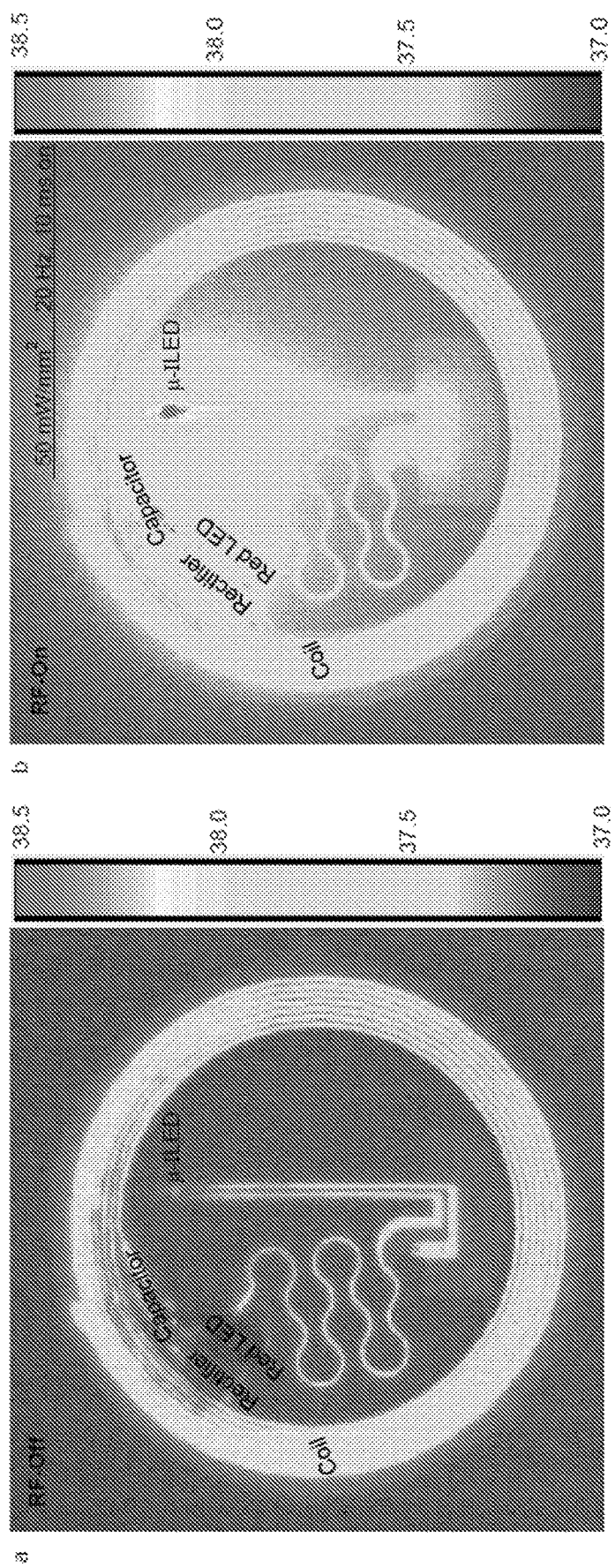
FIG. 10. IR images of device surface A) before and B) after wireless operation with the output power of 50 mW·mm$^{-2}$ and the pulse parameters of 20 Hz, 20 duty cycle.
Figure 11:
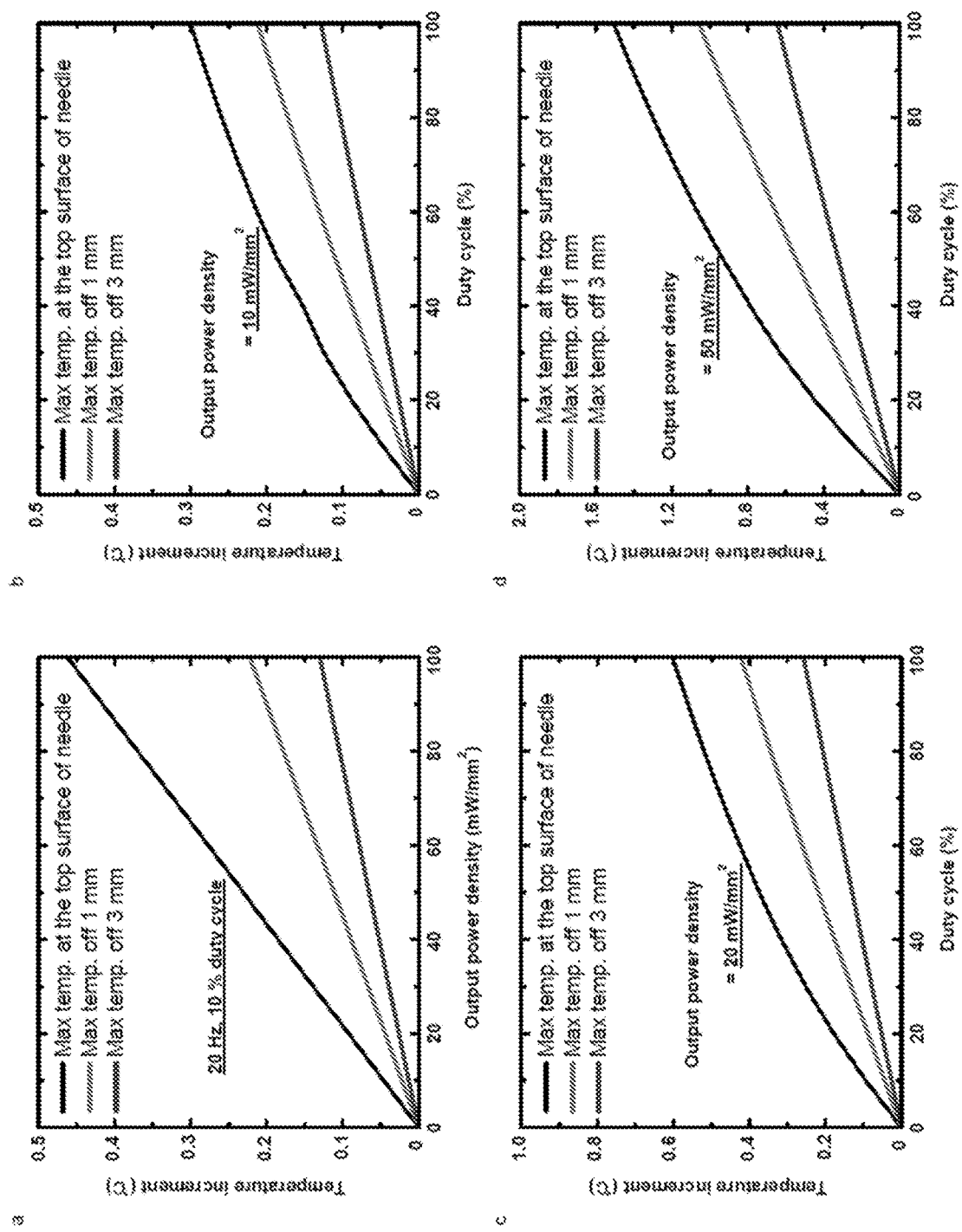
FIG. 11. Thermal modeling of brain injected LED device versus A) output power densities and B-D) duty cycles.

Thermal considerations are important to the operation of any active device implanted in the brain or any other sensitive biological tissue. Infrared imaging reveals no measurable changes in the temperature across the surfaces of the body of the device, including the coil, the red LED, the rectifier and capacitors, during wireless operation of the blue µ-ILED at power densities up to 50 mW/mm$^2$ in the air (FIG. 10). Careful measurements of temperature at the surface of the blue µ-ILED (FIG. 2e; E) as a function of the duty cycle during pulsed operation at three different peak optical power densities compare well to those computed using three dimensional thermal models (FIG. 2e; T). Additional modeling results appear in the supplementary note 2 and the FIG. 11. The results show only minute increases in temperature (~0.1° C.) during operation under typical conditions for optogenetics, e.g. output power of 10 mW/mm$^2$ and 20 Hz pulsing at a duty cycle of 20%. Here, the RF transmission system coupled to the loop antenna defines the pulsing parameters. FIG. 2f shows representative pulse sequences based on square waveforms at various frequencies (5, 10 and 20 Hz). Here, a low capacitance and high speed photodiode (PDB-C609-2 Silicon Photodiode, API Inc.) placed on top of the operating µ-ILED measures the light output. The waveforms (control via Arduino) have rise and fall times of <0.1 ms. Additional information appears in the supplementary note 3 and FIG. 12.

Figure 3:
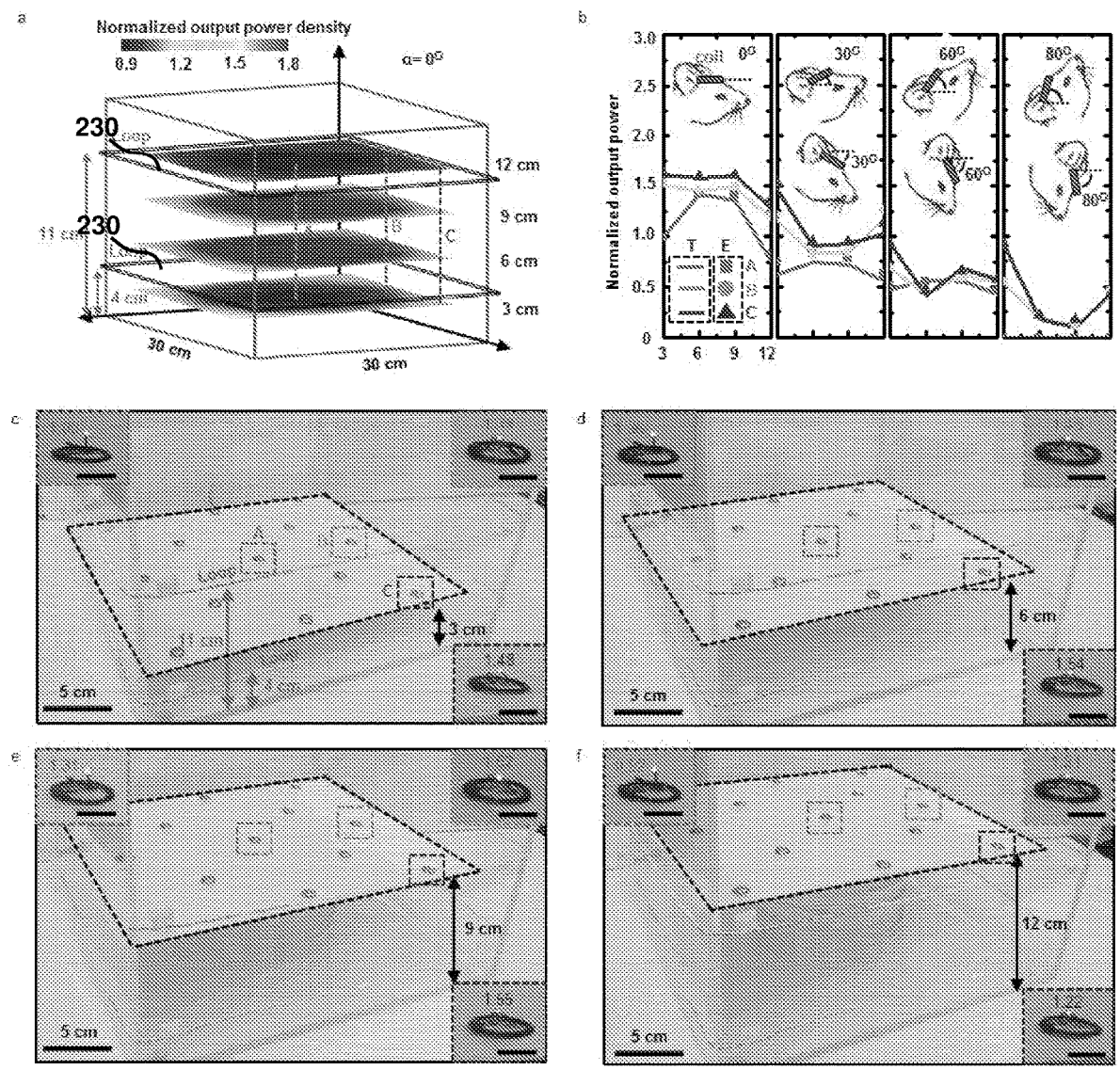
FIG. 3. Modeling and experimental results for power transmission from loop antennas with different designs. A) Simulated output power densities from a wireless device, as a function of in-plane position at four different heights from the bottom of an enclosure, for the case of a double loop antenna with turns at heights of 4 and 11 cm. B) Theoretical (lines) and Experimental (symbols) results for the normalized output power density as a function of height for four different angular orientations between the coil and the loop antennas. The inset cartoons show tilted views of the head of the animal. C-F) Wireless operation of thirteen devices mounted on a thin transparent support, placed at heights of 3, 6, 7 and 12 cm from the bottom.
Figure 13:
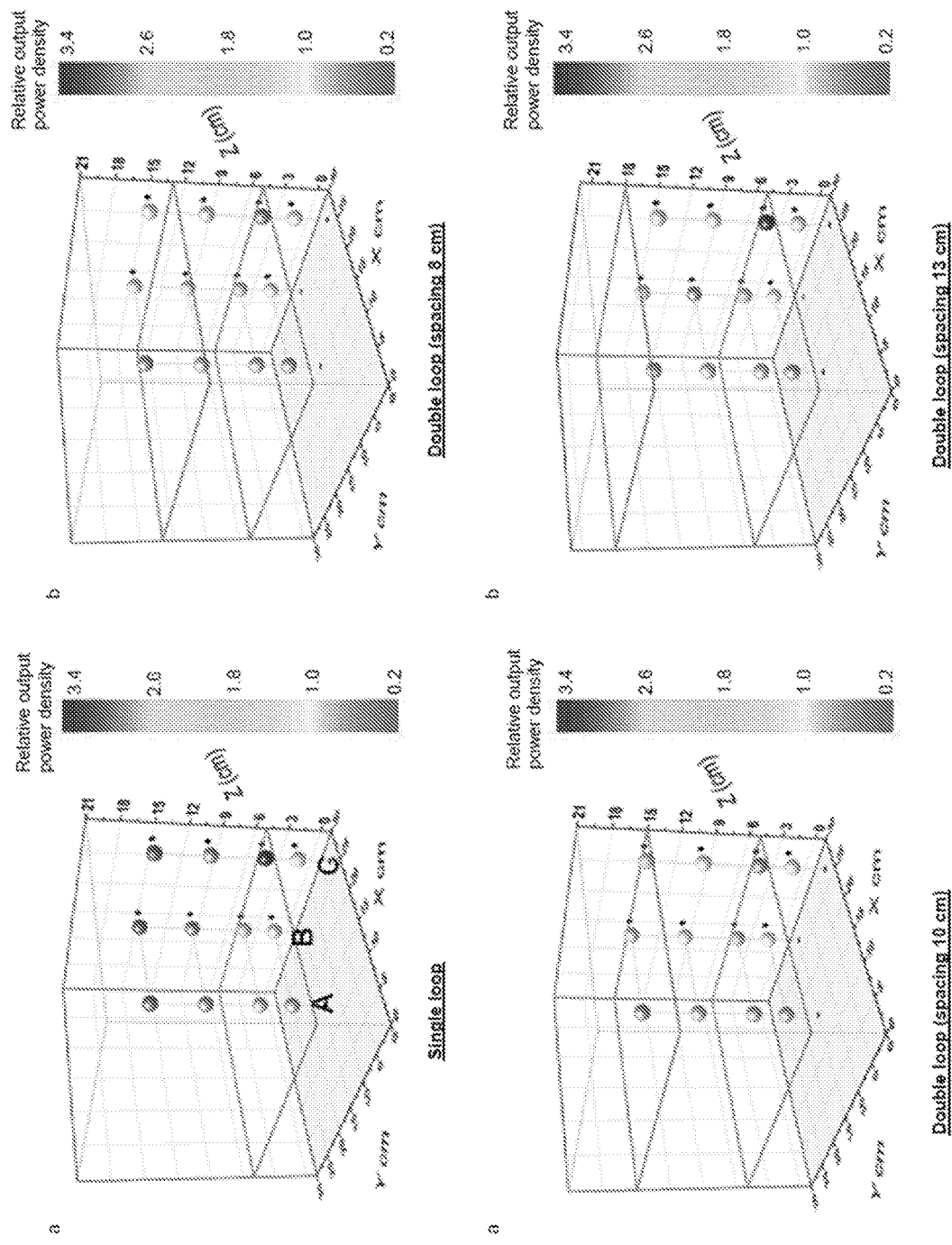
FIG. 13. Experimental measurement of relative output power densities of A) single and B-D) dual loops antenna systems.

In addition to the device coil, the transmission loop antenna must be optimized for efficient power transfer. The voltage induced in the receiving coil depends the distance from the loop and their relative angular orientations. A single loop with dimension of 30 cm×30 cm shows uniform in-plane coverage (Ratio of output densities from the center point >0.6), whereas it offers a comparatively narrow range of out-of-plane uniformity, such that only 40% of the maximum optical output appears at a vertical distance of 4 cm from the loop. (FIG. 13A) The double loop design provides a more uniform distribution of output density as a function of height. FIG. 3 panel a shows a representative configuration that consists of a double loop antenna 230 with turns at heights of 4 cm and 11 cm from the bottom of an animal enclosure with dimensions of 30 cm×30 cm×30 cm. The magnetic field from this double loop inductively couples to the coil of the device for wireless operation with good coverage (Ratio of output densities >0.6 (in-plane), >0.8 (out-of-plane)) across the region of interest. Findings from additional experiments for dual loops with spacings 8, 10 and 13 cm, indicate reduced uniformity in coverage compared to the 7 cm case (FIG. 13B-D).

The output power also depends on the relative angular orientation between the loop antenna and the device coil. FIG. 3b summarizes simulation results and experimental data for output power of devices at three representative positions (A, B and C) and various heights from the bottom of the enclosure as a function of the angle. All power values are normalized to the center point (A) at a height of 3 cm. At angles of 0, 30, 60 and 80 degrees, normalized powers are 0.8~1.5, 0.6~1.4, 0.5~0.9 and 0~0.9. The practical significance of these angular variations must be considered in use of these devices for optogenetics experiments. Advanced antennas and RF delivery schemes offer some potential to minimize these effects, as described with some initial results that appear subsequently.

The spatial uniformity can be visualized directly by simultaneous operation of a large collection of devices (thirteen in this case) placed on a transparent thin substrate inside an enclosure surrounded by a dual loop antenna (30 cm×30 cm×15 cm), as in FIGS. 3c-f. These observations are consistent with those suggested by calculation, and they also illustrate the ability of this system to operate many devices at once. Data from such experiments can be captured using a calibrated photodiode to measure the optical outputs of each of the µ-ILEDs (FIG. 12). The voltage-output power data, as shown in FIG. 2a, yields corresponding operating voltages. At heights of 3, 6, 9, and 12 cm from the bottom, devices at the same in-plane positions across the enclosure exhibit maximum variations in the output intensity of only 30%.

Figure 14:
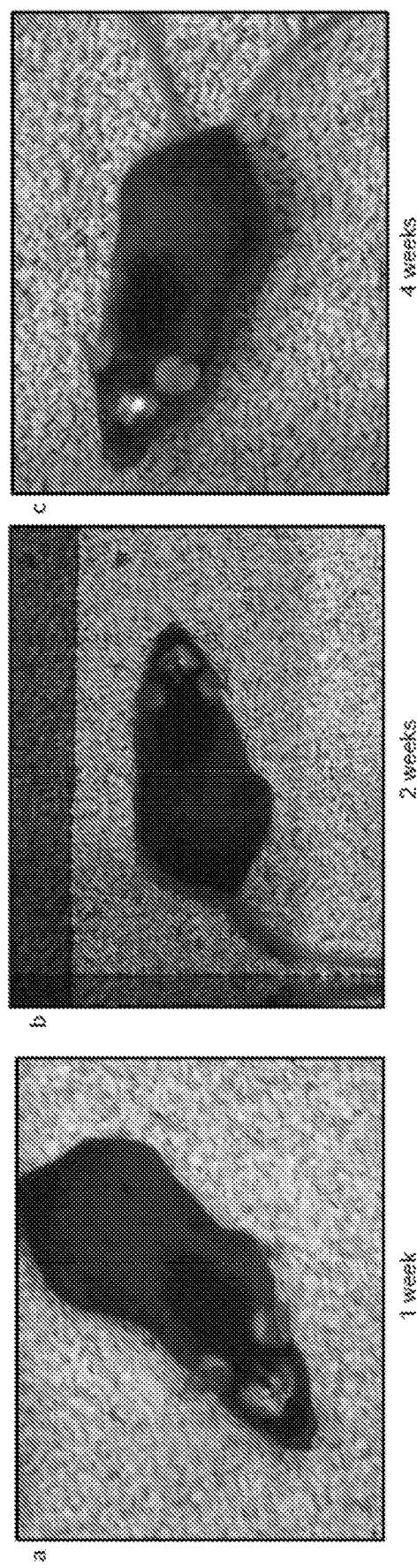
FIG. 14. Photoimages of mouse after A) 1 week, B) 2 weeks, and C) 4 weeks from the surgery.

FIG. 4 illustrates the surgical procedures for injecting the needle portion of the device into brain and for subdermally implanting the body of the device on top of the skull. A custom mounting fixture for the device connects to the arm of a stereotaxic stage for holding the needle and the coil. A small amount of dental cement (Jet denture repair, Lang Dental, cat. no. 1223) applied near the point of insertion fixes the needle to the skull. Removing the pin on the fixture releases the device body. Suturing the skin incision completes the process. Light from the red μ-ILED is easily visible through the skin, thereby providing a convenient indicator of operation. The bottom images of FIG. 4a show an implanted animal at various time points after the surgery. Additional images and data are in FIG. 14.

Figure 5:
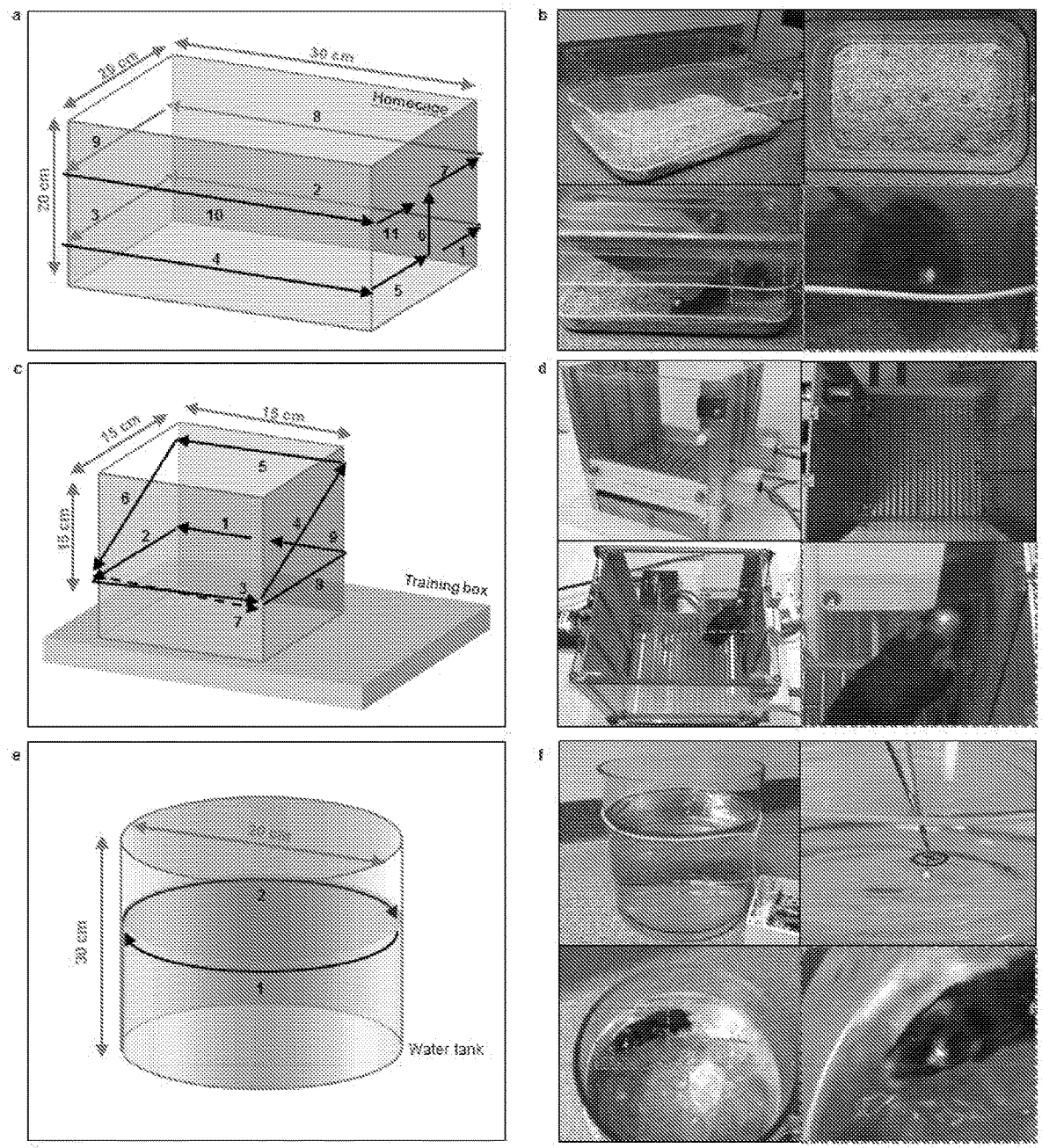
FIG. 5. Representative set up of the loop antenna around various animal apparatuses. A, C, E) The detailed layouts of the loop around a homecage, an operant conditioning box and a water tank, respectively. B) Images of the loop and wirelessly operating devices and the mice which have implants in the homecage covered with lid. D) Images of dummy mice and real mouse who has working device in the operant conditioning chamber which has metal components. F) Images of water tank with single loop antenna, working devices on the water surface and a swimming mouse that has working device.

Depending on the dimensions of the animal apparatus, double loop and/or diagonal loop antennas can increase the volumetric and angular coverage. FIG. 5 shows operation in various representative cages and boxes commonly used for behavior studies. Conventional fiber optic approaches or wired hardware cannot be used effectively for using enclosed cages (i.e. homecage) and for doing social interactive behaviors with more than one mouse, due to entanglement of the wires. Even wireless systems that rely on high frequency RF cannot operate reliably due to their sensitivity to surrounding metal components and/or water pools/reservoirs in or around the cages. [14-16] By contrast, such structures do not prevent use of the magnetically coupled systems introduced here. In fact, lid-closed homecages with food and water containers are also fully compatible, largely independent of materials and structures, suitable for studies of individuals or groups of mice.

Figure 15:
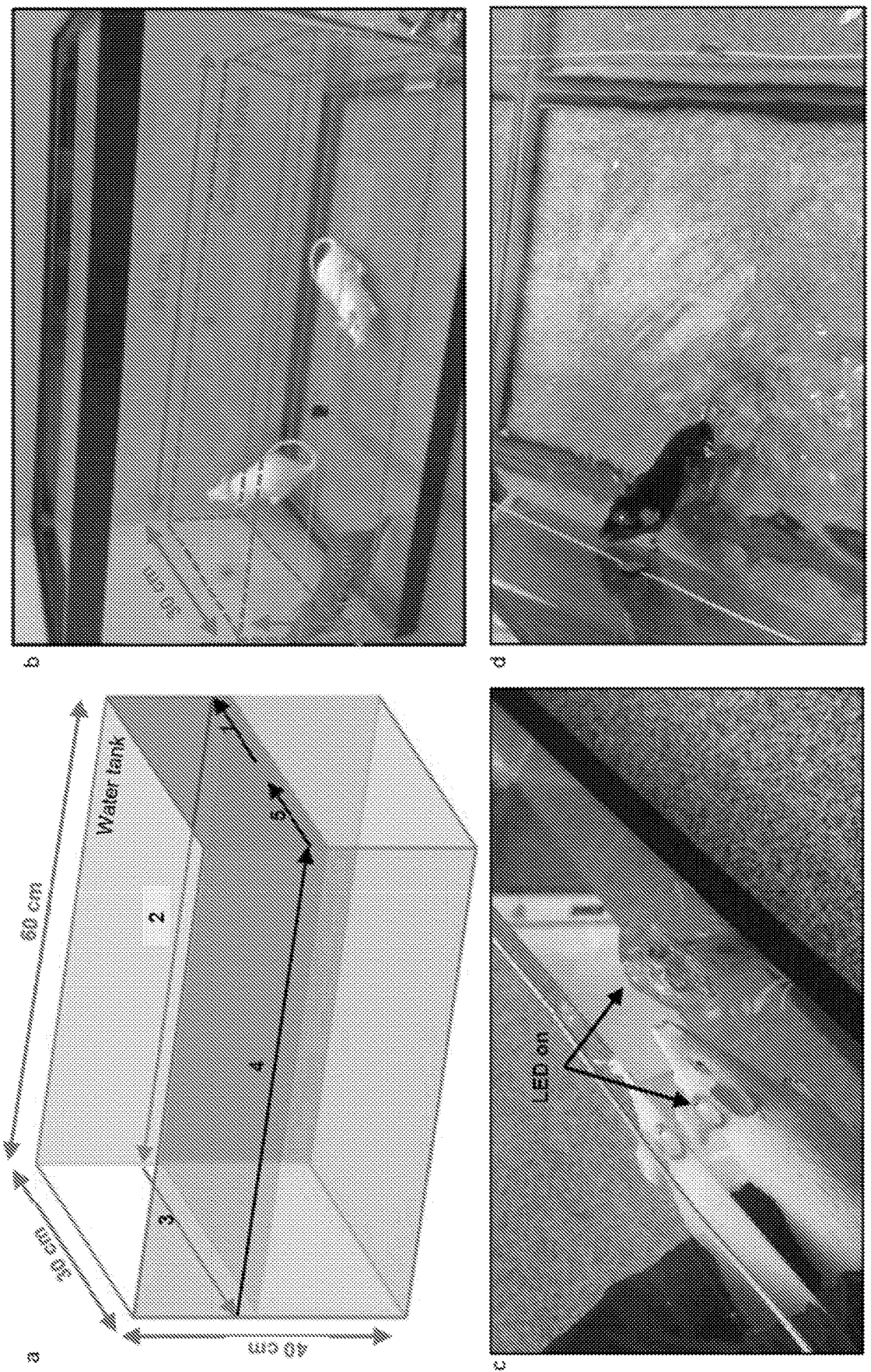
FIG. 15. A) Loop design on the water tank. Wireless operation of LED devices attached on B-C) dummy mice and implanted on D) real mouse.

The homecage shown here has a length of 30 cm, a width of 20 cm and a height of 20 cm. As in FIG. 5a, the loop starts at 4 cm from the bottom of one plane and surrounds the cage twice with 7 cm spacing between these two turns. The right top image of FIG. 5b shows that the double loop covers the entire volume, as illustrated by simultaneous operation of 15 devices. Mice with red indicators of operation move freely inside the homecage in the bottom frame of FIG. 5b. The Skinner box, also called an operant conditioning chamber, is in widespread use for the study and training of animals with reward of behavior toward various situations and external stimuli. The small but complex structure of such a chamber obstructs operation of both wired approaches and other wireless approaches. Also, many metal parts associated with slots on two sides and rod arrays/containers at the bottom can affect the performance and coverage of previously reported wireless systems. Unlike normal boxes, mice often stand and lean on the wall for relatively long times due to the small dimensions of the cage and the functioning parts on the wall. The double loop antenna around this small cage yields coverage inside the box in a manner that also enhances the angular coverage. FIG. 5d shows the placement of double coils and the results of evaluations of coverage using toy mice, as well as a freely moving live mouse with an implanted device. The water maze is another apparatus of interest for behavior tests. Here, the animals can swim and/or entirely submerge in the water, with little effect on device performance. A single loop coil around the water tank covers the area up to 4 cm above and below the surface of the water. FIG. 15 shows additional experiments in a large water tank and with submerged devices. Additional cage environments, including those with metal running wheels, can be found in FIG. 16.

Figure 6:
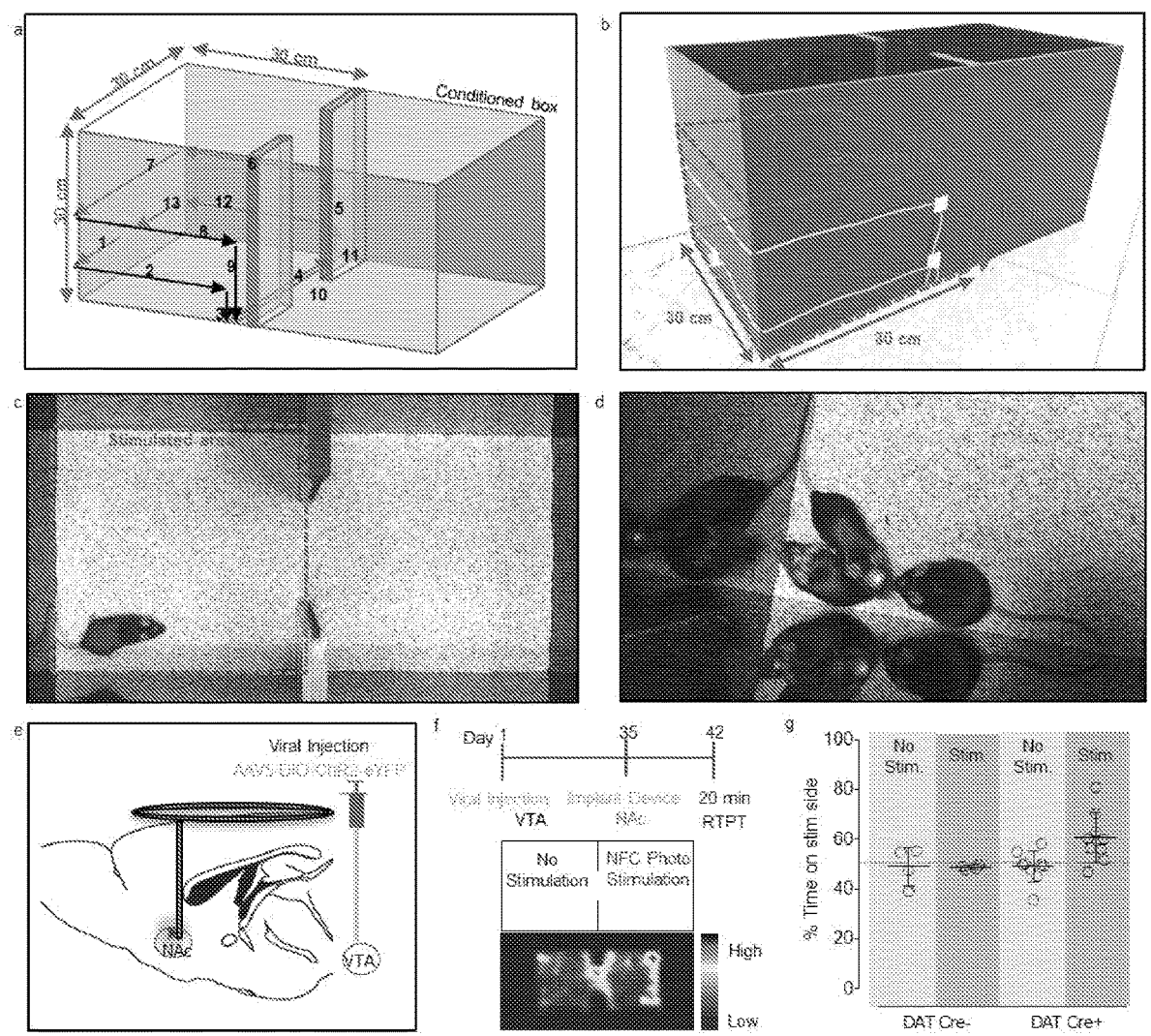
FIG. 6. Animal behavior experiment with real time place preference (RTPP) box. A) The layout of the modified double loop antenna around half side of RTPP box. B) Perspective view of the side of RTPP box which has to be covered wirelessly. C) Image of the working devices inside the box to show the coverage. D) Three mice have working implants in stimulated area. E) Schematic showing localization of the LED implant to the Nucleus Accumbens (Nac), and viral delivery of ChR2 to the ventral tegmental area (VTA). Cells in the VTA project to the NAc, where the LED can stimulate the ChR2 that is trafficked to the terminals. F) Experimental timeline and an example of the impact of VTA stimulation on the place preference of the mice. G) Group data from multiple experiments demonstrating effective use of the devices in vivo. Note that in mice not expressing ChR2, there is no preference for the stimulated zone, whereas mice expressing ChR2 in dopamine transporter (DAT) neurons show robust place preference on phasic stimulation of dopaminergic terminals in the NAc originating from cell bodies in VTA. This clearly demonstrates the effectiveness of the fully implanted, wireless LED devices.

Behavior experiments using reward circuitry on the VTA region demonstrate successful use of these devices in optogenetics experiments. Such studies involve a real time place preference (RTPP) box (2×30 cm×30 cm×30 cm) with a modified double coil design as shown in FIG. 6a. The coils rest under the box at its center region, to eliminate the influence on natural behaviors of freely moving animals within the box. As in FIG. 6b, the coil covers the dimensions of 30 cm (length), 30 cm (width) and 15 cm (height) which corresponds to a volume of 13.5 litres (13500 cm$^3$). Dummy mice and working LEDs appear in only half of the entire box (red dotted area in FIG. 6c) covered with a modified double loop.

Figure 27:
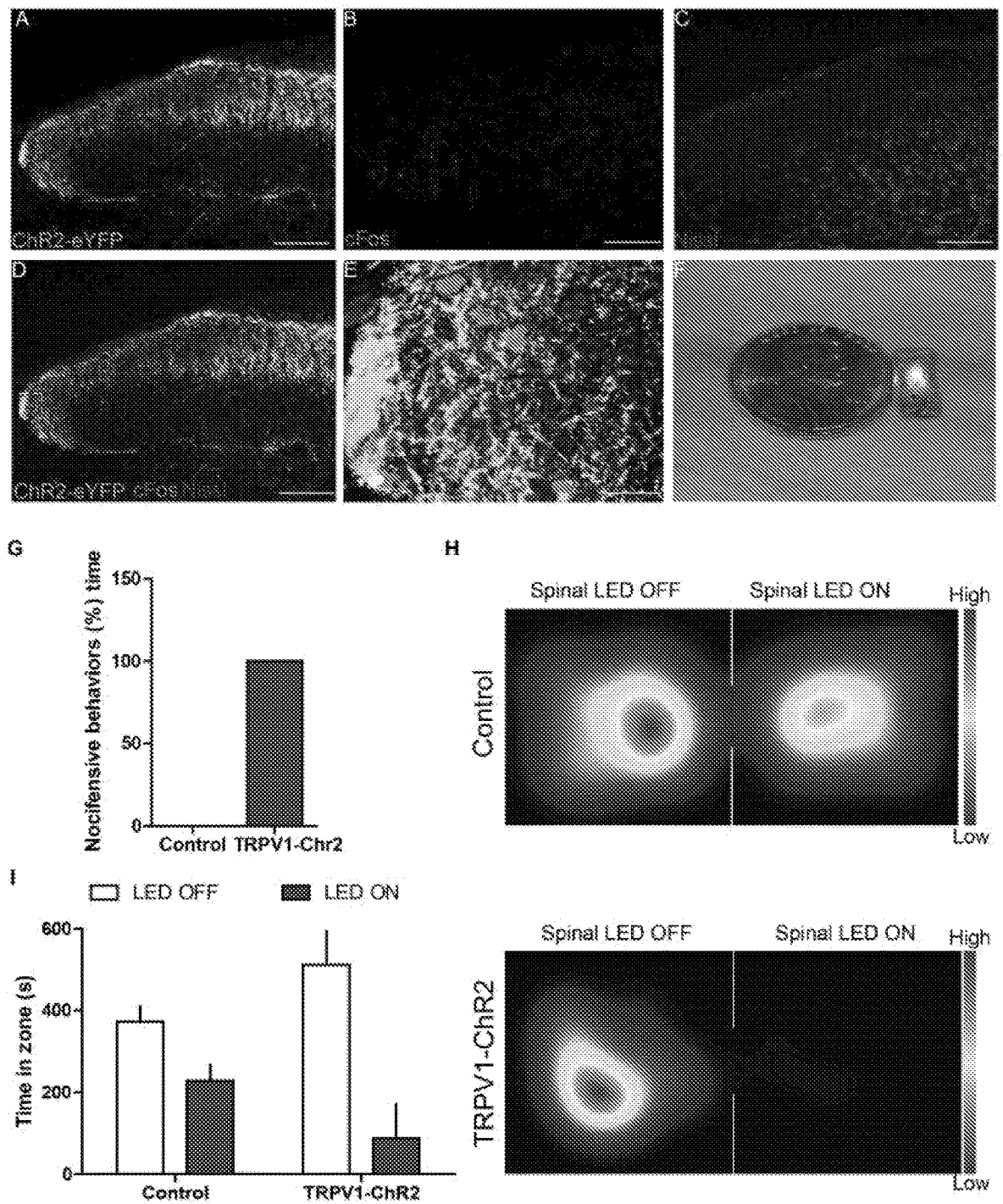
FIG. 27. A) Immunohistochemistry figures show the expression of TRPV1 Chr2-eyfp at the level of lumbar spinal cord. B) cFos (a marker for neuronal activation in spinal cord) activation showing neurons are activated at the spinal cord level after stimulating pain fibers. C) Nissl, marker for neurons. D) Merged image showing TRPV1-ChR2-EYFP, cFos and Nissl in spinal cord dorsal horn neurons. E) 40× magnified image showing TRPV1-ChR2-EYFP, cFos and Nissl in spinal cord dorsal horn neurons. F) Miniaturized NFC spinal uLEDs. G) Robust reliable nocifensive (pain) behaviors elicited only in TRPV1-ChR2 mice but not in control mice. H) Spinal NFC devices produced robust real time place aversion in TRPV1-ChR2 mice but not in control mice. I) Quantification of the time spent in each zone. TRPV1-Chr2 mice display aversion to the LED-ON zone but not to LED-OFF zone.

Mice received viral delivery of ChR2 to neurons in the NAc. Some of these neurons project to the VTA, and these projections are known to be involved in rewarding properties of behaviors and drugs. 35 days after viral injection (to allow adequate time for ChR2 expression and transport to axon terminals), wireless NFC LED devices were implanted, with the LED targeted to the NAc. One week later, mice were placed in a RTPP box for 10 min, with NFC activation of the device triggered on entry into the wirelessly covered chamber. Mice were tracked for 10 min in this apparatus, as shown (FIG. 6f). FIG. 6g shows grouped data from multiple experiments demonstrating that phasic stimulation (20 Hz, 2 sec) of the NAc produces no preference in control mice. However, in mice expressing ChR2 in the VTA→NAc projection, phasic illumination induces robust preference for the LED activated zone, clearly demonstrating the effectiveness of the fully implanted, wireless LED devices. The wireless optoelectronic systems reported here show great potential to be used in various optogenetic applications, such as complex cages, metal surroundings, and also water tanks. Injectable LED devices were easily implanted like an optical fiber and successfully survived mostly longer than 2 months inside the animal body without any performance degradation. A user-modifiable antenna system can cover most common apparatuses using by simple loop antenna design. Conditioned place preference and self-stimulation results represent clear behavior effects induced by these wireless power transfer systems and optoelectronic implants on the target neuron. And also simple modifications of the implants may allow these devices to be applied to other optogenetic targets, including the spinal cord and sciatic nerve. For example, FIG. 27 provides Immunohistochemistry figures showing the expression of TRPV1 Chr2-eyfp at the level of lumbar spinal cord (A), cFos (a marker for neuronal activation in spinal cord) activation showing neurons are activated at the spinal cord level after stimulating pain fibers (B), Nissl, marker for neurons (C), and a merged image showing TRPV1-ChR2-EYFP, cFos and Nissl in spinal cord dorsal horn neurons (D) as well as a 40× magnified image showing TRPV1-ChR2-EYFP, cFos and Nissl in spinal cord dorsal horn neurons (E). FIG. 27(G) shows that robust reliable nocifensive (pain) behaviors are elicited only in TRPV1-ChR2 mice but not in control mice. FIG. 27(H) shows that spinal NFC devices produced robust real time place aversion in TRPV1-ChR2 mice but not in control mice. FIG. 27(I) provides quantification of the time spent in each zone. TRPV1-Chr2 mice display aversion to the LED-ON zone but not to LED-OFF zone.

Figure 18:
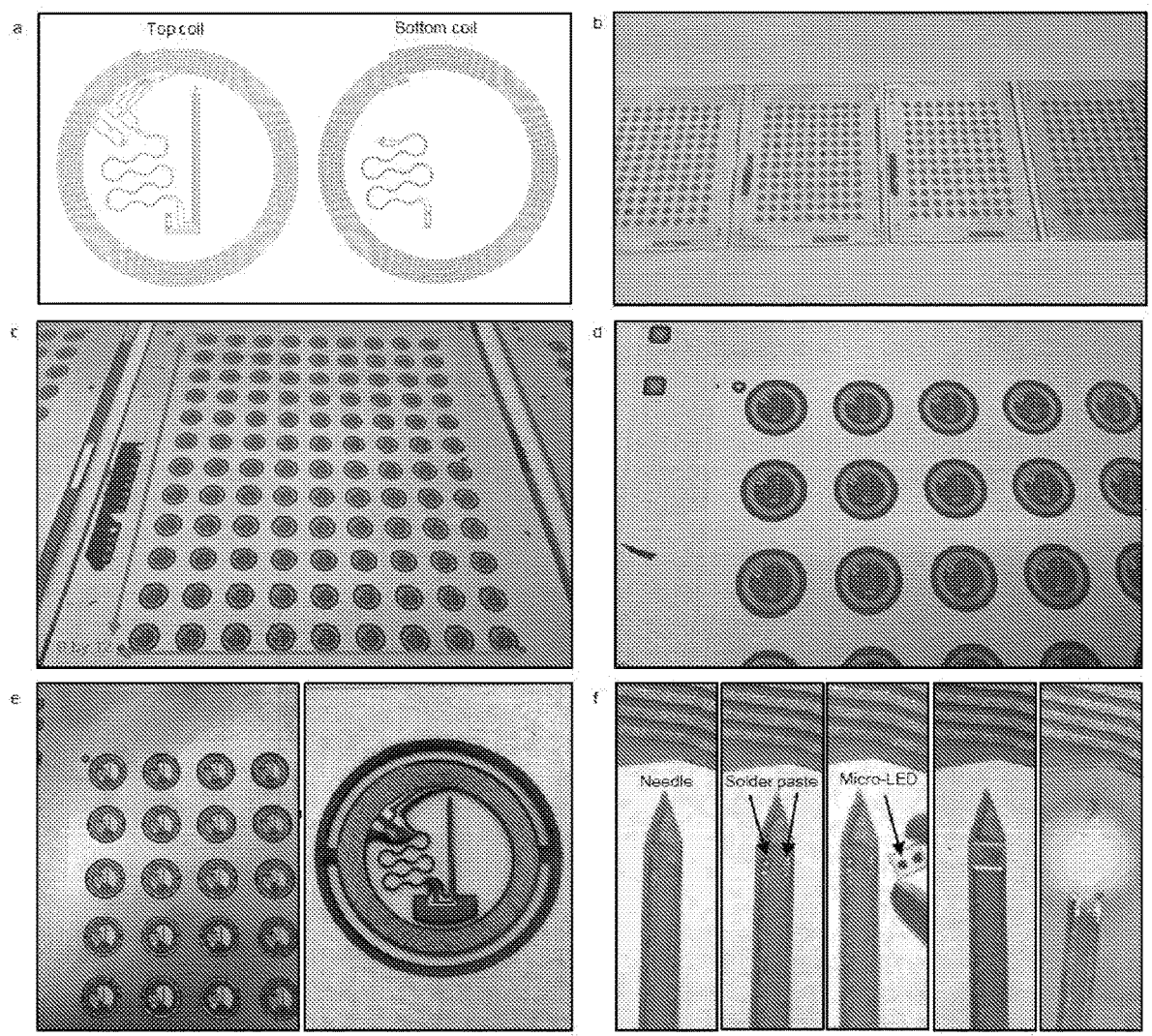
FIG. 18. Mass production of wireless optogenetic implants.

Customized wireless systems (FIG. 17) and potentials for manufacturing production of optoelectronic implants (FIG. 18) can make these fully implantable wireless device systems available as substitutes for current, limited, wired approaches.

REFERENCES

1 Campbell, P. K., Jones, K. E., Huber, R. J., Horch, K. W., and Normann, R. A. A silicon-based, three-dimensional neural interface: manufacturing processes for an intracortical electrode array. IEEE Trans. Biomed. Eng. 38, 758-768 (1991).
2 Cogan, S. F. Neural stimulation and recording electrodes. Annu. Rev. Biomed. Eng. 10, 275-309 (2008).

3 Kozai, T. D. et al. Ultrasmall implantable composite microelectrodes with bioactive surfaces for chronic neural interfaces. Nat. Mater. 11, 1065-1073 (2012).
4 Aravanis, A. M., Wang, L.-P., Zhang, F., Meltzer, L. A., Mogri, M. Z., Schneider, M. B., and Deisseroth, K., "An optical neural interface: in vivo control of rodent motor cortex with integreated fiberoptic and optogenetic technology", J. Neural. Eng. 4, S143-S156 (2007).
5 Boyden, E. S., Zhang, F., Bamberg, E., Nagel, G., and Deisseroth, K. Millisecond-timescale, genetically targeted optical control of neural activity. Nat. Neurosci. 8, 1263-1268 (2005).
6 Deisseroth, K. Optogenetics. Nat. Methods 8, 26-29 (2011).
7 Fenno, L., Yizhar, O., and Deisseroth, K., "The development and application of optogenetics", Annu. Rev. Neurosci. 34, 389-412 (2011).
8 Sparta, D. R. et al. Construction of implantable optical fibers for long-term optogenetic manipulation of neural circuits. Nat. Protoc. 7, 12-23 (2012).
9 E. R. Siuda, J. G. McCall, R. Al-Hasani, G. Shin, S. I. Park, M. J. Schmidt, S. L. Anderson, W. J. Planer, J. A. Rogers and M. R. Bruchas, "Optodynamic Simulation of b-Adrenergic Receptor Signaling," Nature Communications 6:8480|DOI: 10.1038/ncomms9480 (2015).
10 R. Al-Hasani, J. G. McCall, G. Shin, A. M. Gomez, G. P. Schmitz, J. M. Bernardi, C.-O. Pyo, S. I. Park, C. M. Marcinkiewcz, N. A. Crowley, M. J. Krashes, B. B. Lowell, T. L. Kash, J. A. Rogers and M. R. Bruchas, "Distinct Subpopulations of Nucleus Accumbens Dynorphin Neurons Drive Aversion and Reward," Neuron 87, 1063-1077 (2015).
11 Park, S.-I. et al. Soft, stretchable, fully implantable miniaturized optoelectronic systems for wireless optogenetics. Nat. Biotechnol. 33, 1280-1286 (2015).
12 Montgomery, K. L. et al. Wirelessly powered, fully internal optogenetics for brain, spinal and peripheral circuits in mice. Nat. Methods 12, 969-974 (2015).
13 Kim, T.-i. et al. Injectable, cellular-scale optoelectronics with applications for wireless optogenetics. Science 340, 211-216 (2013).
14 J.-W. Jeong, J. G. McCall, G. Shin, Y. Zhang, R. Al-Hasani, M. Kim, S. Li, J. Y. Sim, K.-I. Jang, Y. Shi, D. Y. Hong, Y. Liu, G. P. Schmitz, L. Xia, Z. He, P. Gamble, W. Z. Ray, Y. Huang, M. R. Bruchas and J. A. Rogers, "Wireless Optofluidic Systems for Programmable In Vivo Pharmacology and Optogenetics," Cell 162, 1-13 (2015).
15 McCall, J. G., Kim, T. I., Shin, G., Huang, X., Jung, Y. H., Al-Hasani, R., Omenetto, F. G., Bruchas, M. R., and Rogers, J. A. Fabrication and application of flexible, multimodal light-emitting devices for wireless optogenetics. Nat. Protoc. 8, 2413-2428 (2013)
16 Park, S.-I. et al. Ultraminiaturized photovoltaic and radio frequency powered optoelectronic systems for wireless optogenetics. J. Neural Eng. 12, 056002 (2015).
17 J. Kim, A. Banks, H. Cheng, Z. Xie, S. Xu, K.-I. Jang, J. W. Lee, Z. Liu, P. Gutruf, X. Huang, P. Wei, F. Liu, K. Li, M. Dalai, R. Ghaffari, X. Feng, Y. Huang, S. Gupta, U. Paik and J. A. Rogers, "Epidermal Electronics with Advanced Capabilities in Near-Field Communication," Small 11(8), 906-912 (2015).
18 J. Kim, A. Banks, Z. Xie, S. Y. Heo, P. Gutruf, J. W. Lee, S. Xu, K.-I. Jang, F. Liu, G. Brown, J. Choi, J. H. Kim, X. Feng, Y. Huang, U. Paik and J. A. Rogers, "Miniaturized Flexible Electronic Systems with Wireless Power and Near-Field Communication Capabilities," Advanced Functional Materials 25, 4761-4767 (2015).
20 Park, S.-I. et al. "Multi-channel, soft wireless optoelectronic implants for optogenetics". Submitted.

Supplementary Information

Supplementary Note 1. Fabrication of Red Indicator

Red (HTR650, Phosphor Tech) and yellow (HTY560, Phosphor Tech) phosphors were used to shift the emission wavelengths of light from blue LEDs. Each phosphor powder was mixed with epoxy (5 min curable) at a mass ratio of 5:1. A small amount of mixture covered the entire surface of the LED, and was cured in 10 mins in air. FIG. 8a shows schematic illustrations and pictures of phosphor-coated LEDs. The red phosphor yields red light (peak wavelength=650 nm) due to stimulation from the 470 nm light from blue LEDs. FIG. 8b shows the shift from blue to red in the emission spectra.

Supplementary Note 2. Thermal Characteristics

Temperature changes of the device and μ-ILEDs were monitored with an IR camera and an integrated temperature sensor. FIG. 10 shows the surface temperature of entire device, including a coil, rectifier, capacitor, red indicator LED and the injectable μ-ILED in air. There were no noticeable changes of the temperature over the whole device, whereas the temperature of μ-ILED increased by ~1.5° C. for an operating condition of 50 mW/mm$^2$, 20 Hz, 20% duty cycle after 10 mins operation. Modeling results for the temperature of tissue adjacent to an operating device as a function of the output power density and duty cycle appear in FIG. 11. The results are similar to experimental findings in FIG. 2E. For conditions typical of those used for optogenetic stimulation (<40% duty cycle, <50 mW/mm$^2$), the tissue temperatures increased by less than 0.8° C. Additional results correspond to measurements using Pt temperature sensors integrated directly next to the μ-ILED during operation inside a warm hydrogel (37° C.).

Supplementary Note 3. Output Density Measurements

Output power densities of wirelessly operating μ-ILEDs were measured with a photodiode (PDB-C609-2 Silicon Photodiode, API Inc.). The measured photocurrent is directly proportional to the optical output power from the μ-ILED at various wireless conditions (position, distance, angle and power). Calibration of the response of the photodiode to μ-ILEDs during wired operation using a separate DC power supply provides the actual output power. The voltage-output power data, as shown in FIG. 2A, yields the output power density of LED at above wireless operation. FIG. 12 shows schematic illustrations of the process for measuring and calculating the output power density from an μ-ILED and of the experimental setups for generating pulse waveforms using a separate control system (PowerLab DAQ, AD Instruments).

Example 2: Injectable and Implantable Photometry Devices

This example relates to the development of a robust, minimally invasive wireless photometry system for in vivo calcium measurements in freely moving behavior. To achieve this, a miniaturized, wireless, 'injectable' photometry platform (~300 mm wide, ~100 mm thick and several mm long) that enables quantitative measurements of fluorescence stimulated using a high performance microscale inorganic light emitting diode (μ-ILED) and captured using a co-located, sensitive microscale inorganic photodetector (μ-IPD) is described. These devices directly address current limitations in measuring calcium transient activity within any environment and facilitate sensing of genetically defined neural networks in more ethologically relevant behaviors.

These small-scale device components will mount on thin, flexible filaments with overall dimensions significantly smaller than fiber optic cables. The resulting systems will greatly reduce motion artifacts, due to their direct integration at targeted regions of the brain; when implemented using wireless schemes for power delivery and data communication, they will allow complete freedom of motion of awake, behaving animals, suitable for use in complex, three dimensional environments and in socially interacting communities. Preliminary data from using hard-wired versions of these technologies and separate demonstrations of wireless implantable platforms establish feasibility of the foundational concepts.

The goal of this example is to develop a robust, minimally invasive wireless photometry system for in vivo calcium measurements in freely moving behavior. This technology provides the ability to measure calcium transient activity (and even other fluorescent signals) within any environment and facilitates sensing of genetically defined neural networks in more ethologically relevant behaviors.

Innovations in optical methods for controlling and monitoring neural responses are essential to nearly every program of research in neuroscience. In vivo studies on awake, behaving animals offer some of the greatest areas of opportunity for understanding brain activity, yet the hardware systems that are currently available for such purposes are unfortunately often limited in their modes of use, due to requirements for (1) physical tethers to external data acquisition systems which constrain mobility in the animals and cause motion artifacts in the signals, (2) mechanically rigid, invasive probes which induce significant damage to neural tissue and evoke immune responses that limit the interface fidelity, (3) bulky batteries and/or hard wired connections for power supply which impart both physiological and psychological stresses on the animals. Recent developments in fully implantable, wireless devices for optogenetics open up entirely new possibilities in behavioral assays[1,2,3]. The present inventors seek to leverage and extend these emerging technology capabilities for precision photometry, a technique of rapidly growing importance across the neuroscience community. Current systems capture changes in calcium transient activity, through measuring fluorescence in animals using implanted optical fibers and external systems for light generation and detection, with all the disadvantages outlined above[4,5]. However, it is possible to build wireless, 'injectable' photometers by integrating high performance microscale inorganic light emitting diodes (μ-ILEDs) as light sources for excitation of genetically encoded calcium indicators such as GCaMP6 and co-located, sensitive microscale inorganic photodetectors (μ-IPDs) to monitor the resulting fluorescence associated with neuronal activity in genetically defined populations. These small-scale device components will mount on thin, flexible filaments with overall dimensions significantly smaller than fiber optic cables. Wireless power and data communication systems will allow operation on freely moving animals, in a manner compatible with complex, three dimensional environments and socially interacting colonies.

Preliminary data from using hard-wired versions of these technologies and separate demonstrations of wireless implantable platforms establish feasibility of the foundational concepts. This example seeks to develop a robust, minimally invasive wireless photometry system for in vivo calcium measures in freely moving behavior.

First, the example will examine brain activity in real-time on awake, behaving animals using a platform of injectable μ-ILEDs and μ-IPDs, with a test case measuring the fear conditioning responses. The thin, flexible, lithographically defined photometry probes will be inserted into targeted regions of the deep brain, such as the basolateral amygdala (BLA), including lateral, basal, and accessory basal nuclei using stereotactic positioning hardware and surgical procedures adopted from those used in previous wireless, injectable systems for optogenetics[2,3].

Second, the example will develop wireless schemes for power delivery and data communication for these systems, with demonstrations in fear conditioning and social interaction. Further size reductions and purely wireless modes of operation will greatly enhance the technology and the opportunities in neuroscience studies. Behavior experiments including fear conditioning and social interaction (known to evoke BLA activity)[6] will serve to demonstrate and optimize the fully wireless capabilities.

Optical techniques such as fluorescence imaging, photometry and optogenetics are increasingly essential in nearly every field of neuroscience research. As a result, advances in these methods will continue to contribute strongly to the pace of progress. Recent developments in tools for optogenetics, for example, allow wireless delivery of light directly into targeted regions of the brain, for purposes of stimulating/inhibiting the function of specific neural circuits, in a way that enables study of behaviors in freely moving animals, to allow insights into the activity of associated populations of neurons[1,2,3]. Such experimental manipulations do not, however, provide direct information on the extent to which the neuronal populations under investigation participate in these behaviors. Although emerging technologies for optogenetics afford capabilities for in vivo extracellular electrical recording, the resulting data do not reveal activity or larger neuronal networks (e.g. specific subtypes of interneurons) nor do they allow operation in freely behaving animals within any behavioral context (i.e. home cage, social interactions, etc) due to the necessity of tethering fiber optic and electrical cables. Current approaches in optical monitoring via fluorescence imaging and photometry, when used in optogenetic studies or in separate investigations, involve these same latter disadvantages, but with additional challenges in motion artifacts that follow from the use of external, remote hardware generation, commutation, and detection of light. The ability to measure calcium transient activity (and even other fluorescent signals) within any environment would open new questions and facilitate sensing of genetically defined neural networks in more ethologically relevant behaviors.

The devices disclosed here (FIG. 19) aim to directly address these current limitations through the development of a miniaturized, 'injectable' photometry platform that will enable quantitative measurements of fluorescence stimulated using a high performance microscale inorganic light emitting diode (μ-ILED) and captured using a co-located, sensitive microscale inorganic photodetector (μ-IPD). The resulting systems will greatly reduce motion artifacts, due to their direct integration at targeted regions of the brain; when implemented using wireless schemes for power delivery and data communication, they will allow complete freedom of motion of awake, behaving animals, suitable for use in complex, three dimensional environments and in socially interacting communities.

Preliminary data show that in vitro fluorescent signal changes from changes in $Ca^{2+}$ concentrations can be recorded using systems of the type described above. This technology will be transferred into freely moving animals to demonstrate the capabilities in recording of fluorescence in targeted neuronal populations. The inventors have developed novel approaches and methods for addressing living tissue. Specifically, an injectable fluorescence recording device in the format of a penetrating needle (~300 µm wide, ~100 µm thick and several mm long) that incorporates a µ-ILED and a µ-IPD with a narrow-band filter for recording calcium transient activity in specific, genetically identifiable neuronal populations will be fabricated and controlled behavioral responses of the same population of neurons in freely behaving mice using fine wired connections for power delivery and data communication will be demonstrated, then, advanced near field communication (NFC) techniques for battery-free purely wireless operation and signal transfer will be exploited.[7] A successful outcome of the work will establish a fully implantable platform for in-situ fluorescence photometry, with broad utility and versatile capabilities in many areas of neuroscience research, extending beyond calcium measurements in freely moving mice.

Preliminary device prototypes and details about how to generate, test, and validate a fully functional wireless photometry system for in vivo use are described. In animal studies, fluorescence recording of neuronal activity involves the genetically encoded calcium indicator, GCaMP6. In these animals we will use GCaMP6f (and alternate GCaMPs for optimization). We have generated a preliminary device to demonstrate feasibility of the approaches outlined in this example. In the prototype, the GCaMP is stimulated by an InGaN µ-ILED (220×270×50 µm) with emission between 450-480 nm, in sufficient overlap with the GCaMP6f excitation peak at 488 nm. A GaAs µ-IPD (200×200×4 µm) with a narrowband filter (a coordination dye complex with absorption maximum at 473 nm dispersed in a photo-definable, 7 µm thick epoxy matrix) to selectively capture fluorescence from the GCaMP6, whose emission peaks at 512 nm.

Figure 20:
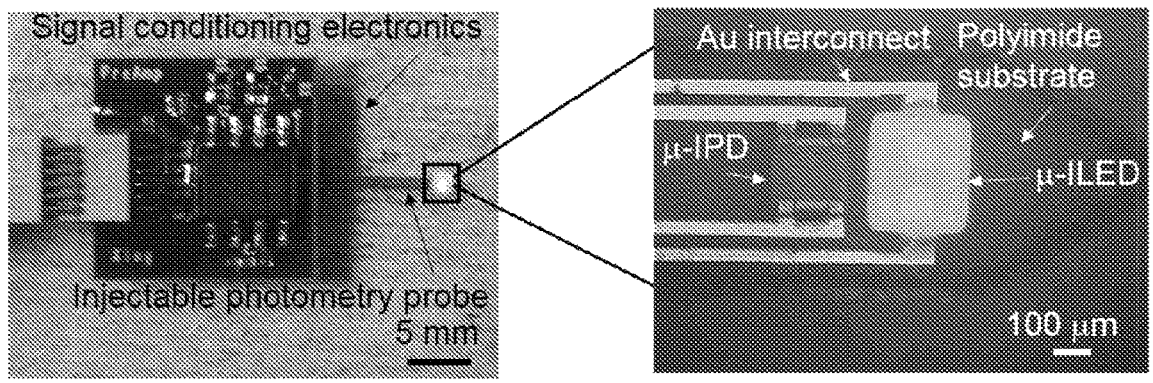
FIG. 20. Image of a prototype injectable photometry probe, with head-mounted signal conditioning electronics and wired interface (left). The probe supports a μ-IPD for detecting fluorescence induced by stimulation from the output of a co-integrated μ-ILED (right).

FIG. 20 highlights the essential features of this demonstration device designed to establish feasibility of this technology approach. This initial system uses signal conditioning electronics on a miniaturized externally mounted head stage (right frame) with a wired connection to external power supplies and data acquisition systems. The tip end of the injectable needle supports an InGaN µ-ILED and a GaAs µ-IPD (right frame). The devices can then be surgically implanted using a standard stereotaxic frame as previously reported for wireless optogenetic probes with similar designs[1].

Figure 21:
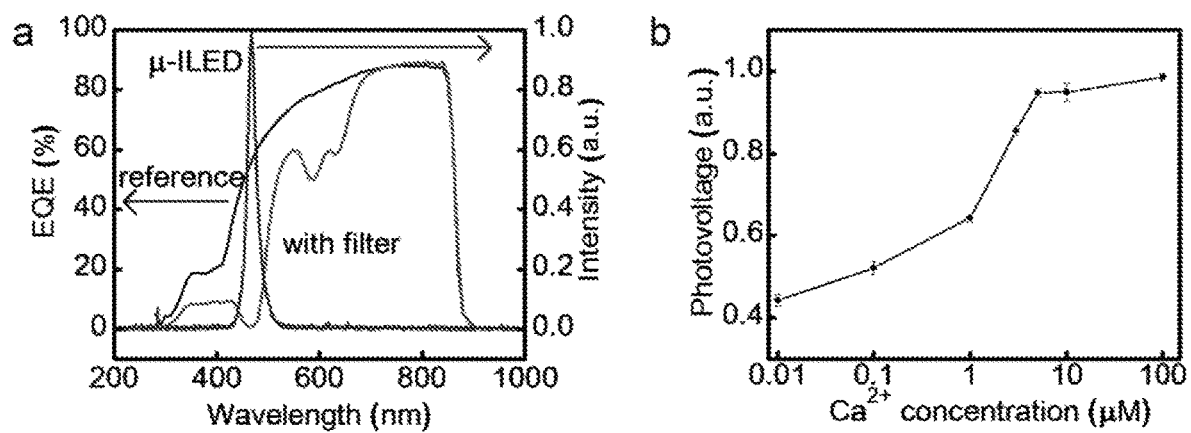
FIG. 21. In vitro measurements of the components of an injectable photometry probe, and functional demonstration. a, μ-ILED output as a function of wavelength (blue curve), external quantum efficiency of the μ-IPD with (red curve) and without (black curve) the integrated optical filter; b, Functional demonstration of an integrated photometry probe for fluorescent detection of $Ca^{2+}$ over a range of concentrations.

FIG. 21a shows the spectral characteristics of emission from the former, where the maximum intensity occurs at 467 nm (blue curve), and the photoresponse of the latter (black and red curves). By utilizing filter formulation with 1 wt % dye concentration, the external quantum efficiency (EQE) of the µ-IPD at 467 nm drops from 57% (µ-IPD without filter) to 0.7% (µ-IPD with filter). The rejection ratio, defined by the ratio of EQE at 470 nm to 488 nm, is 0.05. The high efficiency of the InGaN µ-ILED and its extremely small dimensions allow operation with very low peak increases in the temperature of the surrounding tissue. Infrared image analysis of the probe during operation under a 0.5 mm thick layer of pig fat reveals temperature increases of only ~0.2° C. for emission intensities of 10 mW/mm² (corresponding to ~1 mA current) at 20% duty cycle, and 20 Hz period. This operating condition is suitable for both in vitro and in vivo operation.

Changes in the concentration of $Ca^{2+}$ over a range relevant to neuron activity in the brain can be detected as changes in fluorescence captured using this system, as demonstrated through in vitro experiments using Oregon green@ 488 BAPTA-2 potassium salt (absorption maximum 494 nm/emission maximum 523 nm) as the $Ca^{2+}$ indicator. As shown in FIG. 21b, clear increases in voltage from the µ-IPD accompany increased $Ca^{2+}$ concentrations from 0.01 to 100 µM. The slow increase in photovoltage from 10 to 100 µM corresponds to the saturation in fluorescence of the specific indicator.

To study brain activity in real-time on awake, behaving animals using a platform of injectable µ-ILEDs and µ-IPDs, with a focus on fear conditioning responses. Rationale: The BLA is significantly involved in both the formation of fear and memory. Neurons are activated in BLA during fear conditioning. The system described above will be used to detect the fluorescence signal from neuron activity in BLA under fear conditioning behavior experiments. The results will allow further optimization of the µ-ILEDs and µ-IPDs and the overall design of the system.

Figure 22:
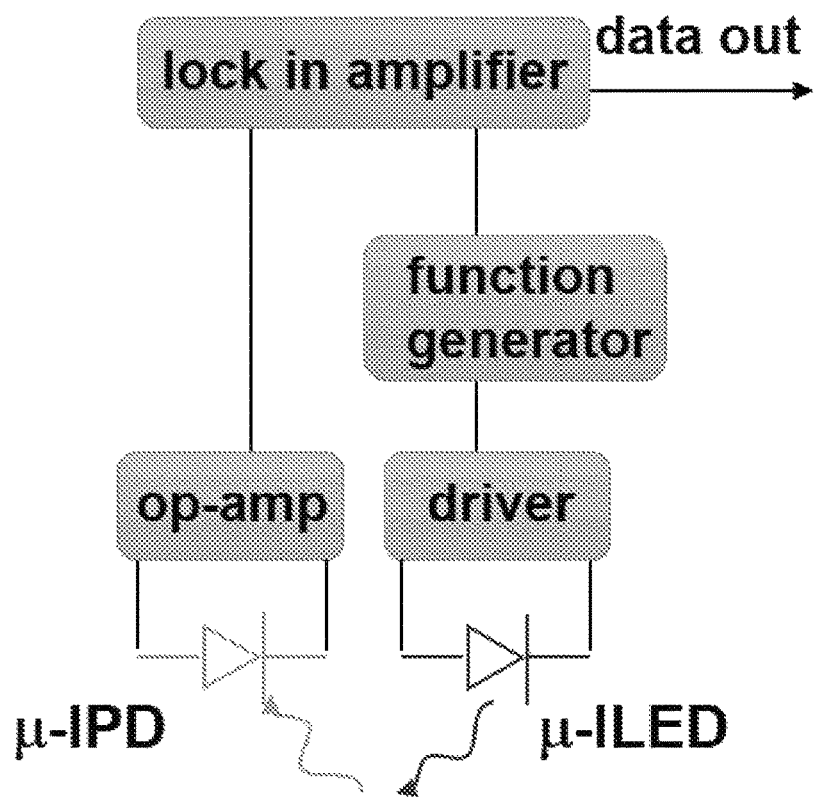
FIG. 22. Schematic illustration of the data acquisition approach. The system includes a μ-ILED operated in pulsed mode and a μ-IPD whose output is captured via lock-in detection.

Fabrication of injectable photometry systems for efficient detection of changes in fluorescence associated with neural activity. Preliminary experiments (FIG. 21) demonstrate that existing devices can accurately detect changes in $Ca^{2+}$ concentration changes in vitro. Here, advanced integration techniques allow co-location and electrical interconnection of independently fabricated µ-ILED and µ-IPD components with lithographically defined, microscale (sub-mm) dimensions onto thin, filamentary substrates of polyimide. Encapsulation with a trilayer of $Al_2O_3$ (100 nm) and parylene (10 µm) and polydimethylsiloxane (2 µm) ensures robust operation for ~30 days at physiological conditions, as determined from accelerated lifetime testing in phosphate buffered saline solution. This work enhances and extends the capabilities of these systems by 1) optimizing the layouts to maximize the signal to noise ratios and to minimize any motion artifacts 2) further miniaturizing the dimensions of the components and the overall injectable platforms. A recording system is illustrated in FIG. 22. Experimental Design: We optimize the optical filter for the µ-IPD and the positioning of this component to increase the extent of rejection of direct illumination from µ-ILED and to improve the efficiency of capture of fluorescent light. To reduce the overall size, the µ-IPDs will be formed with dimensions of 100×100 µm and the µ-ILEDs will be rotated by 180 degrees, such that their wide dimension aligns with the long axis of the probe. The metal interconnect traces will be narrowed to 50 µm. Further miniaturization is achieved with multilayer layouts similar to those reported in wireless, injectable devices for optogenetics[1]. The collective result of these modifications is a total device platform with a width less than 300 µm, with options for including an additional layer to accommodate a µ-IPD to measure the light output of the µ-ILED for signal normalization. In all cases, the devices have excellent flexibility, by consequence of the small thickness (75 µm) of the polyimide substrate and the thin device geometries.

Figure 23:
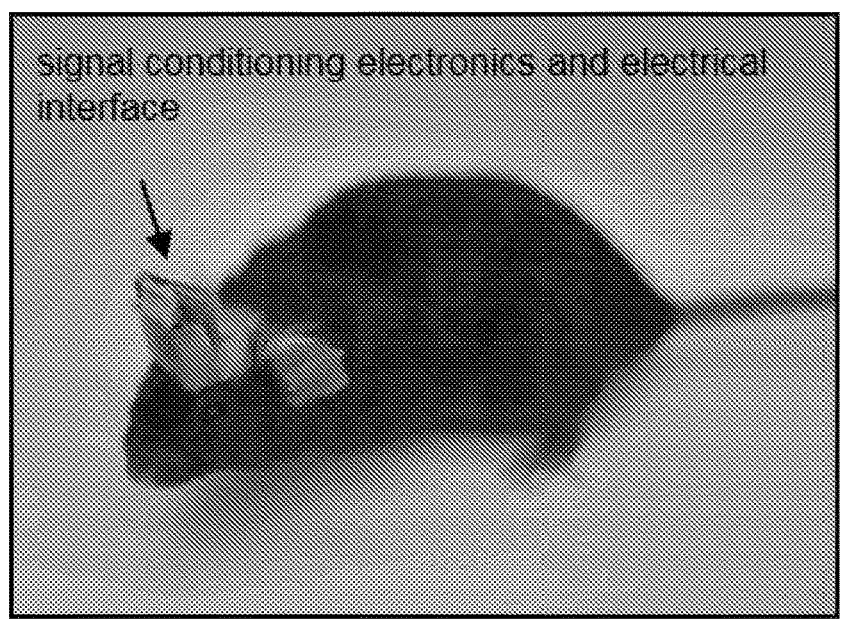
FIG. 23. Mouse with an injectable photometry probe inserted into the BLA region.

Demonstration of controlled stimulations of mouse activities result in changes in fluorescence that can be measured with probes inserted into targeted regions of the brain. Preliminary experiments establish the feasibility of using the full, wired hardware embodiments of FIG. 19 and FIG. 21 in live animal studies (FIG. 23). Systematic animal studies define the detailed performance characteristics.

Figure 24:
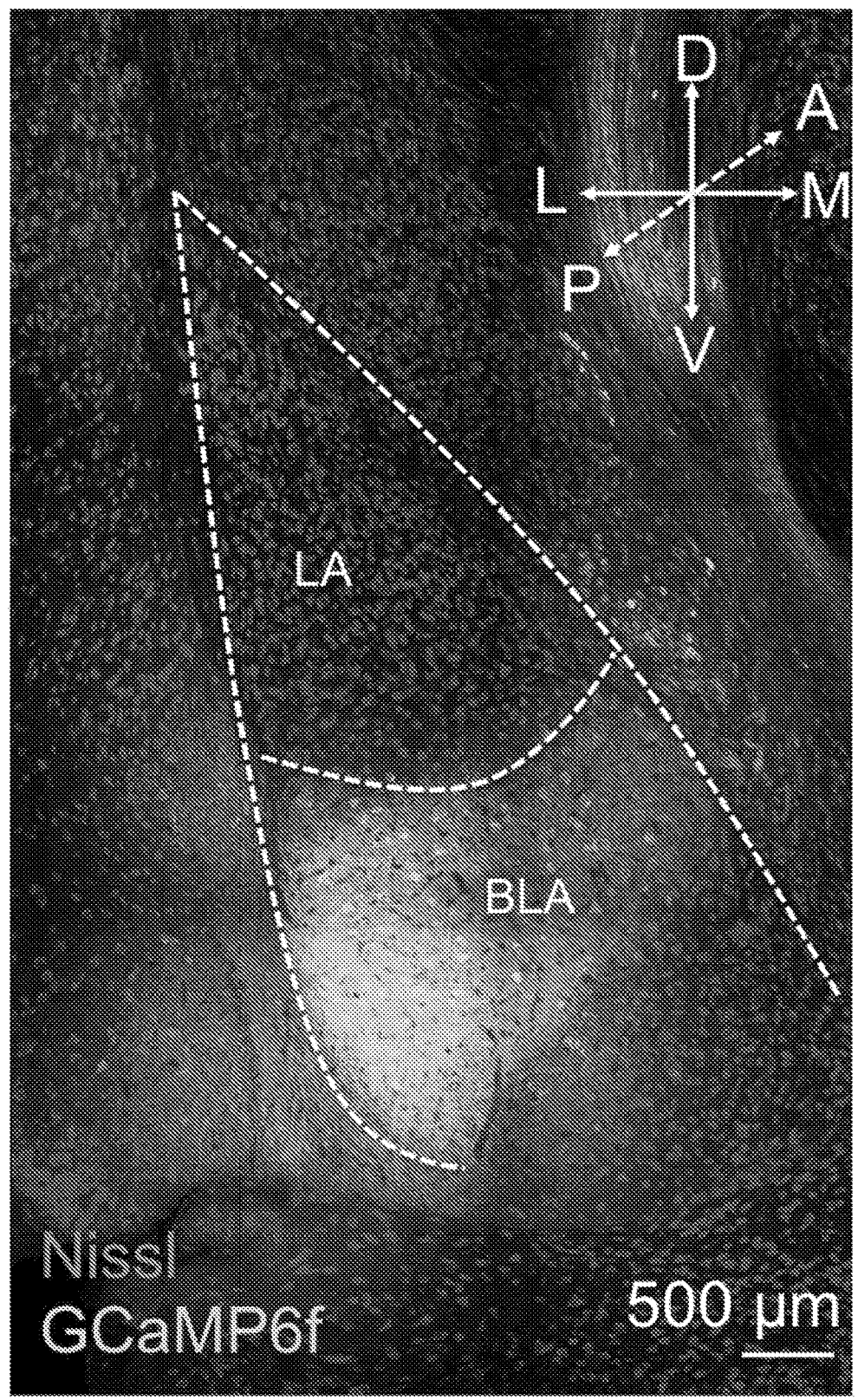
FIG. 24. AAVDJ-GCaMKII-CaMP6f expression in BLA after three weeks.

Experimental Design: AAVDJ-CaMKII-GCaMP6f (m, s, also) will be injected into BLA (−1.6 mm from Bregma, 3.15 mediolateral, −5.2 mm dorsoventral) (FIG. 24), and two weeks later the wired probe will be implanted into the same region. Both the µ-IPD and µ-ILED will be positioned in BLA. Another control group of mice without GCaMP6 in the BLA (AAV5-DJ-GFP control virus) will be implanted using the same device in the same BLA region. Mice will stay at their home cage for 1-2 weeks to recover from the surgery and to habituate to the device. Pavlovian fear conditioning is typical conditioning fear behavioral paradigm in which an initially neutral cue (conditioned stimulus, CS) is paired with an aversive stimulus (unconditioned stimulus, US), leads to a fear unconditional response (UR). Following the training day, the subject will provide a fear conditioned response (CR) with CS alone.

Figure 25:
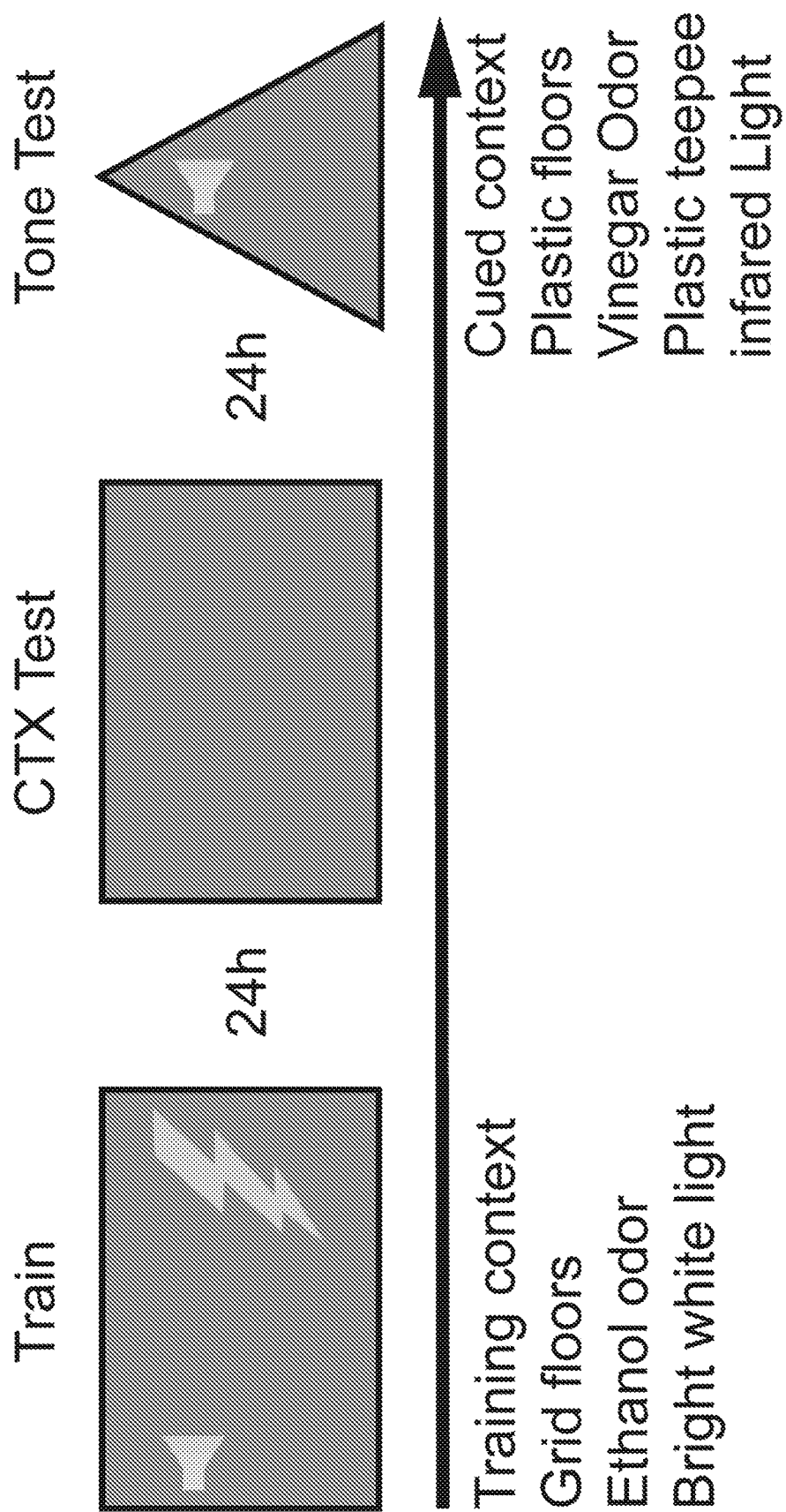
FIG. 25. Summary of Pavlovian fear conditioning experiment. In the training day the mouse will receive a tone paired with footshock. In the context test day, mice will be returned to the conditioning box 24 hours later for a contextual fear test for 5-10 minutes. On a third day, cued fear will be assessed in a novel context by presenting the mice with the training tone.

In the training day, the experiment is paired with training context (grid floors, ethanol odor, bright white light). In the experiment, after 2 minutes recording for the baseline, mice with wired probes will receive four pairings between a tone and shock using a delay (shock at tone offset) or trace (shock occurred 20 s after tone offset) protocol in FIG. 25.

On the next day, mice are placed into the training context (without the tone and shock) for a test of context-elicited fear. On the third day, mice will be placed into a novel context for a test of tone-elicited fear (without the shock). A control group of mice will also go through the same process except in the training day, shock is delivered randomly unpaired with the tone. In context test and tone test day, animals' immobility will be measured. The experimental group should show a high freezing behavior and high amygdala activity in the training day after foot shocks, as well as in context test and tone test day. However, the control group mouse should show low freezing behavior and low amygdala activity in tone test day.

Baseline fluorescence is established as the first 2 minutes recording without the shock. The fluorescence signal is recorded during all the behavior. The neuronal activity is captured and analyzed. The threshold will set up as the median value (med) of the baseline and all the local maximum values larger than 3×med are defined as a neuronal activity event. The duration, number and frequency of events are calculated. The control group mice will go through the same procedure with the experimental group mice. Using a separate group of parallel experimental group, a modified fiber photometry approach as recently described[4,6] will be used. Direct comparisons will be made of: i) the baseline stability, ii) artifacts iii) signal detection and iv) dynamic range.

This will serve as a benchmark for successful measurement of calcium transient activity in awake, freely moving mice with a recently established tethered approach. Following experimentation in the behavioral models, all animal brains will be perfused and examined using IHC approaches[3] to examine for gliosis, lesions, and expression of the GCaMP6 in the approach confines of the BLA region.

Results are compared from an injectable system to those from conventional fiber optics to benchmark performance. The following in side-by-side experiments will be compared: i) baseline fluorescence ii) dynamic range iii) signal reliability and stability over time. This will allow for evaluation of how carefully calcium transient activity can be detected by the present systems as compared to the working fiber photometry systems that some labs are now using[5,9].

Figure 26:
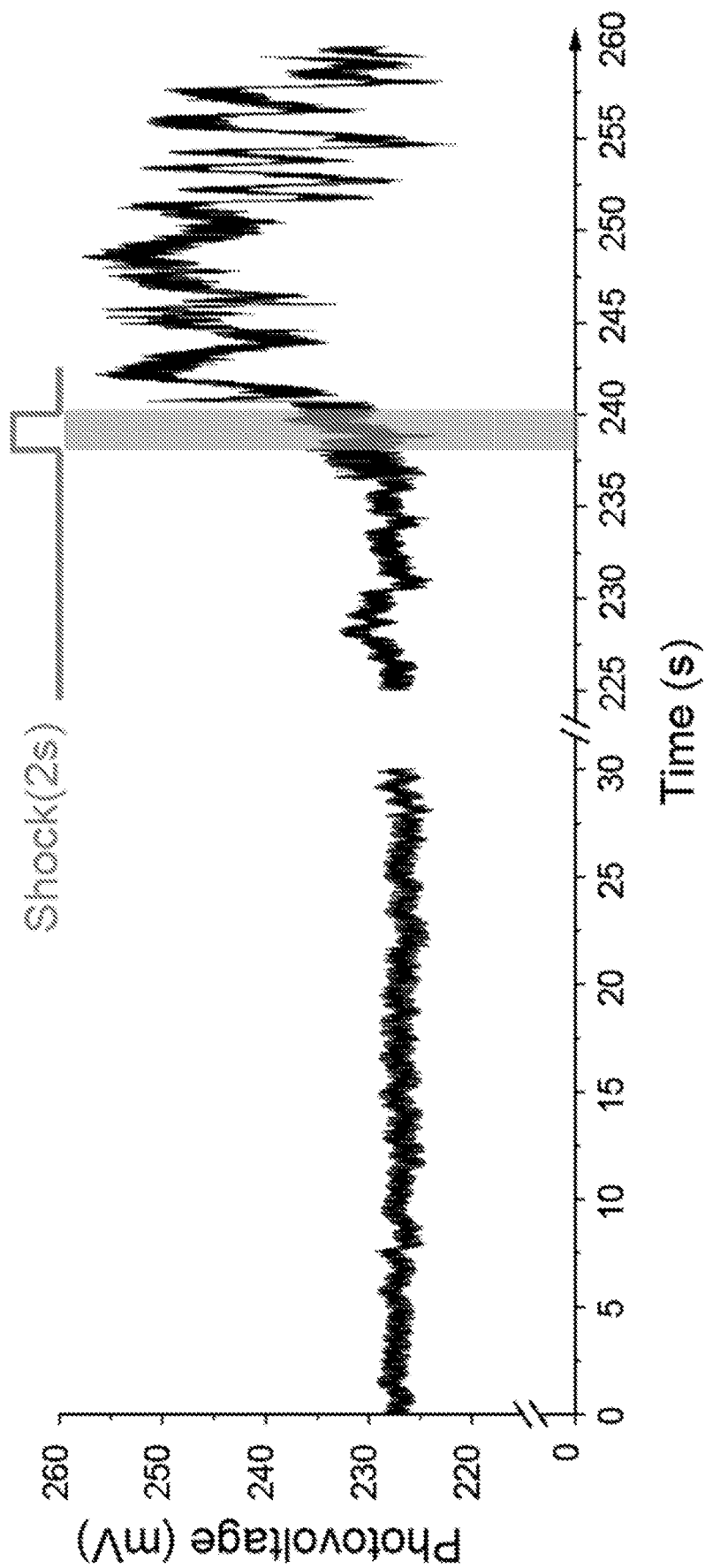
FIG. 26. Preliminary data recorded from the training day. Including a 30 seconds baseline and followed by a 35 second foot shock period (15 seconds before and 20 seconds after). The shock was delivered at 238 s and lasted for 2 seconds.

FIG. 26 shows preliminary data from a training day recording. It shows 30 seconds baseline recording and 30 seconds shock period recording (15 seconds before and 20 seconds after the shock). The shock lasted for 2 seconds. The neuronal activity in BLA was clearly recorded after the foot shock. The amplitude increased by 15% compared with the baseline, and also more spikes showed up. This activity lasted for more than 20 seconds.

To develop wireless schemes for power delivery and data communication for these systems, with demonstrations in fear conditioning and social interaction.

We develop and test wireless photometry schemes. Rationale: Compared to wired devices, wireless probes will greatly reduce motion artifacts and improve the freedom of motion of the animals. Experimental design: NFC technologies will provide capabilities in wireless power delivery, control and data transfer. To calibrate against subtle, motion/orientation induced changes in wirelessly delivered power, the current passing through the µ-ILED and/or of the response of an additional µ-IPD with a filter for selective measurement of light at 467 nm will be wirelessly recorded (FIG. 19a). Advanced versions of a recently reported wireless, implantable potentiostat[7] will serve as the platform for collecting this calibration data as well as the output of the µ-IPD designed to measure the induced fluorescence. This system includes a magnetic loop antenna, passive components (capacitors, resistors) and an advanced NFC logic chip (RF430FRL152H, Texas Instruments, USA; 4 mm×4 mm×300 µm), all supported by a thin, flexible polymer substrate to allow sub-dermal implantation (FIG. 19b). Inductive coupling to an external reader provides dual functions in power transfer and in data collection with operating frequency of 13.56 MHz and a range of ~1 m. The system enables maximum sampling rate of 250 Hz with mV sensitivity, as proven in the inventors' earlier work on wireless ICP measurements (FIG. 19c). Separate publications demonstrate the ability to wirelessly transfer power at levels that meet requirements to drive stimulating µ-ILEDs[10]. This work will involve reconfiguring this system for present purposes, and performing demonstrations in animal behavior tests as outlined in aim 2b.

We develop and test wireless schemes in home cage social interaction experiments. Rationale: In order to test the function of fully wireless photometry within a behavioral task that explicitly benefits from wireless operation, we will measure social interaction behavior while recording transient neuronal activity within the BLA. The basolateral amygdala is a well-known nucleus for the mediation and integration of social behaviors[11,12]. We will conduct a series of novel social interaction experiments to measure the neuronal activity of excitatory BLA neurons (CaMK$^{2+}$ cells) using a modified sociability task[12,13,14], in the home cage. Mice are allowed to freely roam a plastic box for 10 minutes. A novel, sex- and age-matched conspecific will then be added to one of the inverted cups in a random, counterbalanced manner. Using dual animal tracking algorithms (Noldus), the social interactions can be defined. The test mouse was then reintroduced to the chamber and the time spent interacting is recorded. Photometry measures will be time stamped using a TTL pulse from Noldus to the acquisition of calcium transients. The BLA is known to be involved in novel context as well as novel social interaction, so control groups for novel objects will also be compared using the basic model.

Risks and mitigation strategies for device implementation: Risk #1: Even with the calibration approaches described above, wireless delivery of power may involve fluctuations that add significant variability to detected signals. Mitigation #1: We will exploit the battery power option that is supported by our NFC chip, and move the associated hardware to a head-mounted stage. Risk #2: The optical filter for the µ-IPD may provide insufficient rejection of non-fluorescent light. Mitigation #2: We will add on top of this filter a narrow-band multilayer reflector consisting of a combination of $Si_3N_4$ (6 layers in total, 51 nm thick for each layer) and SiO$_2$ (5 layers in total, 72 nm thick for each layer) to enhance the rejection of light at 470 nm (by ~3 times) while maintaining high transmission of >90% at 520 nm. Risk #3: For in vivo operation, the detectivity of the μ-IPD may require improvement for high quality signal collection. Mitigation #3: We will increase the μ-IPD collection area. The risks and mitigation strategies are summarized in Table 1.

TABLE 1

Risks and Mitigation Strategies

| Risks | Mitigation Strategies |
|---|---|
| Unstable power delivery | Using battery as the power supply |
| Insufficient light filtering from μ-ILED | Addition of narrow-band multilayer reflector |
| Detection quality | Increasing collection area for μ-IPD |

Data collection and statistical analysis: The fluorescence signal will be collected as the amplified photovoltage from the μ-IPD via Matlab and LabView. Photovoltage changes recorded from first 2 minutes in the training day will serve as the baseline, and the data of each mouse will be normalized with its own baseline. We will use mice without virally-mediated expression of GCaMP calcium indicators and fiber-based photometry systems as references for comparison. Also the unpaired group of mice will be used to analyze the long-term fear memory in BLA compared with the experimental group. For behavioral studies and pair-wise comparisons, power analysis (using the Mead equation) is used to determine sample sizes and detect differences between groups. Significance is defined at the p<0.05, data expressed as ±SEM. Unpaired Student's t-tests, 1 and 2-way ANOVAs and post hocs (e.g. Tukey and Bonferroni), Matlab (R2015a), Graph Pad Prism (6.0), and SPSS are used for all data analysis, computation, and statistical comparisons of all imaging data and behavioral effects.

REFERENCES

[1] T.-i. Kim, J. G. McCall, Y. H. Jung, X. Huang, E. R. Siuda, Y. Li, J. Song, Y. M. Song, H. A. Pao, R.-H. Kim, C. Lu, S. D. Lee, I.-S. Song, G. Shin, R. Al-Hasani, S. Kim, M. P. Tan, Y. Huang, F. G. Omenetto, J. A. Rogers, M. R. Bruchas, Injectable, Cellular-Scale Optoelectronics with Applications for Wireless Optogenetics, Science, 2013, 340, 211-216.

[2] S. I. Park, D. S. Brenner, G. Shin, C. D. Morgan, B. A. Copits, H. U. Chung, M. Y. Pullen, K. N. Noh, S. Davidson, S. J. Oh, J. Yoon, K.-I. Jang, V. K. Samineni, M. Norman, J. G. Grajales-Reyes, S. K. Vogt, S. S. Sundaram, K. M. Wilson, J. S. Ha, R. Xu, T. Pan, T.-i. Kim, Y. Huang, M. C. Montana, J. P. Golden, M. R. Bruchas, R. W. Gereau IV, J. A. Rogers, Soft, stretchable, fully implantable miniaturized optoelectronic systems for wireless optogenetics, Nature Biotechnology, 2015, 33, 1280-1286.

[3] J.-W. Jeong, J. G. McCall, G. Shin, Y. Zhang, R. Al-Hasani, M. Kim, S. Li, Joo Y. Sim, K.-I. Jang, Y. Shi, D. Y. Hong, Y. Liu, G. P. Schmitz, L. Xia, Z. He, P. Gamble, W. Z. Ray, Y. Huang, M. R. Bruchas, J. A. Rogers, Wireless Optofluidic Systems for Programmable In Vivo Pharmacology and Optogenetics, Cell, 2015, 162, 662-674.

[4] L. A. Gunaydin, K. Deisseroth, Dopaminergic dynamics contributing to social behavior. Cold Spring Harbor Symposia on Quantitative Biology, 2014, 79, 221-227.

[5] C. K. Kim, S. J. Yang, N. Pichamoorthy, N. P. Young, I. Kauvar, J. H. Jennings, T. N. Lerner, A. Berndt, S. Y. Lee, C. Ramakrishnan, T. J. Davidson, M. Inoue, H. Bito, K. Deisseroth, Simultaneous fast measurement of circuit dynamics at multiple sites across the mammalian brain, Nature Methods, 2016, doi:10.1038/nmeth.3770.

[6] G. A. Matthews, E. H. Nieh, C. M. V. Weele, S. A. Halbert, R. V. Pradhan, A. S. Yosafat, G. F. Glober, E. M. Izadmehr, R. E. Thomas, G. D. Lacy, C. P. Wildes, M. A. Ungless, K. M. Tye, Dorsal raphe dopamine neurons represent the experience of social isolation, Cell, 164, 617-631.

[7] S.-K. Kang, R. K. J. Murphy, S.-W. Hwang, S. M. Lee, D. V. Harburg, N. A. Krueger, J. Shin, P. Gamble, H. Cheng, S. Yu, Z. Liu, J. G. McCall, M. Stephen, H. Ying, J. Kim, G. Park, R. C. Webb, C. H. Lee, S. Chung, D. S. Wie, A. D. Gujar, B. Vemulapalli, A. H. Kim, K.-M. Lee, J. Cheng, Y. Huang, S. H. Lee, P. V. Braun, W. Z. Ray, J. A. Rogers, Bioresorbable silicon electronic sensors for the brain, Nature, 2016, 530, 71-76.

[8] J. M. Moscarello, J. LeDoux, Diverse effects of conditioned threat stimuli on behavior. Cold Spring Harbor Symposia on Quantitative Biology, 2014, 79, 11-19.

[9] E. S. Calipari, R. C. Bagot, I. Purushothaman, T. J. Davidson, J. T. Yorgason, C. J. Peña, D. M. Walker, S. T. Pirpinias, K. G. Guise, C. Ramakrishnan, K. Deisseroth, E. J. Nestler, In vivo imaging identifies temporal signature of D1 and D2 medium spiny neurons in cocaine reward, Proceedings of the National Academy of Sciences, 2016, 113, 2726-2731.

[10] J. Kim, A. Banks, Z. Xie, S. Y. Heo, P. Gutruf, J. W. Lee, S. Xu, K.-I. Jang, F. Liu, G. Brown, J. Choi, J. H. Kim, X. Feng, Y. Huang, U. Paik, J. A. Rogers, Miniaturized Flexible Electronic Systems with Wireless Power and Near-Field Communication Capabilities, Advanced Functional Materials, 2015, 25, 4761-4767.

[11] A. C. Felix-Ortiz, A. Beyeler, C. Seo, C. A. Leppla, C. P. Wildes, K. M. Tye, BLA to vHPC inputs modulate anxiety-related behaviors, Neuron, 2013, 79, 658-664.

[12] E. R. Siuda, R. Al-Hasani, J. G. McCall, D. L. Bhatti, M. R. Bruchas, Chemogenetic and Optogenetic Activation of Gas Signaling in the Basolateral Amygdala Induces Acute and Social Anxiety-Like States, Neuropsychopharmacology, 2016, DOI: 10.1038/npp.2015.371.

[13] S. Lewis, Only the lonely, Nature Reviews Neuroscience, 2016, doi:10.1038/nrn.2016.26.

[14] J. L. Silverman, M. Yang, C. Lord, J. N. Crawley, Behavioural phenotyping assays for mouse models of autism, Nature Reviews Neuroscience, 2010, 11, 490-502.

Example 3: Device Characterization

Figure 32:
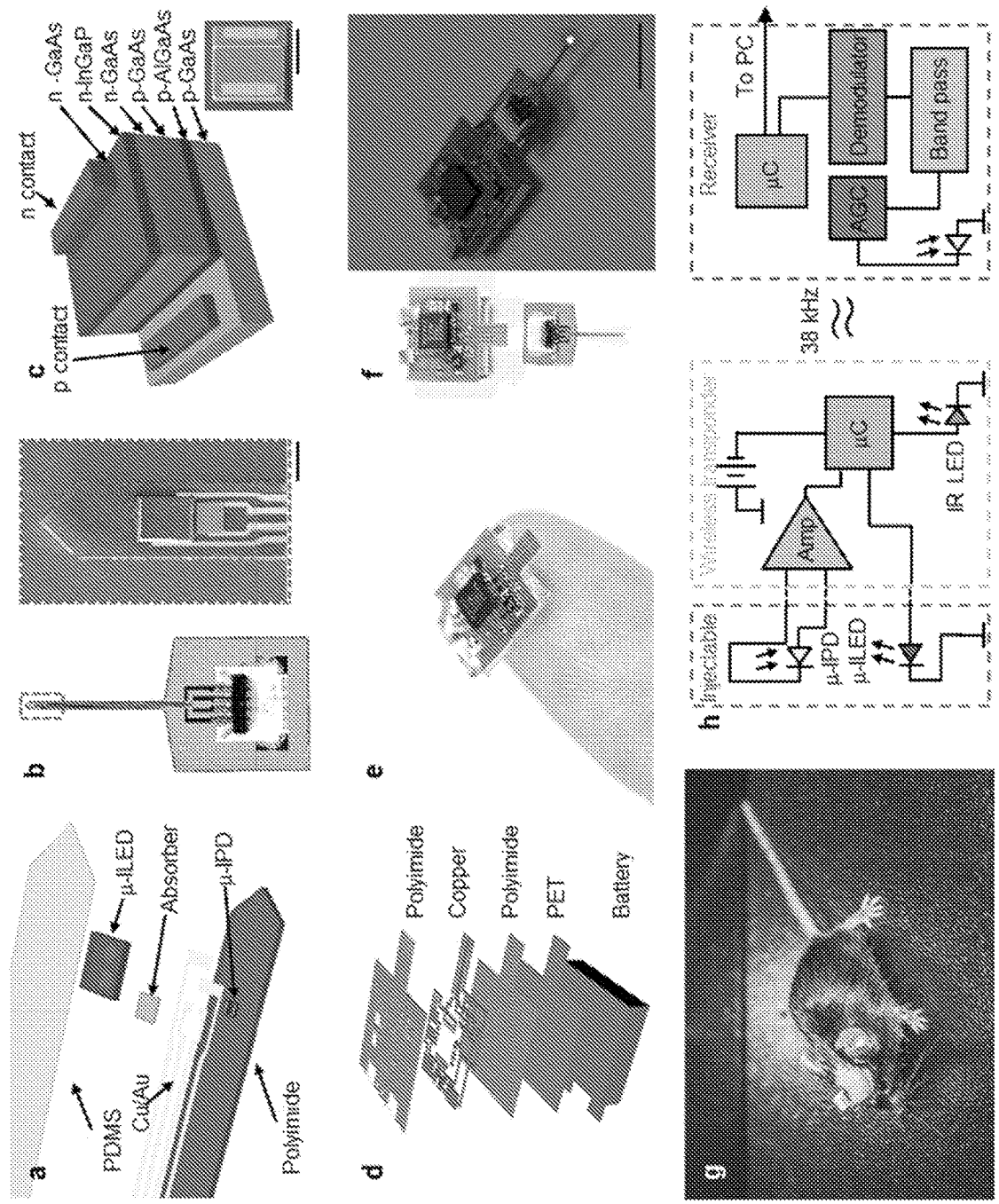
FIG. 32 illustrates miniaturized, ultrathin, lightweight wireless photometry systems for deep brain $Ca^{2+}$ measurements.

FIGS. 32-55 further illustrate the biocompatibility of the devices and in vivo operation. For example, FIG. 32 illustrates a wireless photometry system for deep brain Ca$^{2+}$ measurement. Panel (a) is a schematic exploded-view illustration of a wireless, injectable, ultrathin photometry probe with a μ-ILED and a μ-IPD at the tip end. (b) Optical micrograph of the injectable photometry probe. The tip has a total width of ~350 μm and a thickness of ~150 μm. The weight is 29 mg. (Inset) Magnified colorized SEM image of the tip (orange: polyimide; yellow: interconnection; blue: μ-ILED; green: μ-IPD with an optical filter). Scale bar, 200

μm. (c) Schematic illustration of a GaAs μ-IPD. (Bottom) SEM image of a representative μ-IPD (lateral dimensions of 100×100 mm², and thickness of 5 μm). Metal electrodes are colorized in yellow. Scale bar, 50 μm. (d) Schematic exploded-view illustration of a transponder. (e) Photographic image of the wireless detachable transponder on finger tip. (f) Images of the separated transponder and injectable (left) and the integrated system in operation (right). The transponder is connected only during signal recording. Scale bar, 8 mm. (g) Image of a freely moving mouse with a photometry injectable (1 week after surgery). (h) Schematic of the electrical operation principle of the system.

Figure 33:
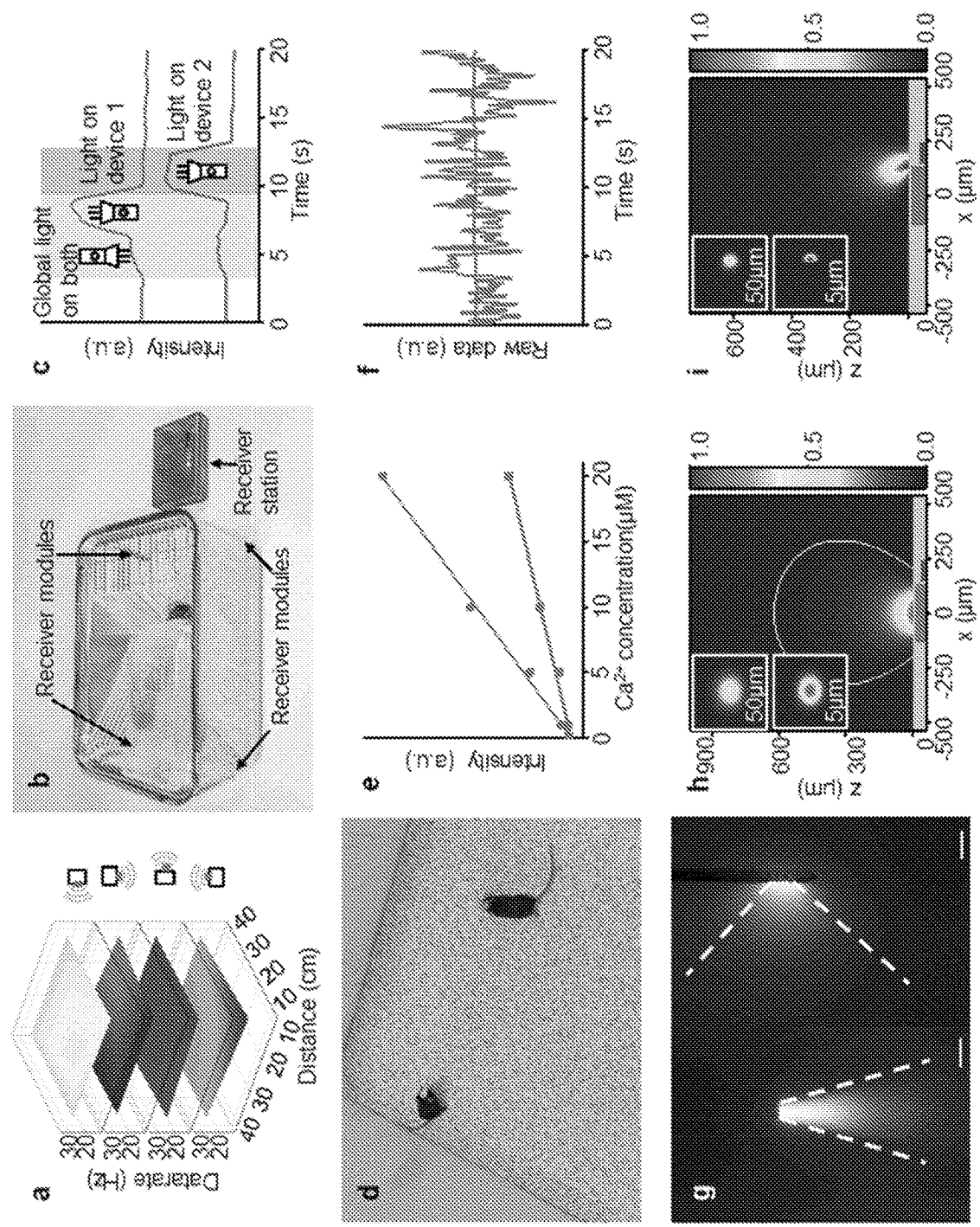
FIG. 33. Electrical and optical properties of wireless photometry systems.

The electrical and optical properties of wireless photometry systems are summarized in FIG. 33. (a) In plane data transmission rates in a 50×50 cm² cage with the transponder facing in various directions. Yellow data set represents west facing transponder, red dataset represents south facing transponder, violet dataset represents east facing transponder, blue dataset represents north facing transponder. (b) A standard mouse home-cage outfitted with the receiver system. (c) Demonstration of simultaneous operation of two wireless photometry systems under an external light source. (green) global light (yellow) light on gray traced device (blue) light on red traced device. (d) Two freely moving mice with wireless photometry systems and housings for simultaneous recordings. (e) Measurement of fluorescence intensity in calcium indicator (excitation maximum: 494 nm; emission maximum: 523 nm) solutions with different $Ca^{2+}$ concentrations (from 0.1 μM to 50 μM) by the fiber optic system (gray) and the wireless photometry probe (red). (f) Fluorescence intensities versus time in the calcium indicator solution with 1 μM $Ca^{2+}$ concentration from the fiber optic system (gray) and the wireless photometry probe (red). (g) Microscopic photograph comparison of the florescence profiles (outlined in white) of a conventional fiber photometry probe (left) and the injectable photometry probe (right). Scale bar, 800 μm. (h) Normalized emission intensity profile with 1% contour for the μ-ILED. (Inset) Emission intensity at positions 5 μm and 50 μm above the encapsulated μ-ILED. (i) Spatial distribution of fluorescence captured by the μ-IPD. (Inset) Fluorescence intensity at positions 5 μm and 50 μm from the top edge (the edge closest to the μ-ILED) of encapsulated m-IPD.

Figure 34:
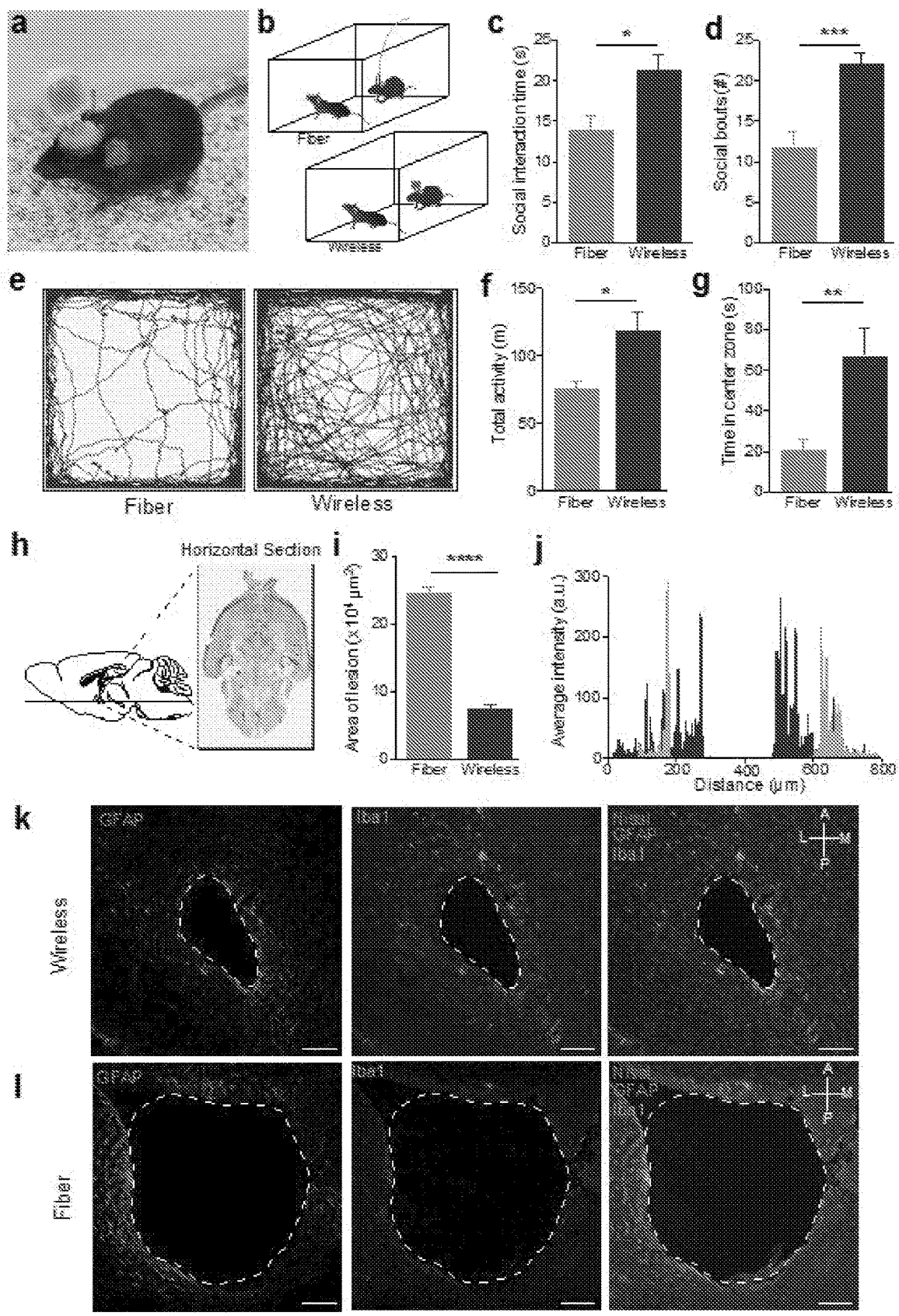
FIG. 34 demonstrates wireless photometry systems for use in awake, freely-behaving mice.
Figure 35:
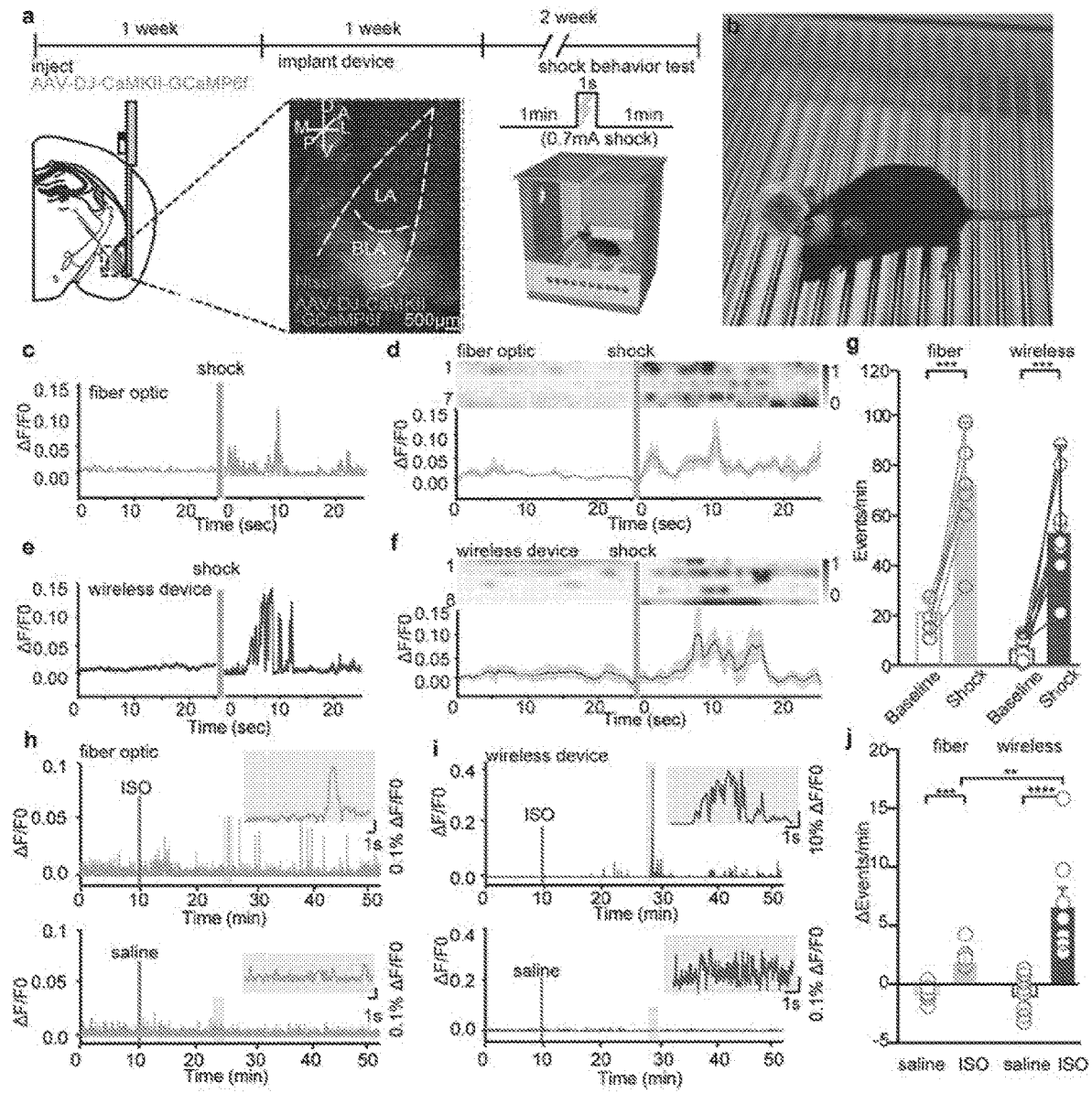
FIG. 35 illustrates a method and related results for wireless in vivo detection of calcium transient activity in the Basolateral Amygdala.

FIG. 34 illustrates use of a wireless photometry system in awake, freely behaving mice. (a) Photographic image of a mouse in behavioral arena with wireless photometry system affixed. (b) Cartoon of social interaction task. (c-d) Mice implanted with miniaturized, lightweight wireless photometry probes display increased (c) social interaction time and (d) number of interaction bouts compared to mice implanted and tethered using traditional fiber photometry systems. (two-tailed t-test, *p<0.05, ***p<0.001, n=9-10/group). (e) Representative traces of total activity in an open field arena for mice implanted for each device. (f-g) Mice implanted with wireless photometry probes display (f) increased traveled distance, a measure of activity, and (g) less time spent in the center zone, a measure of anxiety-like behavior, in the open field compared to fiber-implanted mice (two-tailed t-test, *p<0.05, **p<0.01, n=7-9/group). (h) Schematic and atlas image of the mouse brain at the point of observation of tissue damage for lesion and inflammation measurements from wireless neural probe. (i) Wireless photometry probes lesion less brain tissue compared to traditional photometry probes (two-tailed t-test, *p<0.05, **p<0.01, p=3 slices per mouse, n=3/group). (f) Representative linescan of fluorescence intensity of glial cell markers from traditional and wireless photometry probes. (g-h) Representative confocal fluorescence images of horizontal amygdalar slices. Minimal tissue damage occurs after implantation of both the wireless and fiber photometry probes as shown by immunohistochemical staining of astrocytes (GFAP, red) and activated microglia (Iba1, green). Scale bars, 100 μm.

Figure 36:
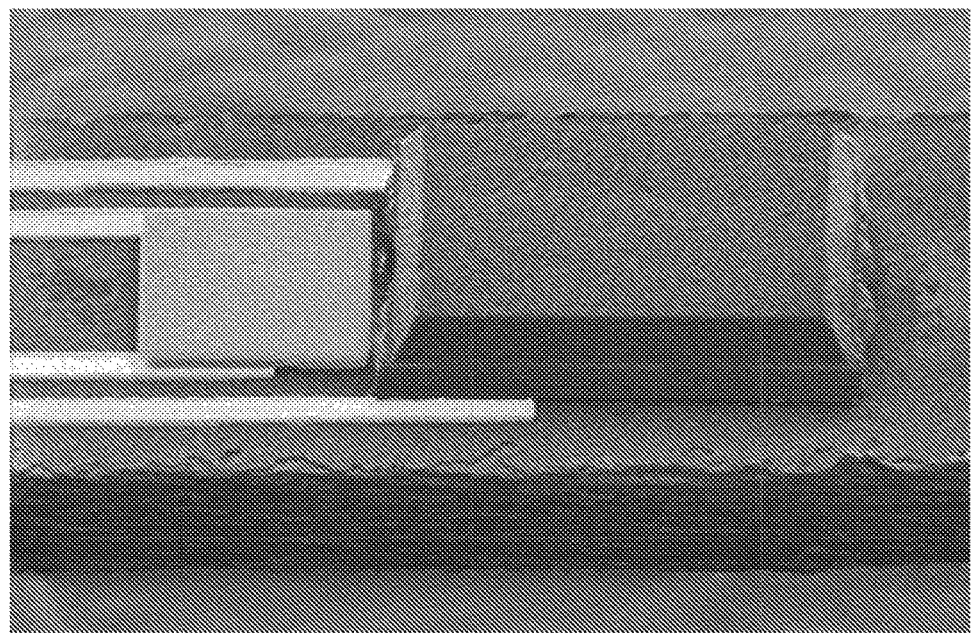
FIG. 36 is a colorized SEM image of a photometer needle. The scale bar is approximately 200 μm.
Figure 37:
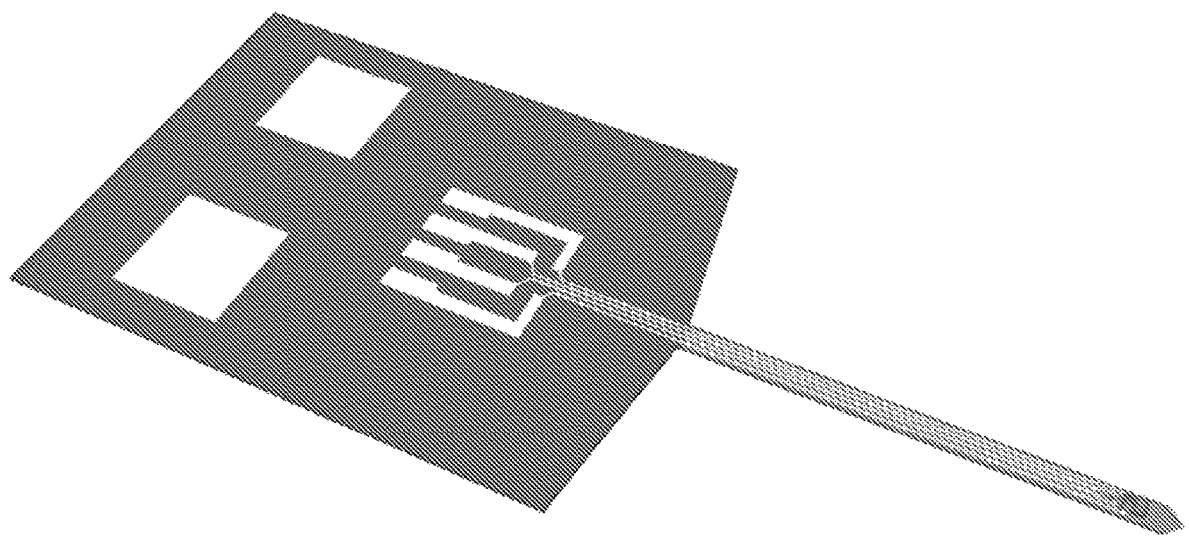
FIG. 37 is a schematic illustration of an intact photometer probe.
Figure 40:
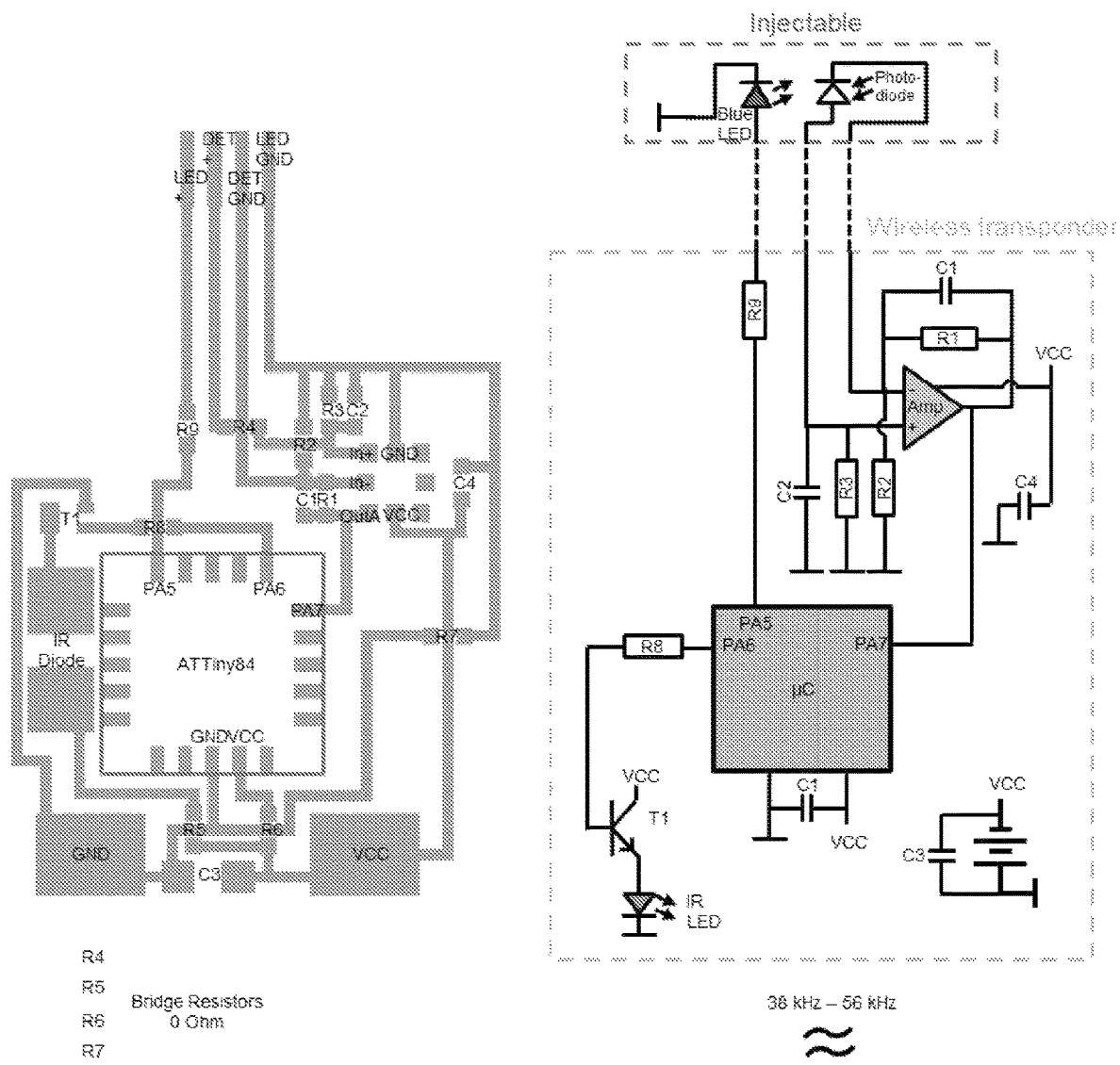
FIG. 40 is a circuit design for wireless photometry transponder and injectable.
Figure 41:
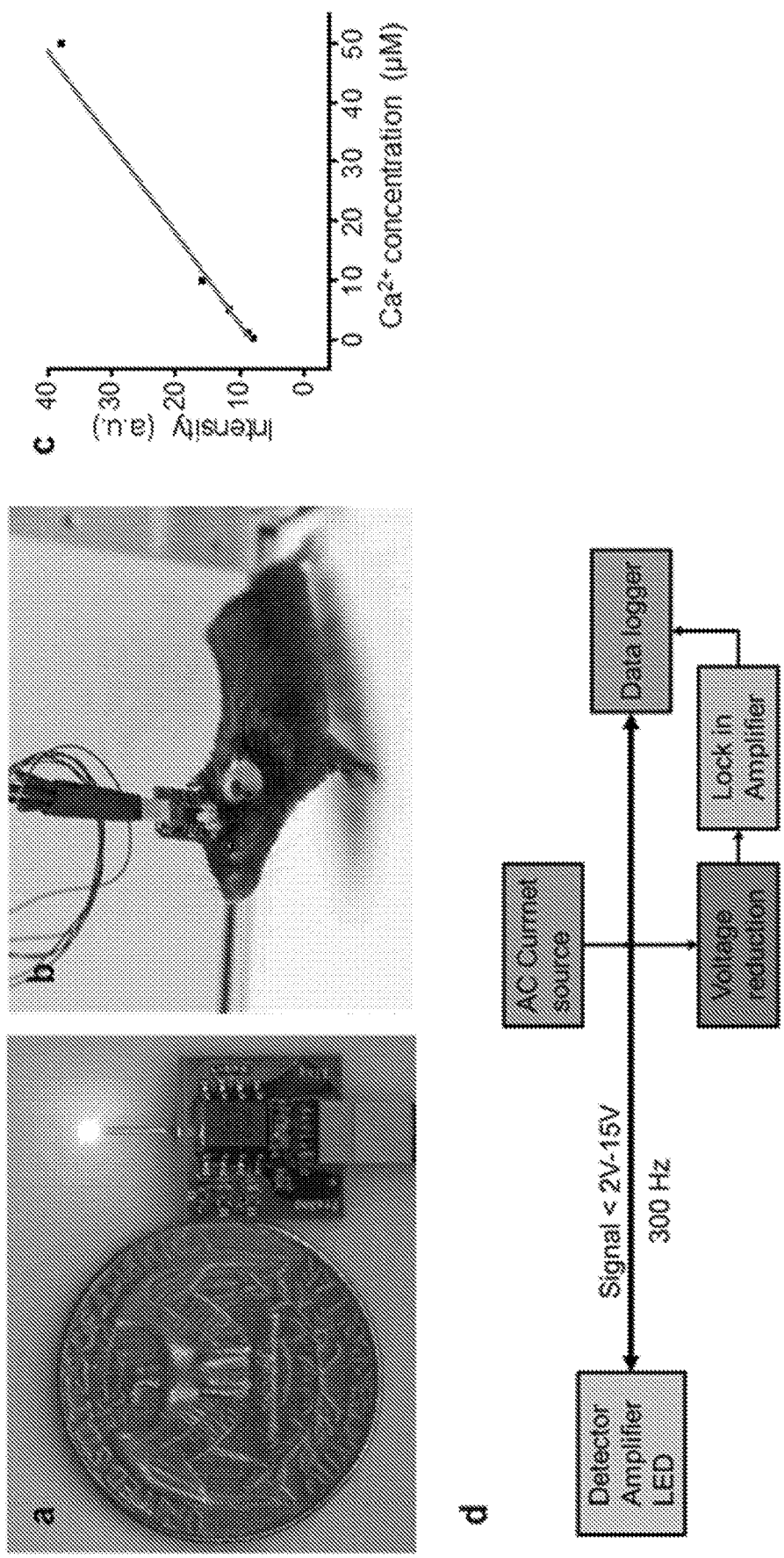
FIG. 41 Panel (a) is a photograph of a wired photometry system next to a US quarter. (b) Photograph of a moving mouse during recording. (c) In vitro measurement of fluorescence intensity changes with different $Ca^{2+}$ concentrations from 0.1 μM to 50 μM by the wired photometry probe. (d) Electronic working principle of the wired photometry system.
Figure 42:
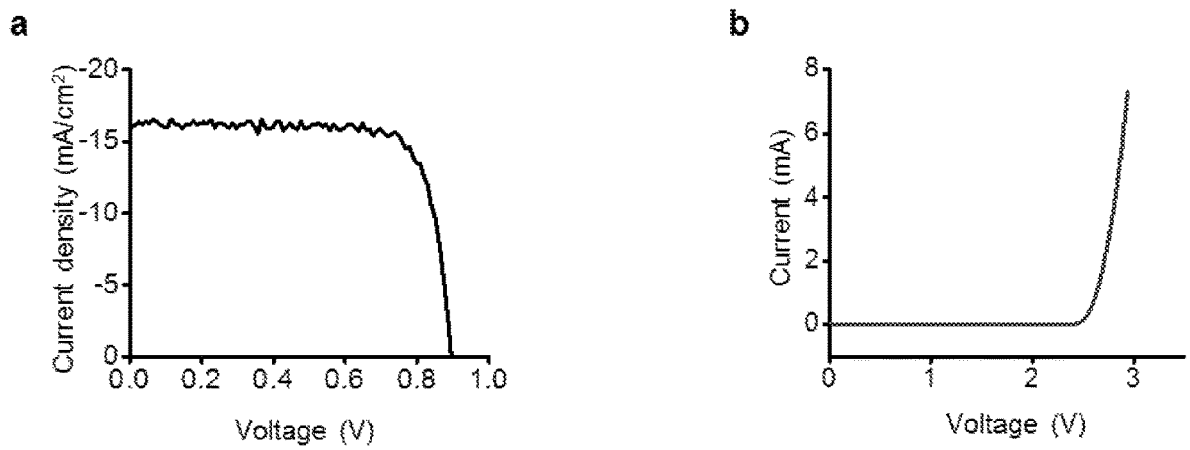
FIG. 42 provides current-voltage characterizations of μ-IPD and μ-ILED. (a) Current density versus voltage curve of a representative μ-IPD. (b) Current versus voltage curve of a representative μ-ILED.
Figure 43:
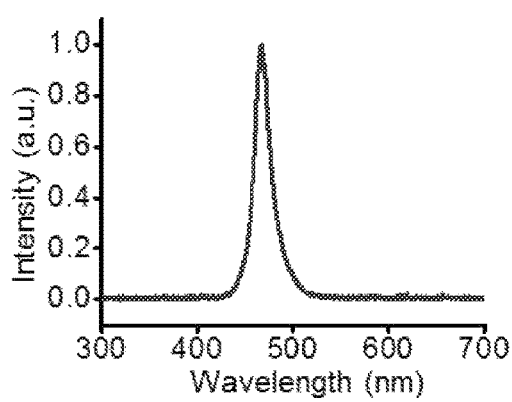
FIG. 43 is an emission spectrum of an operating μ-ILED on the injectable needle.
Figure 44:
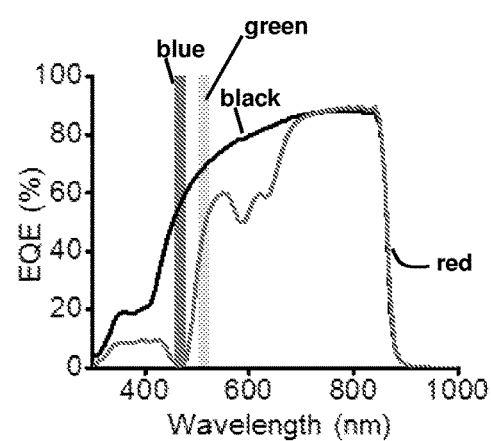
FIG. 44 is an EQE spectra of a μ-IPD with (red) and without (black) a narrow band absorber on top. The blue and green areas highlight wavelength ranges with strong emission from the μ-ILED and fluorescence of GCaMP6f, respectively.
Figure 45:
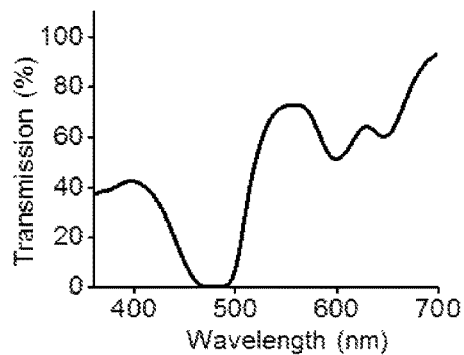
FIG. 45 is a transmission spectrum of 7 μm thick SU-8 with 1.5 wt % absorber.
Figure 46:
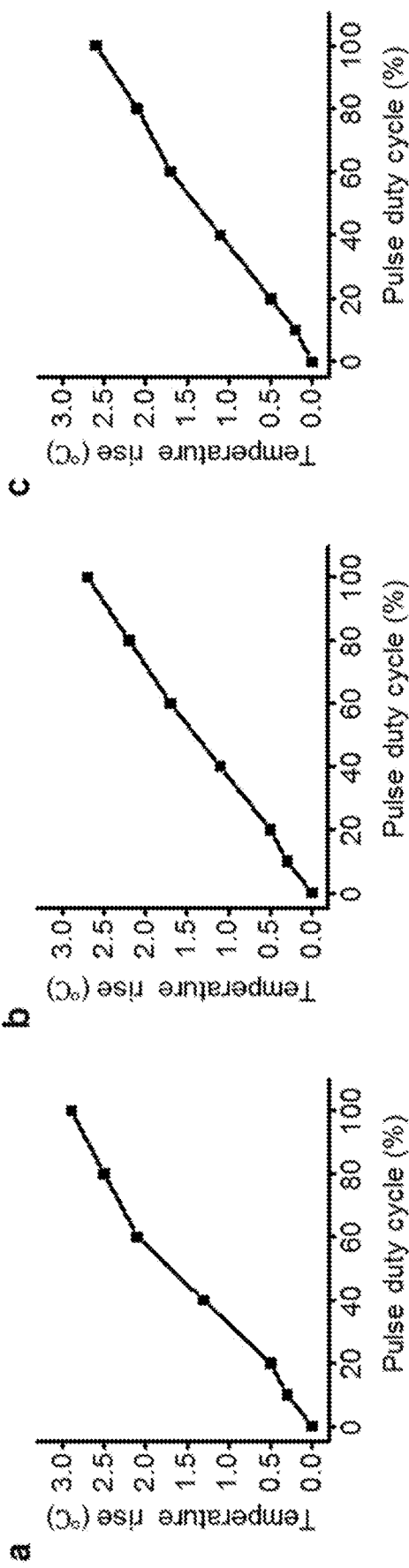
FIG. 46 illustrates temperature changes of the injectable needle under 0.5 mm porcine fat as a function of the μ-ILED operating at different duty cycles under constant output power (10 mW/mm$^2$) and pulse frequencies at 20 Hz (a), 200 Hz (b), and 300 Hz (c). The μ-ILED works at 20% duty cycle in this example.
Figure 47:
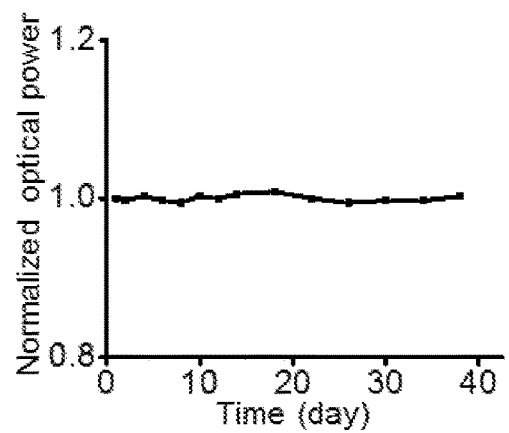
FIG. 47 illustrates normalized photovoltage signals from the μ-IPD at ambient condition as a function time after immersion in phosphate-buffered saline with a temperature of 37° C.
Figure 48:
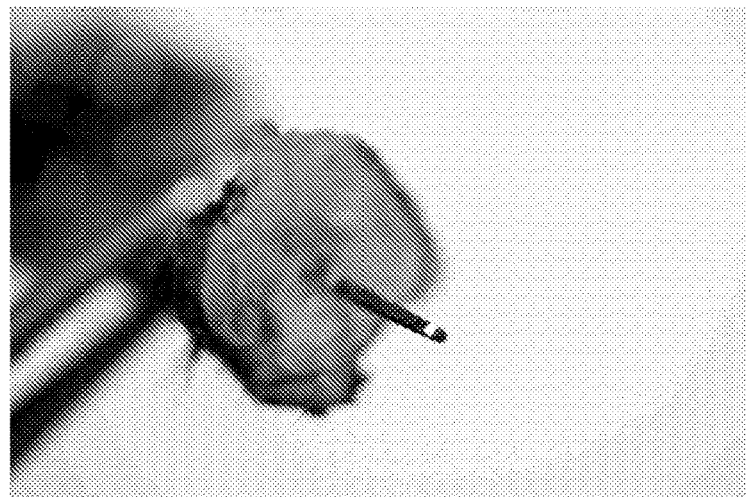
FIG. 48 is an image of a wireless photometry system operating after implanted in BLA region for 2 months FIG. 49 Panel (a) is a wireless receiver station with quad receiver modules. (b) Opened housing for social animal interaction recording.
Figure 49:
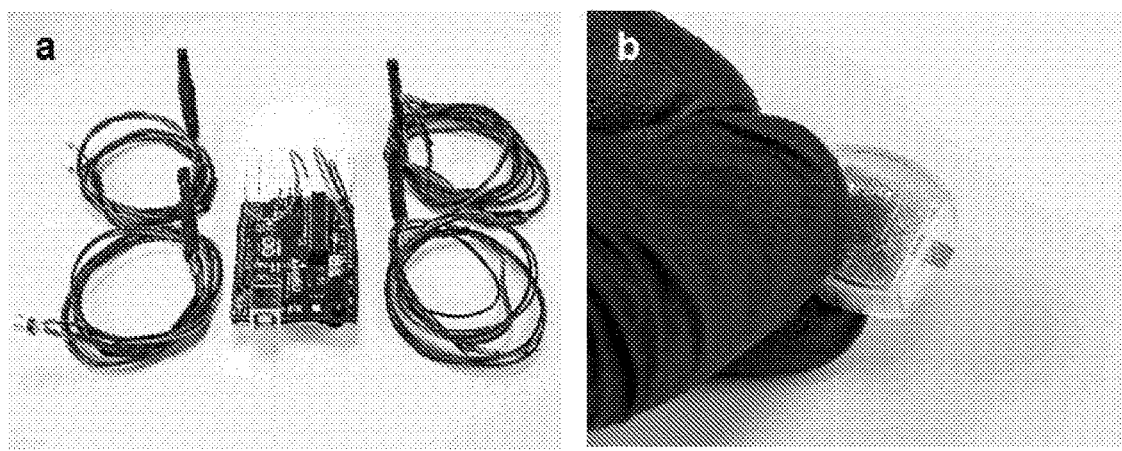
Figure 50:
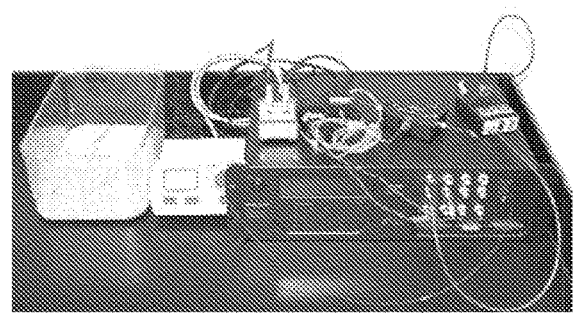
FIG. 50 is an image of the fiber photometry system next to a home-cage.
Figure 51:
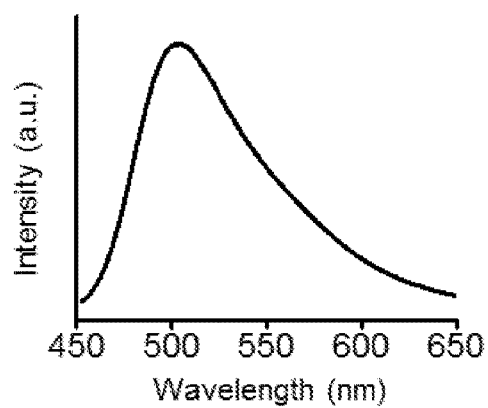
FIG. 51 is a fluorescence spectrum of 0.3 µM Oregon Green® 488 BAPTA-2 calcium indicator mixed with 5 µM $CaCl_2$, excited at 488 nm.
Figure 52:
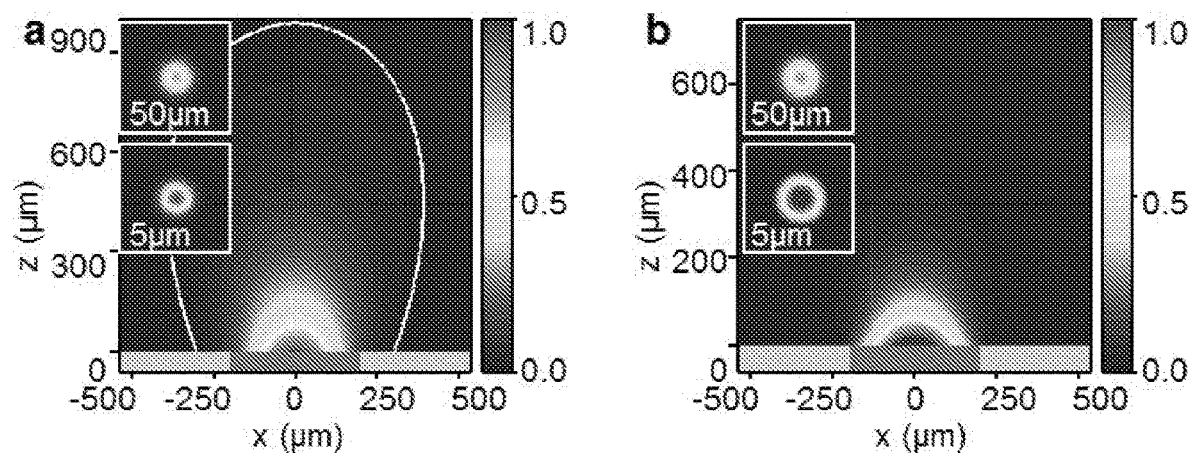
FIG. 52 (a) Normalized emission intensity profile with 1% contour for the optical fiber. (Inset) Emission intensity at positions 5 mm and 50 mm above the optical fiber. (b) Spatial distribution of fluorescence intensity captured at the tip of the optical fiber. (Inset) Fluorescence intensity at positions 5 mm and 50 mm above the tip of the optical fiber.
Figure 53:
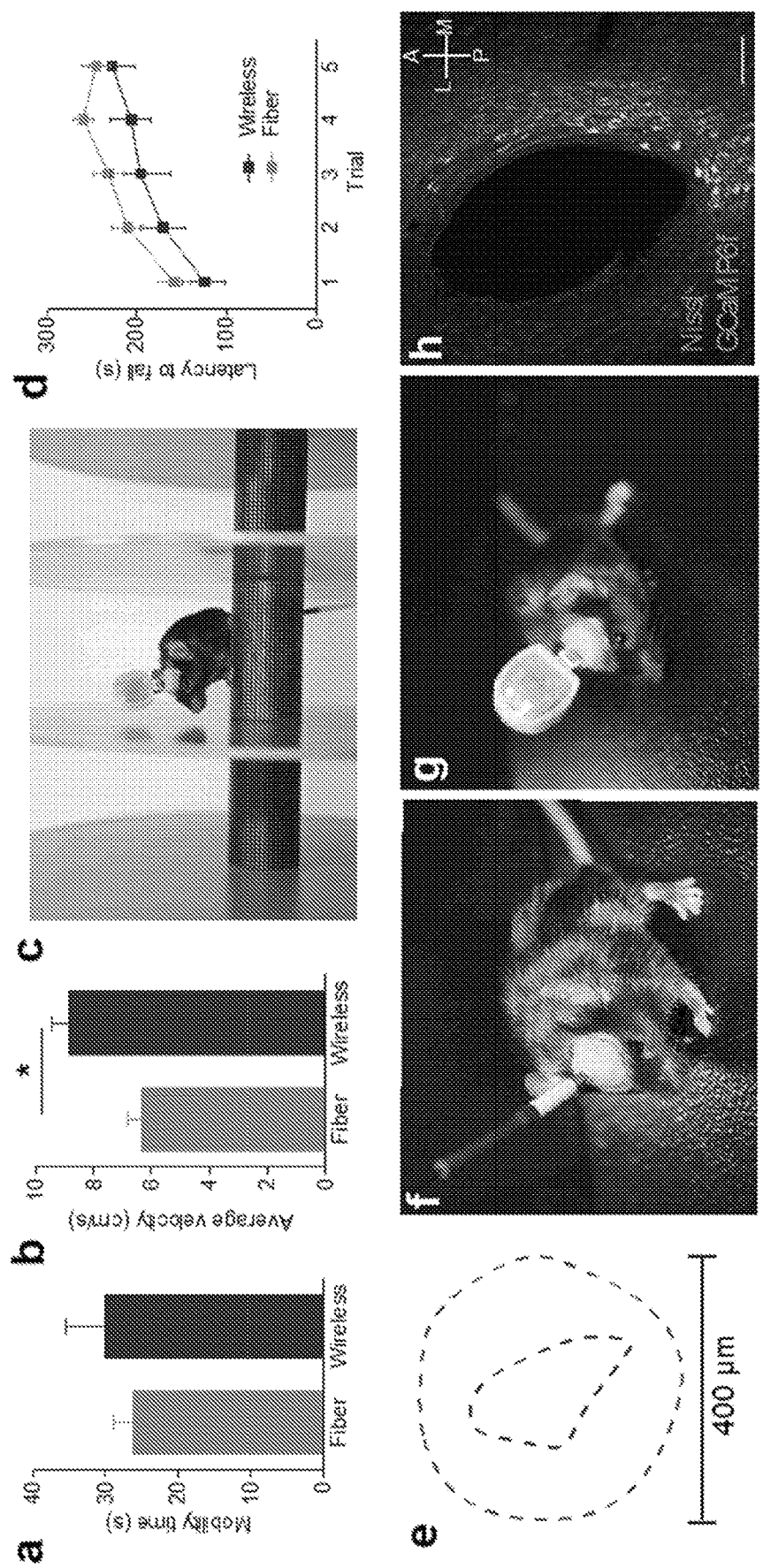
FIG. 53 Wireless photometry systems for neural recordings in freely-behaving animals. (a) Tethered fiber-implanted and tetherless wireless-implanted mice do not differ in the amount of time immobile in the OFT. (b) Wireless-implanted mice have increased velocity during the OFT (2-tailed test, *p<0.05, n=7-9). (c) Photograph of wireless-implanted mouse performing the rotorod task. (d) Chronic implantation of the wireless devices does not alter motor coordination in a rotorod assay (n=8-10/group, 2-way ANOVA, p=0.16). (e) Overlay of lesion areas resulting from chronic implantation (wireless=blue; fiber=grey). (f-g) Photograph of mouse, (f) tethered and implanted with a traditional fiber optic probe or (g) attached to the complete wireless photometry probe. (h) Confocal image of lesion at the site of recording showing expression of calcium indicator GCaMP6f around the site of the wireless photometry probe. Scale bar, 75 µm.
Figure 54:
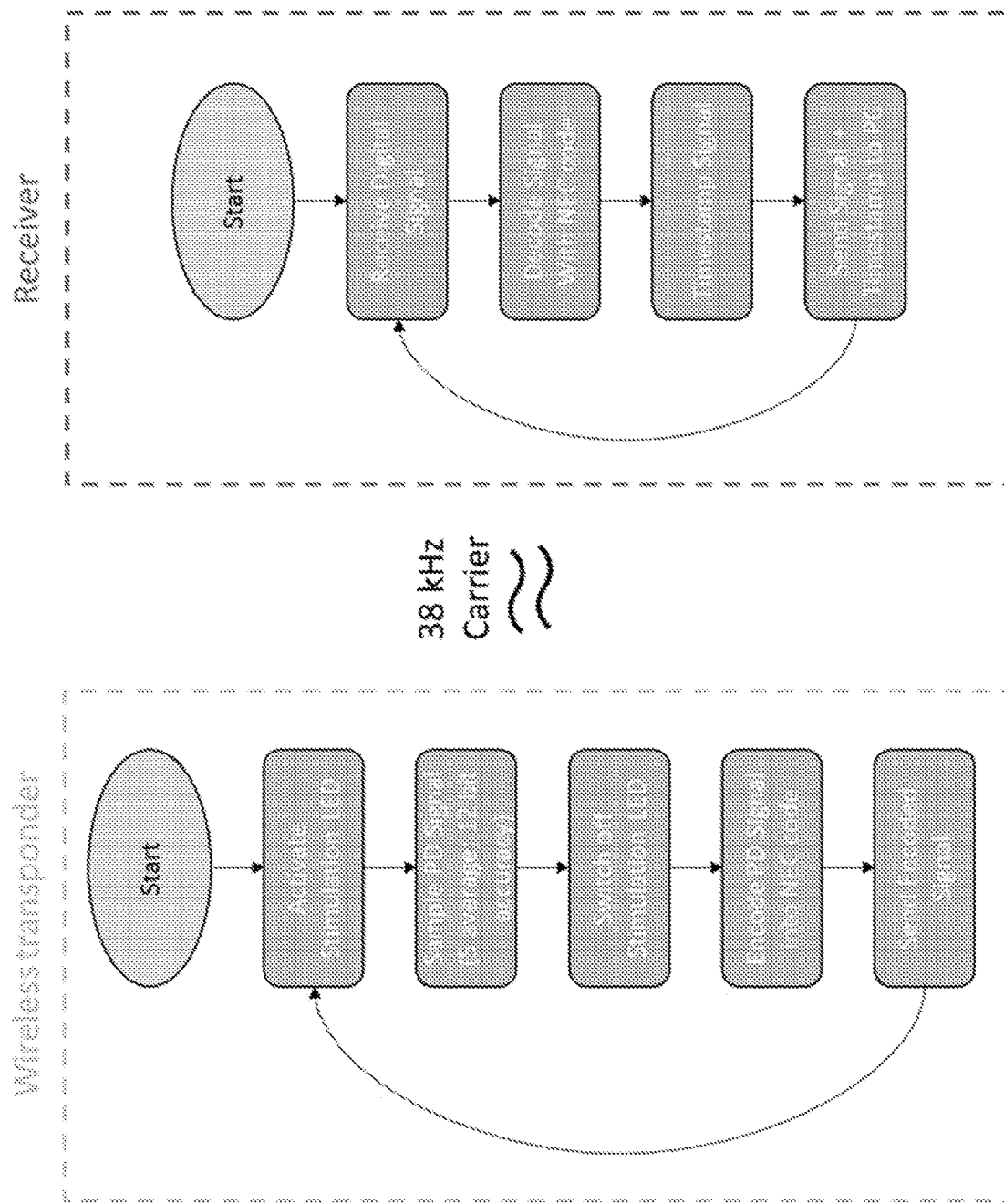
FIG. 54 Program flow for wireless transponder and receiver.

In vivo results of the detection of calcium transient activity in the Basolateral Amygdala is summarized in FIG. 36. a, Upper: timeline of virus injection, device implantation and behavior test. Lower: Schematic of viral delivery and expression of AAV-DJ-CaMKII-GCaMP6f (shown in green) into the basolateral amygdala (BLA) and wireless delivery of 473 nm light; Diagram of shock delivery and cartoon for a mouse with wireless device during behavior in the shock apparatus. b, Freely-moving mice implanted with wireless device in the shock box. c, a sample trace showing fluorescence change prior to and after shock of an animal using the fiber photometry system. d, Heatmap (top) for 7 trails of signals record by fiber optics prior to and after shock, aligned with trace plotted as mean (curves)±s.e.m. (represented as shading around curves). Fluorescence signals are normalized for each trial. Darker colors indicate higher fluorescence signal. e, a sample trace showing fluorescence change prior to and after shock of an animal using the wireless photometry system. f, Heatmap (top) for 8 trails of signals record by wireless device prior to and after shock, aligned with trace plotted as mean (curves)±s.e.m. (shading around curves). g, Spike event frequency in the BLA before (baseline)/after shock in signals recorded by fiber and wireless photometry systems represented by light and dark colors respectively. Post-shock signals (solid bars) have significantly higher event frequency compared with-pre shock signals (open bars) recorded from fiber photometry system (n=7, Paired t-test, $t_{(6)}$=6.978, p=0.0004), and wireless photometry system (n=8, Paired t-test, $t_{(7)}$=6.468, p=0.0002). h, Fluorescence trace showing injection of isoproterenol i.p. activates CaMKII+ basolateral amygdalar populations (upper) recorded by fiber photometry system. Lower Trace shows signals recorded by saline injection as control. Zoomed-in wave shapes from the dot frame are showed by side. i, Fluorescence trace showing injection of isoproterenol i.p. activates CaMKII+ basolateral amygdalar populations (upper) recorded by wireless photometry system. Lower Trace shows signals recorded by saline injection as control. Zoomed-in wave shapes from the dot frame are showed by side. j, Event frequency change (Δevents/min) before/after saline (open bars)/ISO (solid bars) for signals recording from fiber photometry system (light green) and wireless system (dark green). ISO induced significantly higher Δevents/min compared to saline in both systems (n=14, unpaired t-test, $t_{(14)}$=4.973, p=0.0002 for fiber photometry system; n=12, unpaired t-test, $t_{(12)}$=5.915, p<0.0001 for fiber photometry system). Furthermore, post-ISO signal recorded from wireless system has a significantly higher Δevents/min compared with signals from the fiber photometry system (n=13, unpaired t-test, $t_{(13)}$=3.083, p=0.0087).

The Table S1 summarizes standard deviations of the fluorescence signals in 20 s duration at different $Ca^{2+}$ concentrations from the fiber optic system and the wireless photometry probe.

TABLE S1

| Ca²⁺ concentrations (μM) | Standard deviations | |
|---|---|---|
| | Fiber photometry | Wireless photometry |
| 0.1 | 196.3 | 2 |
| 1 | 120.8 | 4.2 |
| 5 | 77.1 | 3.6 |
| 10 | 45.3 | 3.0 |

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and method steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Whenever a range is given in the specification, for example, a temperature range, a time range, or a size range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following references relate generally to fabrication methods, structures and systems for making electronic devices, including electronic devices for interfacing with biological tissue, and are hereby incorporated by reference to the extent not inconsistent with the disclosure in this application.

| Attorney Docket No. | Application No. | Filing Date | Publication No. | Publication Date | Patent No. | Issue Date |
|---|---|---|---|---|---|---|
| 145-03 US | 11/001,689 | Dec. 1, 2004 | 2006/0286488 | Dec. 21, 2006 | 7,704,684 | Apr. 27, 2010 |
| 18-04 US | 11/115,954 | Apr. 27, 2005 | 2005/0238967 | Oct. 27, 2005 | 7,195,733 | Mar. 27, 2007 |
| 38-04A US | 11/145,574 | Jun. 2, 2005 | 2009/0294803 | Dec. 3, 2009 | 7,622,367 | Nov. 24, 2009 |
| 38-04B US | 11/145,542 | Jun. 2, 2005 | 2006/0038182 | Feb. 23, 2006 | 7,557,367 | Jul. 7, 2009 |
| 43-06 US | 11/421,654 | Jun. 1, 2006 | 2007/0032089 | Feb. 8, 2007 | 7,799,699 | Sep. 21, 2010 |
| 38-04C US | 11/423,287 | Jun. 9, 2006 | 2006/0286785 | Dec. 21, 2006 | 7,521,292 | Apr. 21, 2009 |
| 41-06 US | 11/423,192 | Jun. 9, 2006 | 2009/0199960 | Aug. 13, 2009 | 7,943,491 | May 17, 2011 |
| 25-06 US | 11/465,317 | Aug. 17, 2006 | — | — | — | — |
| 137-05 US | 11/675,659 | Feb. 16, 2007 | 2008/0055581 | Mar. 6, 2008 | — | — |
| 90-06 US | 11/782,799 | Jul. 25, 2007 | 2008/0212102 | Sep. 4, 2008 | 7,705,280 | Apr. 27, 2010 |
| 134-06 US | 11/851,182 | Sep. 6, 2007 | 2008/0157235 | Jul. 3, 2008 | 8,217,381 | Jul. 10, 2012 |
| 151-06 US | 11/858,788 | Sep. 20, 2007 | 2008/0108171 | May 8, 2008 | 7,932,123 | Apr. 26, 2011 |
| 216-06 US | 11/981,380 | Oct. 31, 2007 | 2010/0283069 | Nov. 11, 2010 | 7,972,875 | Jul. 5, 2011 |
| 116-07 US | 12/372,605 | Feb. 17, 2009 | — | — | — | — |
| 213-07 US | 12/398,811 | Mar. 5, 2009 | 2010/0002402 | Jan. 7, 2010 | 8,552,299 | Oct. 8, 2013 |
| 38-04D US | 12/405,475 | Mar. 17, 2009 | 2010/0059863 | Mar. 11, 2010 | 8,198,621 | Jun. 12, 2012 |
| 170-07 US | 12/418,071 | Apr. 3, 2009 | 2010/0052112 | Mar. 4, 2010 | 8,470,701 | Jun. 25, 2013 |
| 38-04A1 US | 12/564,566 | Sep. 22, 2009 | 2010/0072577 | Mar. 25, 2010 | 7,982,296 | Jul. 19, 2011 |
| 71-07 US | 12/669,287 | Jan. 15, 2010 | 2011/0187798 | Aug. 4, 2011 | 9,061,494 | Jun. 23, 2015 |
| 60-09 US | 12/778,588 | May 12, 2010 | 2010/0317132 | Dec. 16, 2010 | 8,865,489 | Oct. 21, 2014 |
| 43-06A US | 12/844,492 | Jul. 27, 2010 | 2010/0289124 | Nov. 18, 2010 | 8,039,847 | Oct. 18, 2011 |
| 15-10 US | 12/892,001 | Sep. 28, 2010 | 2011/0230747 | Sep. 22, 2011 | 8,666,471 | Mar. 4, 2014 |
| 19-10 US | 12/916,934 | Nov. 1, 2010 | 2012/0105528 | May 3, 2012 | 8,562,095 | Oct. 22, 2013 |
| 3-10 US | 12/947,120 | Nov. 16, 2010 | 2011/0170225 | Jul. 14, 2011 | 9,057,994 | Jun. 16, 2015 |
| 118-08 US | 12/996,924 | Dec. 8, 2010 | 2011/0147715 | Jun. 23, 2011 | 8,946,683 | Feb. 3, 2015 |
| 126-09 US | 12/968,637 | Dec. 15, 2010 | 2012/0157804 | Jun. 21, 2012 | — | — |
| 50-10 US | 13/046,191 | Mar. 11, 2011 | 2012/0165759 | Jun. 28, 2012 | — | — |
| 151-06A US | 13/071,027 | Mar. 24, 2011 | 2011/0171813 | Jul. 14, 2011 | 8,895,406 | Nov. 25, 2014 |
| 137-05A US | 13/095,502 | Apr. 27, 2011 | — | — | — | — |
| 216-06B US | 13/100,774 | May 4, 2011 | 2011/0266561 | Nov. 3, 2011 | 8,722,458 | May 13, 2014 |
| 38-04A2 US | 13/113,504 | May 23, 2011 | 2011/0220890 | Sep. 15, 2011 | 8,440,546 | May 14, 2013 |
| 136-08 US | 13/120,486 | Aug. 4, 2011 | 2011/0277813 | Nov. 17, 2011 | 8,679,888 | Mar. 25, 2014 |
| 151-06B US | 13/228,041 | Sep. 8, 2011 | 2011/0316120 | Dec. 29, 2011 | — | — |
| 43-06B US | 13/270,954 | Oct. 11, 2011 | 2012/0083099 | Apr. 5, 2012 | 8,394,706 | Mar. 12, 2013 |
| 3-11 US | 13/349,336 | Jan. 12, 2012 | 2012/0261551 | Oct. 18, 2012 | — | — |
| 38-04E US | 13/441,618 | Apr. 6, 2012 | 2013/0100618 | Apr. 25, 2013 | 8,754,396 | Jun. 17, 2014 |
| 134-06B US | 13/441,598 | Apr. 6, 2012 | 2012/0327608 | Dec. 27, 2012 | 8,729,524 | May 20, 2014 |
| 28-11 US | 13/472,165 | May 15, 2012 | 2012/0320581 | Dec. 20, 2012 | — | — |
| 7-11 US | 13/486,726 | Jun. 1, 2012 | 2013/0072775 | Mar. 21, 2013 | 8,934,965 | Jan. 13, 2015 |
| 29-11 US | 13/492,636 | Jun. 8, 2012 | 2013/0041235 | Feb. 14, 2013 | — | — |
| 84-11 US | 13/549,291 | Jul. 13, 2012 | 2013/0036928 | Feb. 14, 2013 | — | — |
| 25-06A US | 13/596,343 | Aug. 28, 2012 | 2012/0321785 | Dec. 20, 2012 | 8,367,035 | Feb. 5, 2013 |
| 150-11 US | 13/624,096 | Sep. 21, 2012 | 2013/0140649 | Jun. 6, 2013 | — | — |
| 38-04A3 US | 13/801,868 | Mar. 13, 2013 | 2013/0320503 | Dec. 5, 2013 | 8,664,699 | Mar. 4, 2014 |
| 125-12 US | 13/835,284 | Mar. 15, 2013 | 2014/0220422 | Aug. 7, 2014 | — | — |
| 30-13 US | 13/853,770 | Mar. 29, 2013 | 2013/0333094 | Dec. 19, 2013 | — | — |
| 15-10A US | 14/140,299 | Dec. 24, 2013 | 2014/0163390 | Jun. 12, 2014 | — | — |
| 38-04A4 US | 14/155,010 | Jan. 14, 2014 | 2014/0191236 | Jul. 10, 2014 | — | — |
| 136-08A US | 14/173,525 | Feb. 5, 2014 | 2014/0216524 | Aug. 7, 2014 | 9,105,782 | Aug. 11, 2015 |
| 216-06C US | 14/209,481 | Mar. 13, 2014 | 2014/0373898 | Dec. 25, 2014 | 9,117,940 | Aug. 25, 2015 |
| 134-06C US | 14/220,910 | Mar. 20, 2014 | 2014/0374872 | Dec. 25, 2014 | — | — |
| 38-04F US | 14/220,923 | Mar. 20, 2014 | 2015/0001462 | Jan. 1, 2015 | 9,105,555 | Aug. 11, 2015 |
| 151-06C US | 14/246,962 | Apr. 7, 2014 | 2014/0361409 | Dec. 11, 2014 | — | — |
| 56-13 US | 14/251,259 | Apr. 11, 2014 | 2014/0323968 | Oct. 30, 2014 | — | — |
| 62-13 US | 14/250,671 | Apr. 11, 2014 | 2014/0305900 | Oct. 16, 2014 | — | — |
| 60-09A US | 14/479,100 | Sep. 5, 2014 | 2015/0132873 | May 14, 2015 | — | — |
| 84-13 US | 14/504,736 | Oct. 2, 2014 | 2015/0141767 | May 21, 2015 | — | — |
| 213-07B US | 14/521,319 | Oct. 22, 2014 | 2015/0181700 | Jun. 25, 2015 | — | — |
| 7-11A US | 14/532,687 | Nov. 4, 2014 | 2015/0080695 | Mar. 19, 2015 | — | — |
| 2-14 US | 14/599,290 | Jan. 16, 2015 | 2015/0207012 | Jul. 23, 2015 | — | — |
| 71-07A US | 14/686,304 | Apr. 14, 2015 | 2015/0290938 | Oct. 15, 2015 | — | — |
| 213-07C US | 14/706,733 | May 7, 2015 | 2015/0237711 | Aug. 20, 2015 | — | — |
| 38-04G US | 14/789,645 | Jul. 1, 2015 | 2016/0027737 | Jan. 28, 2016 | — | — |
| 216-06D US | 14/800,363 | Jul. 15, 2015 | — | — | — | — |
| 97-14 US | 14/818,109 | Aug. 4, 2015 | — | — | — | — |
| 128-13 US | 14/766,333 | Aug. 6, 2015 | 2015/0380355 | Dec. 31, 2015 | — | — |
| 15-13 US | 14/766,926 | Aug. 10, 2015 | — | — | — | — |
| 35-13 US | 14/772,354 | Sep. 2, 2015 | 2016/0005700 | Jan. 7, 2016 | — | — |
| 54-13 US | 14/772,312 | Sep. 2, 2015 | — | — | — | — |
| 176-14 US | 14/944,039 | Nov. 17, 2015 | — | — | — | — |
| 8-14 US | 14/766,301 | Dec. 24, 2015 | 2015/0373831 | Dec. 24, 2015 | — | — |

| Attorney Docket No. | Application No. | Filing Date | Publication No. | Publication Date |
|---|---|---|---|---|
| 100-14A WO | PCT/US2015/053452 | Oct. 1, 2015 | — | — |
| 69-15 WO | PCT/US2015/044573 | Aug. 11, 2015 | — | — |

| 100-14 WO | PCT/US2015/044588 | Aug. 11, 2015 | — | — |
| 99-14 WO | PCT/US2015/044638 | Aug. 11, 2015 | — | — |

We claim:

1. An implantable biomedical device for interfacing with a target tissue, said device comprising:
   a planar substrate having an open architecture to form a central opening;
   an electronic device supported by said substrate;
   a freely positionable injectable needle positioned in the central opening and electronically connected to said electronic device by a deformable interconnect, wherein the deformable interconnect is movable with a filamentary or serpentine configuration to provide controlled movement of the freely positionable injectable needle in any one, two, or three-dimensions and position the freely positionable injectable needle out of a plane formed by the planar substrate and into tissue at a desired location;
   an optical source connected to said injectable needle; wherein said optical source has an emitting area less than or equal to $1 \times 10^6$ $\mu m^2$;
   wherein said electronic device comprises a coil having an inner diameter around the central opening, and said injectable needle and said deformable interconnect are disposed within said coil inner diameter and said coil is a magnetic loop antenna for wireless power delivery.

2. The implantable biomedical device of claim 1, wherein said electronic device, said injectable needle and said deformable interconnect each comprise a thin film structure.

3. The implantable biomedical device of claim 1, wherein said freely positionable injectable needle is moveable out of a plane formed by the electronic device, and the deformable interconnect provides movement of the freely positionable injectable needle without movement of the electronic device.

4. The implantable biomedical device of claim 1, wherein said freely positionable injectable needle is moveable within a substantially conical volume around a point defined by the intersection of the deformable interconnect and the electronic device.

5. The implantable biomedical device of claim 1, that is a millimeter-scale device with a mass equal to or less than 1000 mg.

6. The implantable biomedical device of claim 1, wherein said electronic device further comprises one or more of a rectifier, a capacitor, and an optical indicator.

7. The implantable biomedical device of claim 6, wherein said coil has an outer diameter less than or equal to 9.8 mm.

8. The implantable biomedical device of claim 1, wherein said electronic device has a thickness less than or equal to 5 mm.

9. The implantable biomedical device of claim 1, wherein said electronic device is flexible and configured to accommodate a radius of curvature greater than or equal to 10 mm without mechanical failure.

10. The implantable biomedical device of claim 1, wherein said electronic device comprises one or more optical indicators each independently having an emitting area less than or equal to $1 \times 10^6$ $\mu m^2$.

11. The implantable biomedical device of claim 10, wherein said optical indicator provides a radiant output characterized by a surface power density of 0.1 $mW \cdot mm^{-2}$ to 500 $mW \cdot mm^{-2}$.

12. The implantable biomedical device of claim 10, wherein said optical indicator provides a radiant output during use selected to provide a change in temperature of said target tissue equal to or less than 5° C.

13. The implantable biomedical device of claim 10, wherein said optical indicator emits electromagnetic radiation having a wavelength between 300 nm and 850 nm.

14. The implantable biomedical device of claim 1, wherein said injectable needle has one or more of a thickness less than or equal to 500 $\mu m$, a width less than or equal to 500 $\mu m$, a length selected from a range of 0.1 mm to 10 mm, or a cross-sectional area less than or equal to 0.25 $mm^2$.

15. The implantable biomedical device of claim 1, wherein said injectable needle or a portion thereof is configured to individually address a cell or group of cells of said target tissue, wherein at least one cell is a transformed cell and said optical source in use changes expression of one or more light-responsive proteins in said transformed cell.

16. The implantable biomedical device of claim 1, wherein said injectable needle has a net bending stiffness greater than or equal to $1 \times 10^8$ $GPa \cdot \mu m^4$.

17. The implantable biomedical device of claim 1, wherein said injectable needle has a distal tip end that is tapered for insertion into said target tissue, wherein said distal tip end taper is to a pointed end having a lateral dimension selected from a range that is greater than or equal to 10 nm and less than or equal to 100 $\mu m$ and said distal end taper traverses a longitudinal distance that is less than 0.5 mm from the pointed end.

18. The implantable biomedical device of claim 1, further comprising a tab at an intersection of said injectable needle and said deformable interconnect to facilitate controlled movement of said injectable needle in three dimensions.

19. The implantable biomedical device of claims 1, wherein said deformable interconnect is flexible, stretchable, bendable, or any combination thereof.

20. The implantable biomedical device of claim 1, wherein said deformable interconnect has a serpentine, coiled and/or bent geometry.

21. The implantable biomedical device of claim 1, wherein said deformable interconnect is configured to accommodate a strain of up to 100% without mechanical failure.

22. The implantable biomedical device of claim 1, wherein said optical source has an emitting area selected from the range of $1 \times 10^3$ $\mu m^2$ to $1 \times 10^5$ $\mu m^2$ and said optical source provides a radiant output during use selected to provide a change in temperature of said target tissue equal to or less than 2° C.

23. The implantable biomedical device of claim 1, wherein said injectable needle comprises at least one photodetector, wherein said photodetector has a sensing area less than or equal to 1 $mm^2$.

24. The implantable biomedical device of claim 1, wherein said substrate comprises a material selected from the group consisting of polyimide and polyethylene terephthalate, and wherein said substrate has a thickness selected from a range of 10 $\mu m$ to 1000 $\mu m$.

25. The implantable biomedical device of claim 1, further comprising an encapsulating material at least partially encapsulating said implantable device, wherein said encapsulating material is selected from the group consisting of poly(dimethylsiloxane), parylene-C, parylene-N, inorganic coatings and combinations of these.

26. The implantable biomedical device of claim 1, further comprising a plurality of optical sources provided along a length of said injectable needle.

27. The implantable biomedical device of claim 1, wherein said injectable needle has a distal tip end and said optical source is positioned within 1 mm from said distal tip end.

28. A method of implanting the implantable biomedical device of claim 1, the method comprising the steps of:
positioning said implantable device adjacent to a soft tissue surface of said target tissue;
inserting said freely positionable injectable needle into said soft tissue; and
contacting said implantable device with said target tissue surface or an adjacent bone surface.

29. A system comprising:
a plurality of implantable biomedical devices for interfacing with a target tissue, each of said implantable biomedical devices comprising:
a planar substrate having an open architecture to form a central opening;
an electronic device supported by said substrate;
a freely positionable injectable needle positioned in the central opening and electronically connected to said electronic device by a deformable interconnect, wherein the deformable interconnect is freely movable with a filamentary or serpentine configuration to provide controlled movement of the freely positionable injectable needle in any one, two, or three-dimensions and position the freely positionable injectable needle out of a plane formed by the planar substrate and into tissue at a desired location;
an optical source connected to said injectable needle; wherein said optical source has an emitting area less than or equal to $1\times10^6$ μm²;
wherein said electronic device comprises a coil having an inner diameter around the central opening, and said injectable needle and said deformable interconnect are disposed within said coil inner diameter;
an antenna inductively coupled to the coil of each electronic device; and
a photodiode for measuring light emitted or scattered from said target tissue.

30. The system of claim 29, further comprising a tab positioned at an intersection of the freely positionable injectable needle and the deformable interconnect, wherein the tab is configured to receive a positioner that applies a force to the freely positionable injectable needle and facilitate controlled movement of the freely positionable injectable needle in any one, two, or three-dimensions.

31. An implantable optical system for optically interfacing with a target tissue, said device comprising:
a planar substrate having an open architecture to form a central opening;
an electronic device supported by said substrate; said electronic device comprising a wireless system providing for wireless power and data communication; and
a freely positionable injectable optical probe positioned in the central opening and electronically connected to the electronic device; wherein the optical probe comprises one or more optical sources and one or more optical detectors optically collocated along a length and/or near a distal end; wherein each optical source is individually characterized by lateral dimensions equal to or less than 1000 μm and wherein each optical detector is individually characterized by lateral dimensions equal to or less than 1000 μm; wherein said wireless system at least partially powers said one or more optical sources and one or more optical detectors;
a deformable interconnect electronically connected to said freely positionable injectable optical probe, wherein the deformable interconnect is freely movable with a filamentary or serpentine configuration to provide controlled movement of the freely positionable injectable optical probe in any one, two, or three-dimensions and position the freely positionable injectable optical probe out of a plane formed by the planar substrate and into tissue at a desired location.

32. The implantable optical system of claim 31, further comprising: a tab positioned at an intersection of said freely positionable injectable optical probe and said deformable interconnect, wherein said tab is configured to receive a positioner that applies a force to said freely positionable injectable optical probe and facilitate controlled movement of said freely positionable injectable optical probe in any one, two, or three-dimensions and position said freely positionable injectable optical probe into tissue at a desired location.

33. A method of using an implantable optical system for optically interfacing with a target tissue, said method comprising:
providing an implantable optical system comprising:
a planar substrate having an open architecture to form a central opening; an electronic device supported by said substrate; said electronic device comprising a wireless system providing for wireless power and data communication; and a freely positionable injectable optical probe positioned in the central opening and electronically connected to the electronic device via a deformable interconnect; wherein the freely positionable injectable optical probe comprises one or more optical sources and one or more optical detectors optically collocated along a length and/or near a distal end; wherein each optical source is individually characterized by lateral dimensions equal to or less than 1000 μm and wherein each optical detector is individually characterized by lateral dimensions equal to or less than 1000 μm; wherein said wireless system at least partially powers said one or more optical sources and one or more optical detectors; a deformable interconnect electronically connected to said freely positionable injectable optical probe, wherein the deformable interconnect is freely movable with a filamentary or serpentine configuration to provide controlled movement of the freely positionable injectable optical probe in any one, two, or three-dimensions and position the freely positionable injectable probe into tissue at a desired location;
inserting said freely positionable injectable optical probe out of a plane formed by the planar substrate and into said target tissue; and
sensing and/or actuating said target tissue with said one or more optical sources and/or said one or more optical detectors.

34. The method of claim 30, wherein the implantable optical system further comprises a tab positioned at an intersection of said freely positionable injectable optical probe and said deformable interconnect, wherein said tab is configured to receive a positioner that applies a force to said freely positionable injectable optical probe and facilitate controlled movement of said freely positionable injectable optical probe in any one, two, or three-dimensions and position said freely positionable injectable optical probe into tissue at a desired location.

35. A method of using an implantable biomedical device for interfacing with a target tissue, the method comprising:
providing said implantable biomedical device comprising;
a planar substrate having an open architecture to form a central opening;
an electronic device supported by said substrate;
a freely positionable injectable needle positioned in the central opening and electronically connected to the electronic device by a deformable interconnect; said injectable needle having one or more optical sources provided along a length of said injectable needle and/or near a distal tip end of said injectable needle; wherein each optical source is individually characterized by an emitting area less than or equal to $1\times10^6$ µm$^2$; wherein the deformable interconnect is freely movable with a filamentary or serpentine configuration to provide controlled movement of the freely positionable injectable needle in any one, two, or three-dimensions and position the freely positionable injectable needle out of a plane formed by the planar substrate and into tissue at a desired location
inserting said freely positionable injectable needle into said target tissue; and
actuating said target tissue with said one or more optical sources.

36. The method of claim 35, wherein the implantable biomedical device further comprises a tab positioned at an intersection of said freely positionable injectable optical probe and said deformable interconnect, wherein said tab is configured to receive a positioner that applies a force to said freely positionable injectable optical probe and facilitate controlled movement of said freely positionable injectable optical probe in any one, two, or three-dimensions and position said freely positionable injectable optical probe into tissue at a desired location.

37. An implantable biomedical device for interfacing with a target tissue, said device comprising:
a planar substrate having an open architecture to form a central opening;
an electronic device supported by said substrate; and
a freely positionable probe positioned in the central opening and electronically connected to the electronic device by a deformable interconnect; said probe having one or more optical sources provided along a length of said probe and/or near a distal tip end of said probe; wherein each optical source is individually characterized by an emitting area less than or equal to $1\times10^6$ µm$^2$;
wherein the deformable interconnect is freely movable with a filamentary or serpentine configuration to provide controlled movement of the freely positionable probe in any one, two, or three-dimensions and position the freely positionable probe out of a plane formed by the planar substrate and into tissue at a desired location.

38. The implantable biomedical device of claim 37, further comprising: a tab positioned at an intersection of said freely positionable probe and said deformable interconnect, wherein said tab is configured to receive a positioner that applies a force to said freely positionable probe and facilitate controlled movement of said freely positionable probe in any one, two, or three-dimensions and position said freely positionable probe into tissue at a desired location.

* * * * *